(12) United States Patent
Kurani et al.

(10) Patent No.: US 10,577,256 B1
(45) Date of Patent: Mar. 3, 2020

(54) WATER MONITORING DEVICE WITH REPLACEABLE REAGENT CARTRIDGE

(71) Applicant: Sutro Connect, Inc., Vancouver (CA)

(72) Inventors: Ravi Kurani, San Francisco, CA (US); Daniel Proterra, San Francisco, CA (US); Alexandr Valeyev, Concord, CA (US)

(73) Assignee: SUTRO CONNECT INC., Vancouver (CA)

(*) Notice: Subject to any disclaimer, the term of this patent is extended or adjusted under 35 U.S.C. 154(b) by 0 days.

(21) Appl. No.: 16/411,458

(22) Filed: May 14, 2019

Related U.S. Application Data

(63) Continuation of application No. 15/990,242, filed on May 25, 2018, now Pat. No. 10,287,180, which is a continuation-in-part of application No. 15/649,994, filed on Jul. 14, 2017, now Pat. No. 10,150,680, which is a continuation-in-part of application No. 14/988,554, filed on Jan. 5, 2016, now Pat. No. 9,776,888.

(60) Provisional application No. 62/510,829, filed on May 25, 2017, provisional application No. 62/362,438, filed on Jul. 14, 2016, provisional application No.
(Continued)

(51) Int. Cl.
| | |
|---|---|
| *G08B 21/00* | (2006.01) |
| *C02F 1/00* | (2006.01) |
| *G01N 31/22* | (2006.01) |
| *G08B 5/22* | (2006.01) |
| *C02F 1/66* | (2006.01) |
| *C02F 103/42* | (2006.01) |

(52) U.S. Cl.
CPC ............... *C02F 1/003* (2013.01); *C02F 1/66* (2013.01); *G01N 31/221* (2013.01); *G08B 5/225* (2013.01); *C02F 2103/42* (2013.01); *C02F 2201/009* (2013.01); *C02F 2209/006* (2013.01); *C02F 2209/008* (2013.01); *C02F 2209/04* (2013.01); *C02F 2209/055* (2013.01); *C02F 2209/06* (2013.01); *C02F 2209/07* (2013.01); *C02F 2209/08* (2013.01); *C02F 2209/29* (2013.01)

(58) Field of Classification Search
CPC .. C02F 1/66; C02F 2103/42; C02F 2201/009; C02F 2209/006; C02F 2209/008; C02F 2209/04; C02F 2209/055; C02F 2209/06; C02F 2209/07; C02F 2209/08; C02F 2209/29; G01N 31/221; G08B 5/225
See application file for complete search history.

(56) References Cited

U.S. PATENT DOCUMENTS

| | | | |
|---|---|---|---|
| 6,245,224 B1 * | 6/2001 | Enoki .................... | C02F 1/008 137/93 |
| 2012/0214250 A1 * | 8/2012 | Oura ...................... | G01N 21/80 436/163 |

(Continued)

*Primary Examiner* — Munear T Akki
(74) *Attorney, Agent, or Firm* — Staniford Tomita LLP

(57) ABSTRACT

A water monitoring device monitors and maintains swimming pool chemistry. The device mixes reagents with water in flowcells. The water chemistry is detected by measuring the light transmitted through the flowcells. The water monitoring device can communicate with computers, servers and mobile computing devices which can store and display the water chemistry information. The reagents can be stored in a replaceable reagent cartridge which can provide reagents for water testing and can be replaced when the reagents need to be replenished.

1 Claim, 32 Drawing Sheets

Related U.S. Application Data

62/099,684, filed on Jan. 5, 2015, provisional application No. 62/274,737, filed on Jan. 4, 2016.

(56) References Cited

U.S. PATENT DOCUMENTS

2012/0249333 A1* 10/2012 Kunis ............... G01N 1/14
    340/603
2018/0112430 A1* 4/2018 Shalon ............. G01N 33/18

* cited by examiner

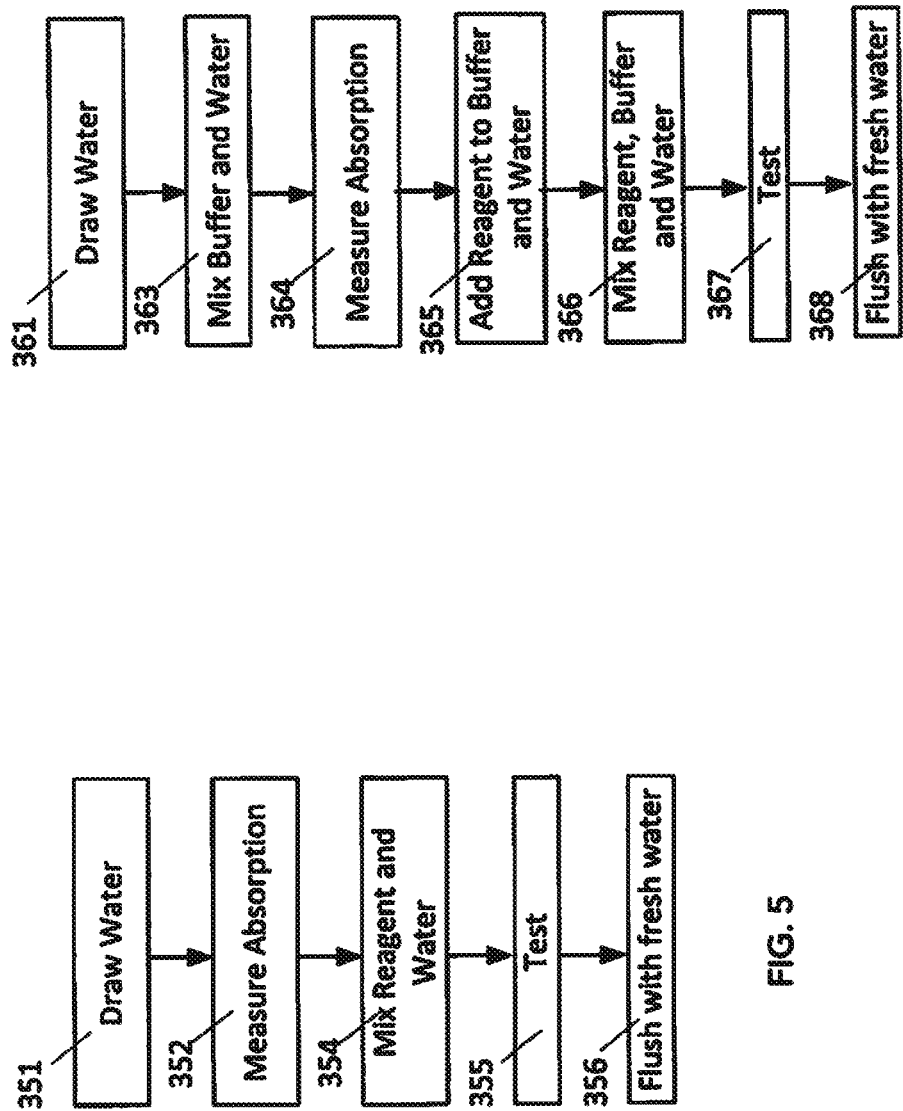

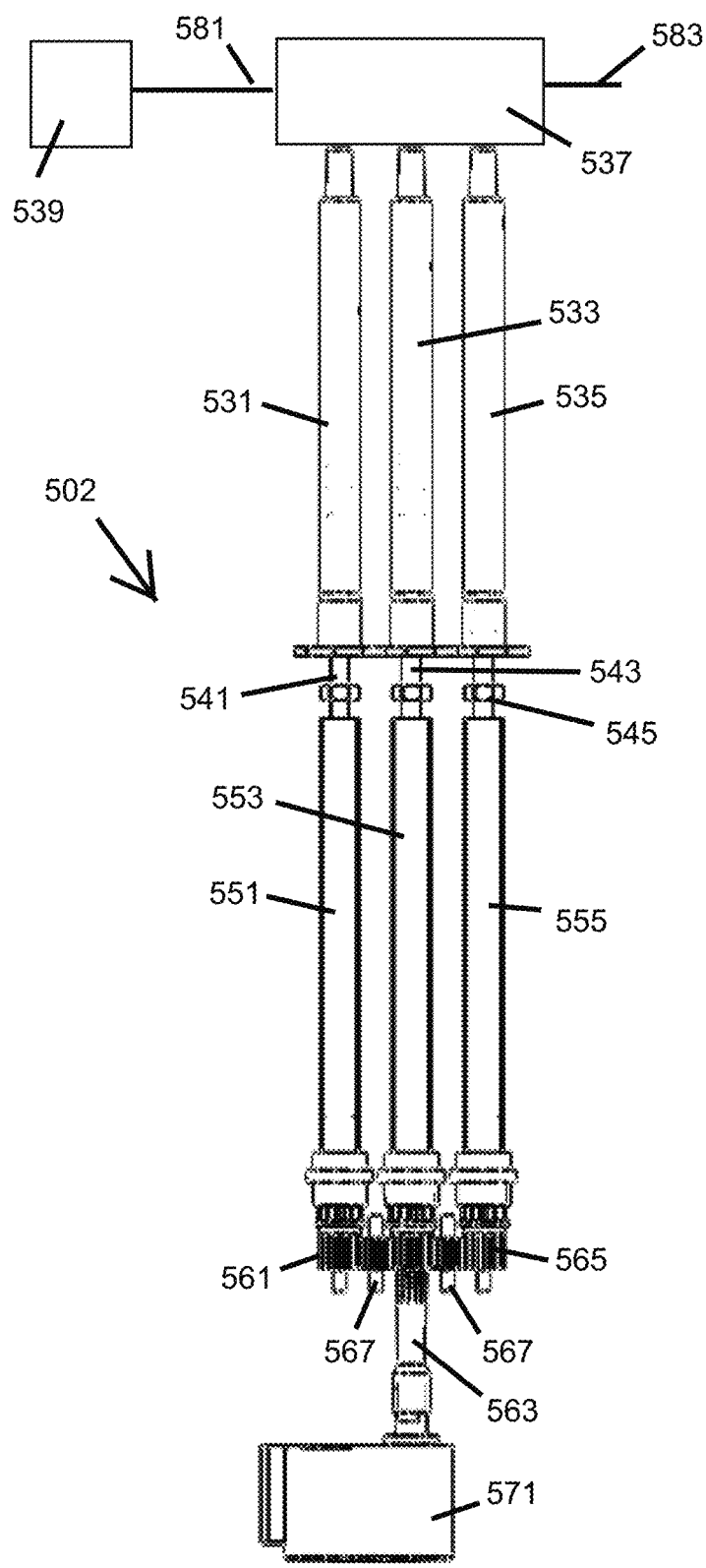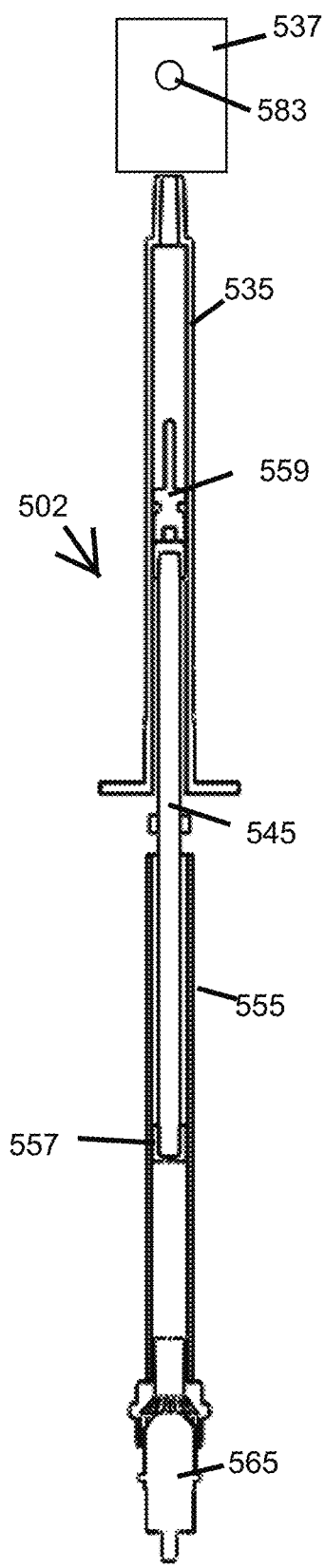
FIG. 22
FIG. 23

WATER MONITORING DEVICE WITH REPLACEABLE REAGENT CARTRIDGE

CROSS REFERENCE TO RELATED APPLICATIONS

This patent application is a continuation of U.S. patent application Ser. No. 15/990,242, "Water Monitoring Device And Method" filed May 25, 2018, which is now U.S. Pat. No. 10,287,180, which claims priority to U.S. Provisional Patent Application No. 62/510,829, "Water Monitoring Device And Method" filed May 25, 2017. U.S. patent application Ser. No. 15/990,242 is also a continuation in part of U.S. patent application Ser. No. 15/649,994, "Water Monitoring Device And Method" filed Jul. 14, 2017 which claims priority to U.S. Provisional Patent Application 62/362,438, "Water Monitoring Device And Method" filed Jul. 14, 2016. U.S. patent application Ser. No. 15/649,994, "Water Monitoring Device And Method" filed Jul. 14, 2017, is a continuation in part of U.S. patent application Ser. No. 14/988,554, "Water Monitoring Device And Method" filed Jan. 5, 2016 now U.S. Pat. No. 9,776,888, which claims priority to U.S. Provisional Patent Application No. 62/099,684, "Water Monitoring Device And Method" filed Jan. 5, 2015, and U.S. Provisional Patent Application No. 62/274,737, "Water Monitoring Device And Method" filed Jan. 4, 2016. U.S. patent application Ser. Nos. 15/990,242, 15/649,994, 14/988,554, 62/510,829, 62/362,438, 62/099,684, and 62/274,737 are hereby incorporated by reference in their entirety.

BACKGROUND

Pool owners often manage their own swimming pool chemistry and equipment. There are 14.4 million residential pools and spas in the United States with 85% of pool owners managing their own pool. Managing chemistry is the largest problem for 80% of pool owners since managing a pool is confusing and time consuming and purchasing pool products is complicated. Pool owners may spend upwards of 4-6 hours on chemical management and skimming pool water. With current pool management kits, owners often manage their pool incorrectly, resulting in a cumulative $960 extra spent on pool mismanagement, 176 billion gallons of water used and misused, and 20% more energy wasted on running dirty pools. Individually, pool and spa owners spend upwards of $120/month on chemicals and, on average, their pool goes 'green' meaning, it grows algae or gets cloudy usually caused by a pH imbalance once a season. This algae growth and its prevention are not well understood by end-users. Users spend extra money on toxic chemicals to try to "reset" their water chemistry, energy costs because dirty water takes more energy to circulate, repairing equipment malfunctions due to dirty water, and water costs due to dumping and replacing dirty water. What is needed is a monitoring system with a replaceable reagent cartridge that will inform pool owners of the pool chemical levels and chemical adjustments needed to properly maintain their pools and spas so that they are always in proper pH balance to save money, conserve water and prevent unnecessary maintenance.

SUMMARY OF THE INVENTION

A water monitoring device monitors and maintains swimming pool chemistry. The device includes sensors that detect water chemistry that can communicate with a pool computer and a server. The system can determine if corrections to the water chemistry are required to maintain water sanitation. The device can monitor: pH, air temperature, water temperature, free chlorine levels, oxidation reduction potential, alkalinity, oxygen demand, water movement and velocity, and electrical conductivity.

In an embodiment, as discussed above the water monitoring device can include sensors, connectivity mechanisms, 'knowledge' of device's location, solar panels and/or battery, rounded disk-like design, mass-spring-dashpot system to aide in impact of sensor on the ground, water-proof housing, remote proprietary chemistry algorithms, mobile, web applications, and messaging capabilities. These processes can be performed by a processor that is coupled to sensors, transducers, a power supply and a memory. In an embodiment, the device may include sensors that can measure and provide proxy values for: pH levels, ambient air temperature, water temperature, free chlorine levels, ORP (oxidation reduction potential), alkalinity, oxygen demand (biological, chemical), etc. The system may also include an accelerometer that can be used to measure: fluctuations in water movement (or air movement), velocity at the water surface, electrical conductivity (total dissolved solids, salinity units, salinity, specific gravity), pressure at the water surface, pressure of water at the device submersion point, volume of water (as per user input).

In an embodiment, the water monitoring device can include a connectivity mechanism which includes, but is not limited to RF transducers which can provide wireless communications with other devices through various protocols including: WiFi (IEEE 802.11, IEEE 802.11ac, IEEE 802.11n), Bluetooth and BLE (Bluetooth low energy), Electric Imp protocol, Zigbee, Z-Wave, Android OS, Apple iBeacon, PayPal proximity sensor, GPRS/GSM/3G/4G/Edge, etc. The transducers can provide a means for communications with other devices such as mobile phones, computers, other water sensor devices, etc.

In an embodiment, the water monitoring device can include nodal mesh 'knowledge' of device's location. The location information can be useful in predicting the upcoming weather conditions. Water maintenance can be related to the ambient temperature. If warmer weather is predicted in the near future, the system can prepare the water by recommending an adjustment of the chemicals in the water prior to the increased temperatures. The warmer temperatures can result in more algae growth if the pool chemicals are not adjusted.

In an embodiment, the water monitoring device can be powered by solar panels, which can maintain an electrical charge on a battery. During the day, the system can run off of solar power and when the solar panel is not collecting energy at night, the system can operate off of battery power. In other embodiments, the device can be powered to rechargeable batteries which can be periodically charged by available electrical power supplies. For example, in an embodiment, the device can have a charging port which can be coupled to a low voltage DC electrical current power supply which is coupled to a 110 AC or 220 AC power supply.

In an embodiment, the water monitoring device can have an inlet of water near the base and a water or liquid circulation technology mechanism so that ambient water is constantly being pumped into one or more flowcells for chemical testing purposes and cleaning of the residual chemicals from the flowcells. This reservoir may hold liquid even when not submerged such that sensors are kept wet while out of water or other liquid. In an embodiment, the water monitoring device may have partial liquid submersion functionality, including but not limited to partial submersion into pools, wells, waterways, rivers, spas, Jacuzzis, hot tubs, reservoirs of any kind, and applications related to agriculture, irrigation, aqueducts, drinking water, fracking, groundwater testing, city and municipal water wells and meters.

Although the water monitoring device has been illustrated as a device that floats on the surface of the water, with a portion submerged and a portion above the water line, in another embodiment, the device could be fully submerged at the bottom of a pool or other water source. Because radio frequency waves do not travel well through water, connective communication wires and/or tubes for the device can run up from a floor or wall(s) to a dry area outside of the body of water. The wires can provide electrical power as well as communications from the water monitoring device so that the device can function as described above.

In an alternative embodiment, the water monitoring device could be placed on the outside of the pool, such as on a deck. One or more water sensors can be connected or in communication with the water monitoring device and these sensors can contact the water or be in close proximity to the water by hanging over the water surface. Pools and hot tubs may have skimmers that can be installed outside the perimeter of the pool and function to remove floating debris from the pool. Water circulates from the pool to the skimmer and the debris can be trapped in baskets or filters that are held in the skimmers. The skimmer baskets or filters can be accessed by removing a lid of the skimmer that is adjacent to the edge of the pool. In an embodiment, the device can be placed in a lid such as a skimmer lid, where the lid is covering an access area to the inlet or outlet of the pool.

In another embodiment, the water monitoring device could be built into a heating, plumbing or filtration system when the water system structure is being constructed and later connected to a network. For example, the water monitoring device and/or sensor(s) could be placed inline with pool plumbing. In other embodiments, the water monitoring device and/or sensor(s) could be placed anywhere around the water system, as long as a portion of the sensor cluster comes in contact with the water. In an embodiment, the water monitoring device and/or sensor(s) could be attached to a filter bank through a filter gauge installment.

In an embodiment, the water monitoring device and/or sensor(s) can be incorporated with other pool related products. For example, in an embodiment, the water monitoring device could include a music speaker set on an exposed above water portion with sensors attached to the bottom of a floating music device. The water monitoring device can include a Wi-Fi or Bluetooth receiver that can receive RF music signals and emit the music through the speaker set.

In an embodiment, the water monitoring device could be attached to an automatic or human powered floating water top skimmer that can move across the surface of the pool cleaning the surface debris. In an embodiment, the design could be a replacement part for an existing automatic pool cleaner. For submerged pool cleaners, the water monitoring device can have communications waterproof insulated wires could be run through a hose or be attached to the pool cleaner hose with the opposite ends exiting the water.

In an embodiment, the water monitoring device may include remote proprietary chemistry algorithms. These algorithms may include a pH and alkalinity buffer. The algorithm may make correlations to weather stations provided by governmental organizations, private organizations, or citizens through organizations like Smart Citizen. The algorithms may also process salt content, water hardness/softness, rate of evaporation, energy consumption as a function of chemical balances and electricity rates.

In an embodiment, the water monitoring device includes application software and messaging capabilities. For example, these capabilities may include communication via the application and through SMS, email, push notifications, wearable tech notifications, physical notifications through product indicators, etc. These communications may provide end users with actionable insight into their pool water chemistry and provide a sales and delivery platform of chemicals and/or solutions. For example, when more chemicals such as chlorine or acid are required, the system can transmit messages to the user indicating the chemical and quantity of the chemical needed. The user can respond to the messages by indicating that the specified chemicals will be added to the pool water at a predicted time period such as within 1 hour or any other time increment. If the system does not detect a change in water chemistry, it can transmit a reminder to the user soon after the predicted time period has elapsed. If the user does not add the requested chemicals, the system can update the quantity of requested chemicals as the conditions of the water change.

In an embodiment of the method for using the water monitoring device, water data information is sent to a computer network, such as an analytics cloud. The network can then send tracking information and actionable data to a mobile device. The mobile device can then be used to purchase pool maintenance products. The pool products can be shipped to the pool owner. The water monitoring device can then instruct the owner on the use of the pool maintenance products to correct or maintain the water chemistry at optimum levels. In an embodiment, the water monitoring device can be set up and configured once and may remain operational providing water chemistry information for the life of the product. System updates can be performed via wireless communications.

In an embodiment, the water monitoring device may include mobile, web applications and cloud-based database and associated UX/UI to facilitate pool, water, or liquid management. Data from the device can be transmitted and stored on a cloud server. This water and device data can then be stored for the water of the individual user or business. This data can provide a historical record of the water metrics and provide an analysis of the chemicals used by the system for any prior time period. Based on the past history and/or the relationship between water and ambient conditions, the necessary chemicals can be predicted for future use.

Swimming pool water must maintain low levels of bacteria and viruses to prevent the spread of diseases and pathogens. Bacteria, algae and insect larvae can enter the pool if water is not properly sanitized. Pumps, mechanical filters, and disinfectants are often used to sanitize the water.

Chemical disinfectants, such as chlorine (usually as a hypochlorite salt, such as calcium hypochlorite) and bromine, are commonly used to kill pathogens. If not properly maintained, chemical sanitation can produce high levels of disinfection byproducts. Sanitized swimming pool water can theoretically appear green if iron or certain minerals (such as copper chloride) are in the water.

There are various types of chemicals that can be added to water. For example, water chlorination is the process of adding chlorine ($Cl_2$) or hypochlorite to water as a method of water purification to make it fit for human consumption as drinking water. In particular, chlorination is used to prevent the spread of waterborne diseases.

As a halogen, chlorine is a highly efficient disinfectant, and is added to public water supplies to kill disease-causing pathogens, such as bacteria, viruses, and protozoans, that commonly grow in water supply reservoirs, on the walls of water mains and in storage tanks. The microscopic agents of many diseases such as cholera, typhoid fever, and dysentery killed countless people annually before disinfection methods were employed routinely.

Chlorine is obtained from salt (NaCl). It is a gas at atmospheric pressures but liquefies under pressure. The liquefied gas is transported and used as such. As a strong oxidizing agent, chlorine kills via the oxidation of organic molecules. Chlorine and hydrolysis product hypochlorous acid are neutrally charged and therefore easily penetrate the negatively charged surface of pathogens. It is able to disintegrate the lipids that compose the cell wall and react with intracellular enzymes and proteins, making them nonfunctional. Microorganisms then either die or are no longer able to multiply.

Shock chlorination is a process used in many swimming pools, water wells, springs, and other water sources to reduce the bacterial and algal residue in the water. Shock chlorination is performed by mixing a large amount of hypochlorite into the water. The hypochlorite can be in the form of a powder or a liquid such as chlorine bleach (solution of sodium hypochlorite in water). Water that is being shock chlorinated should not be swum in or drunk until the sodium hypochlorite count in the water goes down to three parts per million (PPM) or less.

Salt water chlorination is a process that uses dissolved salt (2,500-6,000 ppm) as a store for the chlorination system. The chlorine generator (also known as salt cell, salt generator, salt chlorinator) uses electrolysis in the presence of dissolved salt (NaCl) to produce hypochlorous acid (HCIO) and sodium hypochlorite (NaClO), which are the sanitizing agents already commonly used in swimming pools. As such, a saltwater pool is not actually chlorine-free; it simply utilizes a chlorine generator instead of direct addition of chlorine.

The presence of chlorine in traditional swimming pools can be described as a combination of free available chlorine (FAC) and combined available chlorine (CAC). While FAC is composed of the free chlorine ions that are available for sanitizing the water, the CAC includes chloramines, which are formed by the reaction of FAC with amines (introduced into the pool by human perspiration and urine). Chloramines are responsible for the "chlorine smell" of pools, as well as skin and eye irritation. These problems are the result of insufficient levels of free available chlorine and indicate a pool that must be "shocked" by the addition of 5-10 times the normal amount of chlorine. In saltwater pools, however, the generator continuously produces free chlorine ions, eliminating the formation of CAC. Electrolysis burns off chloramines in the same manner as a traditional shock (oxidizer). As with traditionally chlorinated pools, saltwater pools must be monitored in order to maintain proper water chemistry. Low chlorine levels can be caused by insufficient salt, higher-than-normal chlorine demand, low stabilizer, sun exposure, or mechanical issues with the generator. The salt count (salt concentration) can be lowered due to splash-out, backwashing, and dilution via rainwater.

In different embodiments, the inventive system can be used to monitor the chemicals in any type of chemicals used to maintain the sanitation of the pool water. The system can be easily configured for chlorine or bromine or other water chemicals through the software or firmware set up of the device or in other embodiments, an electrical switch on the device.

For example, the optimum pH level for a pool can be between about 7.4 and 7.6. If a pH reading is below 7.2 then the water is might be too acidic and if the pH reading is above 7.8, the water may be too alkaline. To keep bacterial, pathogens, and algae from growing in your water, the chlorine (sanitizer) level needs to be at a safe level for swimming. If the pH level is too low, the processor can recommend adding a pH or alkaline increaser such as baking soda can be added to the water. If the pH level is too high the processor can recommend adding a pH or alkaline reducer such as muriatic acid. The amount of chemicals needed to change the pH level will depend upon the volume of the body of water. A smaller pool will need a smaller volume of chemicals to change the pH level than a larger pool.

In an embodiment, the depth sensor can detect an average depth of the pool based on an average reading over a period of time when the water monitoring device 101 randomly moves across the entire surface of the pool. In an embodiment, the surface area of the pool can be determined from a real or satellite photographs of the pool such as Google maps or approximated by the general shape and dimensions of the pool. The volume of water can be calculated by multiplying the average depth times the surface area of the pool. In yet another embodiment, the system can initially estimate the volume of the pool based on just the surface area of the pool as determined by the owner or calculated from areal or satellite photographs of the pool such as Google maps. The system can then estimate the volume based on an average depth of a pool of 4.5 feet. However, the average depth of the pool may also be proportional to the size of the pool with larger pools typically having a larger average depth than smaller pools. The user can be offered up the surface area and may provide additional depth information. For example, the user may have to select a point where the deep end and possibly where shallow end is. From this information, the system can more accurately estimate the pool volume. The system can also perform learning tests to determine the pool volume. For example, the chlorine level can be measured and then 5 pounds of chlorine can be added. The chlorine level can be measured again and the increase in chlorine level will indicate the volume of the pool. In another example, if we originally assumed that the pool volume is 1,000,000 liters, and the user wants to increase the chlorine concentration by 1 ppm, then the system will prescribe 1 mg of chlorine. After the chlorine is added, the chlorine concentration can be remeasured to determine if the concentration actually increases by 1 ppm. If chlorine level increases more than 1 ppm, then we know that the pool was actually less than 1,000,000 liters. The actual volume of the pool can be determined by the chlorine level increase.

A smaller volume pool will have a larger ppm increase than a larger pool for the same quantity of chlorine. In other embodiments, any other chemical concentration testing can be performed to determine the pool volume. With the pool volume accurately measured, the system can make more accurate chemical recommendations.

The processor recommendation can also be based on the type of chemicals being used such as: granular chlorine, 1 inch or 3 inch tablets, sticks, etc. In an embodiment, the user may specify chemical preferences and the system may calculate a quantity of the chemicals based on the chemical and/or pH level measurements, temperature and volume of pool water. Because the system can continuously monitor the chemical and pH levels, the system can update the chemical recommendations over time.

A chlorine test reading between 1.0 and 3.0 ppm is optimal. However, if bromine is used instead of chlorine as the sanitizer, then the bromine reading should be between 2.0 and 4.0 ppm. Again, the chlorine or bromine use can be set up as a user preference. Alkalinity should be between about 100 and 120 ppm. Cyanuric acid should be between about 20 and 30 ppm. If the chemical levels are too low, the system can recommend adding these chemicals based on the ppm readings and the volume of the pool. The recommendations can provide sufficient chemicals to bring the chemicals to the optimum concentrations. However, if errors are made by the pool maintainer, the system will detect the errors and make adjustments to future chemical inputs. In addition to normal pool maintenance, the system can also schedule shock chemicals, and adjust the chemical recommendations afterward. The system may also detect algae and make recommendations for specific volumes of algaecide based on the detected quantities of algae. For example, the system can recommend adding 3 pounds of shock chemicals once a week at night and the recommend adding algaecide the next morning. The system may also recommend a sequence of steps to correct the chemical levels. For example, the system may recommend adjusting the alkalinity first. Once the alkalinity is determined to be in the proper range, the system can recommend adjusting the bromine or chlorine levels. After the alkalinity and bromine/chlorine levels are set, the system can recommend adjusting the pH level.

In different embodiments, different sensors can be used to determine the pH level. In an embodiment, a chamber is filled with water either through diffusion or via a peristaltic pump within the water monitoring device. Reagents are either mixed through a mixing chamber via a pump or via the diffusion. In alternative embodiments, the reagents can be added via a vacuum that is created through a pump. The reagents can diffuse in the water. In yet another embodiment, the reagents can be stored in a replaceable modular cartridge that is easily inserted and removed from the water monitoring device. The reagents react with the water to produce a coloring that indicates the pH level of the water. The photometer can include 3 RGB (1 red, green and 1 blue) LEDs that can be used to allow the photometer to measure 'color' of the water after it has been mixed with reagents. The absorbance of the colored light is then compared to what we have limits for, and then the values are distilled to provide input to the consumer.

In an embodiment, the pool chemicals can be stored in the water monitoring device and released at the recommended rate. Since the chemicals are added to the water through an automated device, the system can control the rate of flow of the chemicals to maintain the desired chemical balance. This constant chemical control would be better than periodic chemical adjustment because it would maintain a much better chemical balance rather than going through a cyclical chemical adjustment process.

While the above description contains many specificities, these should not be construed as limitations on the scope of any embodiment, but as exemplifications of various embodiments thereof. Many other ramifications and variations are possible within the teachings of the various embodiments. For example, the pool maintenance device may include more than one module.

The device(s) may float freely, or be anchored, or attached to the pool. The modules may include audio functionality. The device modules may include additional functions, attachments related to pool maintenance and use.

BRIEF DESCRIPTION OF THE DRAWINGS

FIG. 5 illustrates a flow chart for an embodiment of pH testing.

FIG. 6 illustrates a flow chart for an embodiment of free chlorine testing.

FIG. 22 illustrates a top view of an embodiment of a reagent cartridge with a plunger assembly.

FIG. 23 illustrates a cross section side view of an embodiment of a reagent cartridge with a plunger assembly.

DETAILED DESCRIPTION

The present invention monitors swimming pool and/or spa chemistry at all times and instructs owners what chemicals to add and when the pool chemicals are needed. In an embodiment, the inventive system may order the necessary pool chemicals as required. With the present invention, there is no need to guess at what pool products correspond to pool equipment, and no need to remember model numbers. The inventive device orders the correct pool products, which gives pool and spa owners freedom and peace of mind.

In various embodiments, a device, and method of using the device, for monitoring swimming pool chemistry. The device and can comprise sensor(s), network connectivity, knowledge of device's location, circuitry, water proof housing, impact resistant housing, remote proprietary chemistry algorithms, mobile and web applications, messaging capability, and sales and delivery platforms. The device can also use integrated computer application(s) for water monitoring, water chemistry management, energy management, and water cleaning and chemistry correction. The sensor can detect water chemistry and communicate with a network and mobile device(s) to manage pool maintenance. The sensor can have the ability to order water maintenance products and instruct on water maintenance.

Figure 1:
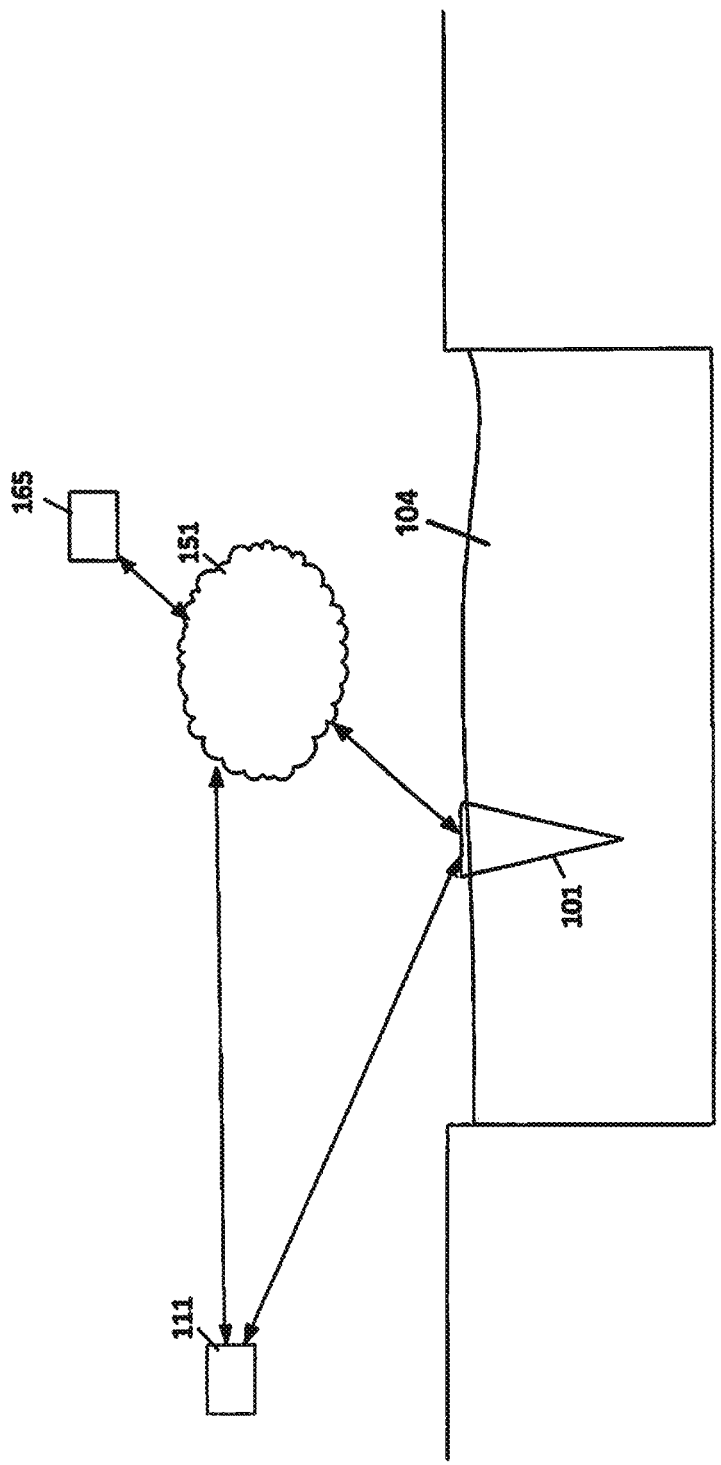
FIG. 1 illustrates a block diagram of an embodiment of water monitoring system components with a floating water monitoring unit.

The present invention is a device and method of using the device for monitoring and maintaining water. The device may contain an integrated computer application solution for water monitoring, water chemistry management, and water cleaning and chemistry correction. With reference to FIG. 1, a water monitoring system can include: a water monitor unit 101, a computing device 111, a network 151 and a server 165. The water monitoring unit 101 can be placed in a body of water 104 to monitor the water quality and chemicals within the water. In the illustrated embodiment, the body of water can be a pool or a spa and the water monitoring unit 101 can float and drift with the current within pool or spa. The water monitoring unit 101 can communicate with the computing device 111 which can be a computer, a tablet computer, a smart phone or any other suitable computing device. In an embodiment, the water monitoring unit 101 can communicate with the computing device 111 through a wireless network 151 such as a WIFI network.

The computing device 111 can run an application program, which can provide a user interface which can provide information to a pool owner or maintenance person. The system may also communicate with a remote server 165 which can provide app software downloads and updates to the computing device 111. The water monitoring unit 101 can also include a processor which runs software, which can be firmware, stored in read only memory coupled to the processor. In an embodiment, the firmware can be updated using any known update method.

Figure 2:
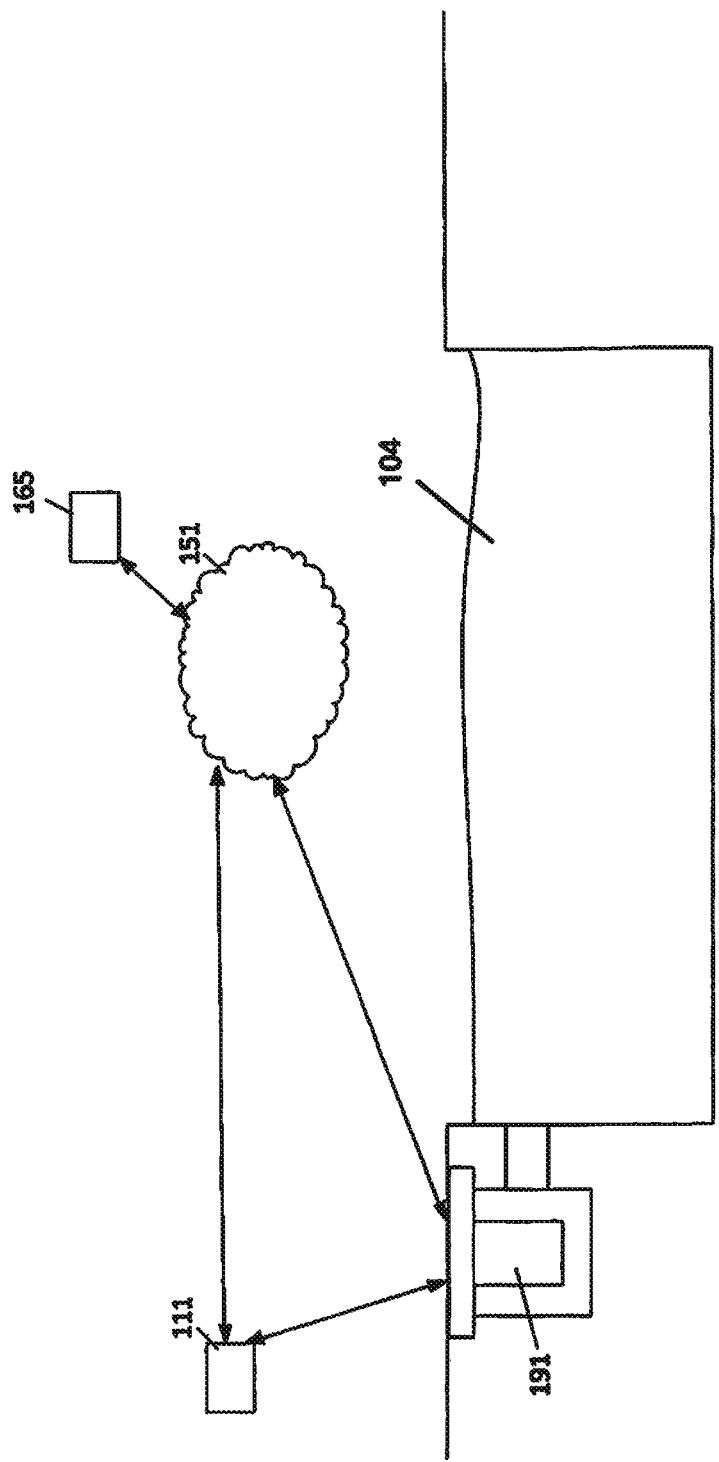
FIG. 2 illustrates a block diagram of an embodiment of water monitoring system components with an integrated monitoring unit.

With reference to FIG. 2, in an embodiment, the water monitoring unit 191 can be integrated into the pool 104. In the illustrated embodiment, the water monitoring unit 191 can be added to a pool skimmer. The pool skimmer can include a removable lid. In an embodiment, the water monitoring unit can be built into a replacement lid which can suspend the water monitoring unit 191 in a recessed volume of circulating pool or spa water.

Figure 3:
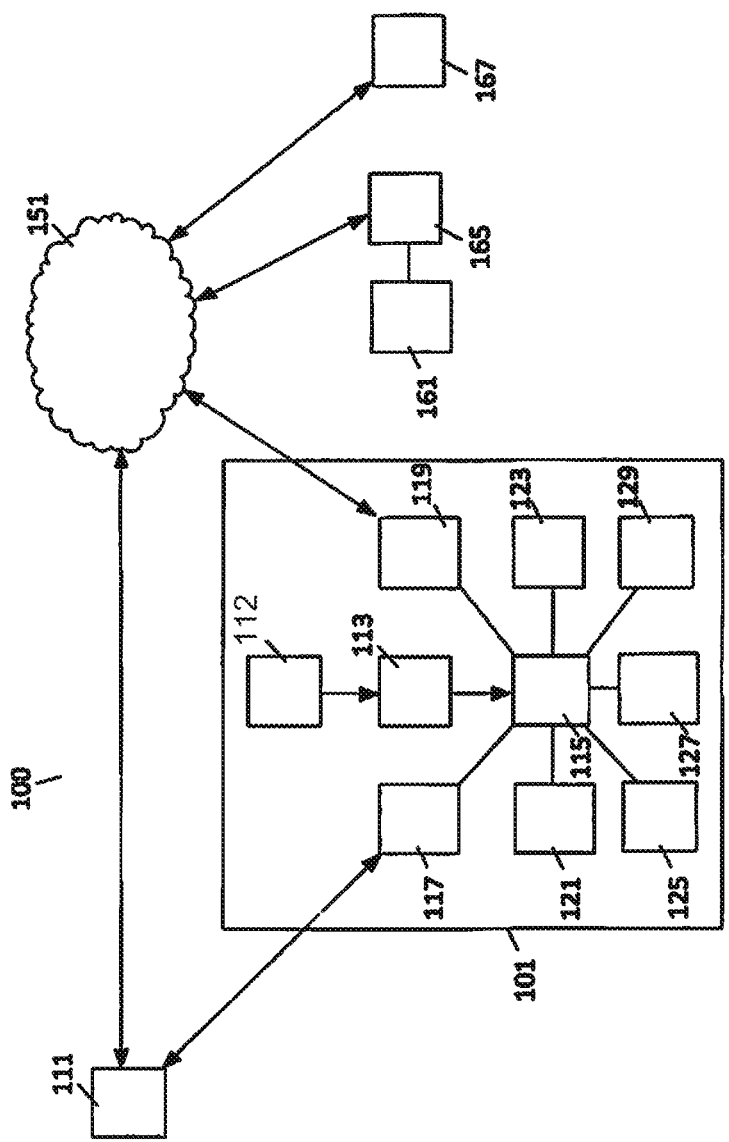
FIG. 3 illustrates a block diagram of an embodiment of the water monitoring unit.

With reference to FIG. 3, a block diagram of an embodiment of the water monitoring system 100 is illustrated. The water monitoring system 100 can include a water monitoring device 101 that can include a solar panel 112 that provides electricity to charge a battery 113 which can provide electricity to the other components of the water monitoring device 101 including a processor 115. The processor 115 can communicate with various sensors including: a pH sensor 121, a temperature (ambient and water) sensor 123, a salinity sensor 125, a depth sensor 127, chemical sensors 129 which can include: Chlorine, Cyanuric Acid, Alkalinity, Bromine, etc. In other embodiments, the sensors may include used with the water monitoring system 100 may include: a total dissolved solids (TDS) sensor and/or an electrical conductivity (EC) Sensor. The processor can obtain measurements from the sensors and then convey this information through transmitters or transceivers. Based on the measurements and the type of chemical sanitizer being used, the processor 115 can make recommendations for adding chemicals to the water and scheduling chemicals for the water to maintain a proper chemical composition.

In another embodiment, the device can include hub-spoke type connectivity. With reference to FIG. 3, an example of this would be a hub, such as a Bluetooth and/or WiFi receiver coupled to a computer 111 which can be a smartphone and/or a server 165, that connects via a wireless network 151 to one or multiple water monitoring devices 101 in a pool 102. This hub could then utilize other connectivity methods such as a computer with WiFi, or a cell phone with 3G, to send data to a cloud or other analytics platform. The hub could be self-contained and run the water analytics "in-house." Another device can access the hub and receive information from the hub and analyze data from multiple water monitoring devices. This data can be stored on a computer 111 or server 165 memory and associated with each individual water monitoring device 101. Information for each of the water monitoring devices 101 can be transmitted back to computers 111 associated with each of the water monitoring devices 101. For example, the server 165 may transmit a first message to a mobile phone computer ill associated with a first water monitoring device 101 that X quantity of chemical A needs to be added to the pool 102 with a note that pools inventory of chemical A is running low. A graphical user interface GUI on the mobile phone computer 111 may include a button asking for authorization to order chemical A from the pool supply store. If the user clicks on the authorization button, the server 165 can transmit a message to a pool supply company 167 to deliver an appropriate quantity of chemical A to the pool 102 associated with the first water monitoring device 101.

In an embodiment, the water monitoring device 101 may include a Wi-Fi or Bluetooth transmitter 117 which can communicate with a local computer 111 which can be a smart phone, computer, server, or any other computer processing device. The water monitoring device 101 may also include a cellular transceiver 119 which can transmit information to a network 111 which can include a cellular network and/or the Internet. In an embodiment, the pool information can be transmitted to a server 165 and the pool information can be stored on a database 161. In an embodiment, the system can be used to run diagnostics on the pool. For example, if a problem is detected the computer 111 or server 165 can request the water monitoring device 101 run chemical testing on demand so that the current chemical measurements can be analyzed. Based on the cumulative pool results for each region, the system can determine local area chemical optimization. For example, hot and humid areas may require more algaecide and colder and less humid regions. This optimization can result in less need for chemical adjustments and more efficient use of pool chemicals which can result in a lower cost for pool maintenance. The system can also be configured to keep track of the chemicals stored at the pool. If the amount of chemicals in storage runs low, the system can be configured to order additional chemicals from a pool chemical supplier 167.

Figure 4:
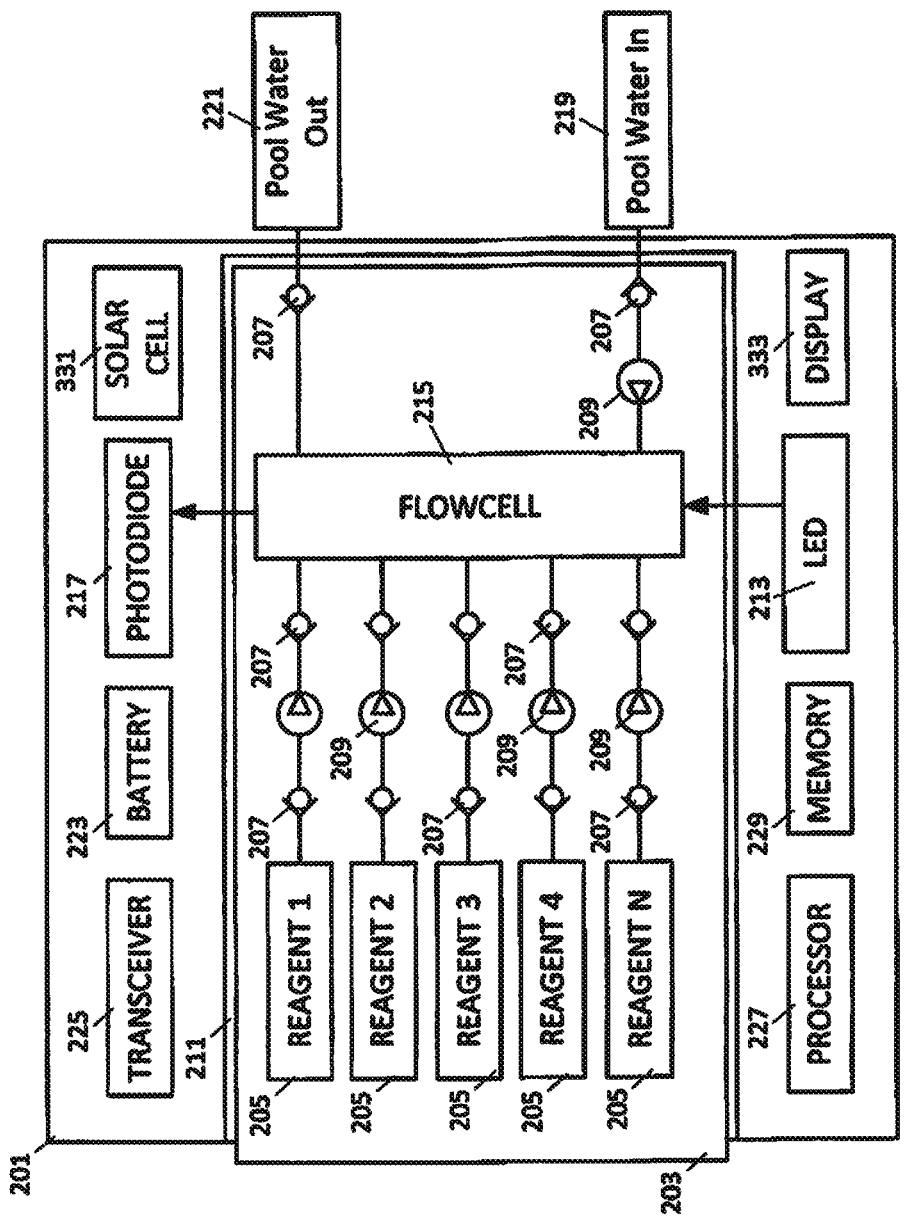
FIG. 4 illustrates a schematic diagram of an embodiment of the water monitoring unit.

In an embodiment with reference to FIG. 4, the present invention can comprise of the following components: A device housing 201, which includes a light 213 which can be a light emitting diode (LED), a light sensor 217 which can be a photodiode and a cartridge receptacle 211. A cartridge fluidic chip 203 can be inserted into the device housing 201. The cartridge can be a consumable cartridge fluidic chip 203 that houses one or more reagents 205. The cartridge fluidic chip 203 can include flow paths, pumps 209 and check valves 207 which can direct the reagents 205 and water into and out of the flowcell 215. The cartridge fluidic chip 203 can also pump pool water from a pool water inlet 219 into the flowcell 215. The reagents 205 can react with the pool water to produce colors based on the chemical reactions of the reagents 205 and the pool water. The light 213 can transmit light through the flowcell 215 which can absorb specific wavelengths of light. The light that passes through the flowcell 215 is detected to by the photodiode light sensor 217. After the testing has been performed, the system can pump the pool water out of the flowcell 215 through a pool water outlet 221. In addition to the described components, the device housing can also include: a processor 227, a transceiver 225 (or transmitter), a battery 223 power supply which can be charged by a solar cell 331, a memory 229 for storing pool water information and a display 333 for displaying status and water information such as water temperature and/or pH level. When any of the reagents 205 are consumed, the cartridge fluidic chip 203 can be replaced with a new unit that includes full reagents 205.

With reference to FIG. 4, an embodiment of the water monitoring unit 201 can include a replaceable cartridge design. The cartridge fluidic chip 203, can be housed in the receptacle 211 of the water monitoring unit 201. The cartridge fluidic chip 203 can provide: reagent storage 205, pumps 209 for pumping of the reagents into the flowcell 215. The cartridge fluidic chip 203 can also include check valves 207 which can control the movement of the water and reagents through the system. More specifically, reagents from the reagent storage 205 and water from the water inlet 219 are pumped into the flowcell 215 where chemical testing is performed. Once the testing is completed, the water and reagent mixture can be pumped out of the water monitoring unit 201 through the pool water outlet 221. In an embodiment, the pumps 209 can be peristaltic, diaphragm, syringe, blister pack or any other suitable chemical pump mechanism. For proper function, the pumps may need to control the fluid volume of 25 µL per pump with an error rate of less than 5%.

The water monitoring unit 201 can include a processor 227, memory 229, a display 333, a battery 223, a transceiver and a solar cell 331. The system components can be powered by electricity from the battery 223 which can be recharged by the solar cell 331 during the day. The processor 227 can be coupled to the memory 229 and control the pumps 209 and the testing performed by the LED 213, flowcell 215 and photodiode 217. The output of the photodiode 217 can be analyzed by the processor 227 to determine the chemicals in the water. The processor 227 can transmit and receive information through the transceiver 225.

In an embodiment, the reagent and water are mixed in the proper predefined ratio and tested by exposing the flowcell 215 to one or more LED 213 lights. Specific wavelengths corresponding to specific colors of light will be absorbed by the reagent and water mixture and the photodiode 217 can detect the absorbed wavelengths of light or more specifically, the photodiode 217 will not receive the absorbed wavelengths of light. The output of the photodiode 217 can be transmitted to a processor 227 which can run software which can identify the concentrations of chemicals in the water based on the absorbed wavelengths of light. In an embodiment, the absorption of light can be based on a total clear absorption 0-1.0 scale where 1.0 is total absorption. In an embodiment, a calibration absorption test can be run with pure water in the flowcell 215 and the light absorption for plain water can be determined by the photodiode 217. Reagent tests can then be run and the differences in the photodiode 217 output signals can be used to determine the chemicals in the water. In an embodiment, the water monitoring unit 201 may sense 440-635 nm wavelengths of light using the AMS (TAOS) TCS34725 as the photodiode 217.

Once the testing is completed the water and reagents are pumped out of the flowcell 215. The flowcell 215 may then be filled with pool water with a pump 209 to remove any residual reagents prior to the next test. Once any of the reagents or other stored chemicals are depleted, the cartridge fluidic chip 203 can be removed and replaced with a new cartridge fluidic chip 203 that is filled with reagents. In different embodiments, the cartridge fluidic chip 203 may be able to pump and mix a series of fluids including reagents, buffer solutions, and titrants in varying sequences. Although FIG. 4 illustrates all reagent storage 205 as reagents any other necessary chemicals can be stored in the reagent storage 205. The expected life of the cartridge can be about eight months or any other reasonable period of time. At the end of this testing period, the cartridge fluidic chip 203 will be replaced by the user.

In an embodiment, the driver pumps 209 can output liquids in 25 µL increments and volume of the flowcell can be approximately 500 µL or any other suitable volume. In an embodiment, the consumable cartridge fluidic chip 203 may accommodate 12 reagents in sufficient volume to allow for 500 tests for approximately 8 months. Note that not the system may perform various types of test each using different reagents on different test schedules. Thus, the cartridge fluidic chip 203 may store different volumes of the reagents based on the test schedule. The flowcell 215 may have a transparent housing that contains the water and reagents but also allows for optical measurements. In an embodiment, the flowcell 215 can be easily cleaned for accurate and repeatable optical testing. Check valves 207 can prevent the fluids from traveling back up the reagent lines.

In different embodiments, different types of driver pumps 209 can be used with the inventive system. For example, in an embodiment, the pumps 209 can include a ball and magnet mechanism. The ball can be placed against a membrane and the ball can be moved within a ball chamber with a magnetic field. The magnetic field can cause the magnetic ball to move against the membrane can increase the volume between two of the check valves 207 which can draw fluid into this space through an inlet check value. When the magnetic field is removed, the membrane can compress the volume and force fluid through the outlet check valve 207. In another embodiment, a piston can be placed against a membrane. The movement of the piston can increase or decrease the volume between check valves 207. Expanding the volume can draw fluid into this space through an inlet check value. When the piston is moved in the opposite direction, the membrane can compress the volume and force fluid through the outlet check valve 207. The piston can be controlled with a threaded rotational mechanism which can be rotated to move the piston linearly. The pump can be cycled by rotating the threaded mechanism a specific number and/or partial number of rotations to accurately control the volume of each pump actuation. In other embodiments, any other suitable pump mechanism can be used with the inventive system.

In an embodiment, several different colorimetric tests can be conducted inside the cartridge. Some of the tests need to be tested more often than others. In an embodiment, the system can be configured to automatically run tests according to the schedules in Table 1 below. The volumes are represented by volume/volume percentages (v/v).

Figure 19:
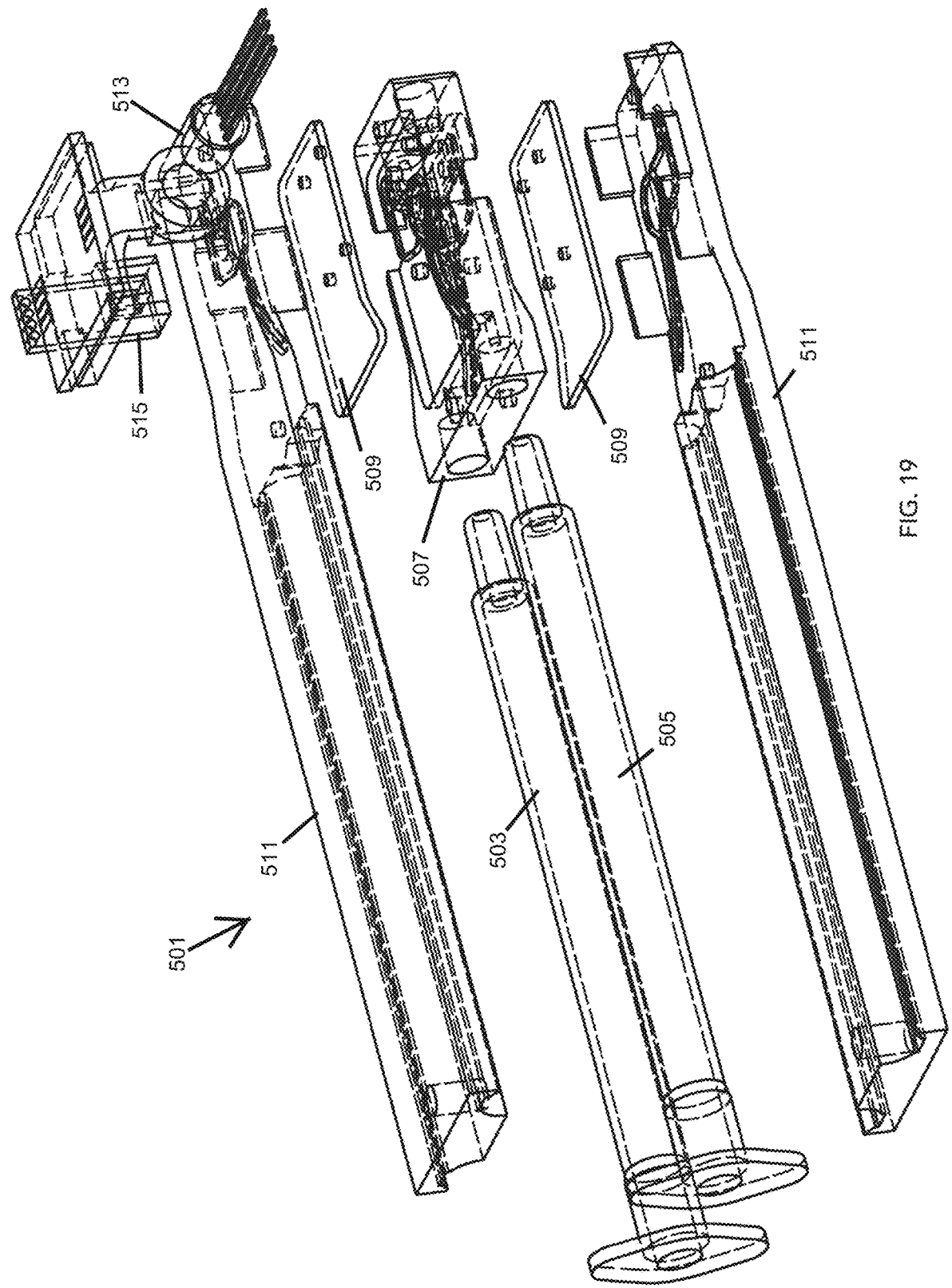
FIG. 19 illustrates an exploded view of an embodiment of a reagent cartridge.

With reference to FIG. 19, an exploded view of an embodiment of a reagent cartridge 501 is illustrated. The reagent cartridge 501 can include a first reagent cylinder 503 and a second reagent cylinder 505, a flowcell 507 and check valves. The first reagent cylinder 503 and the second reagent cylinder 505 can be filled with a first reagent and a second reagent respectively. Planar elastic members 509 can be secured to opposite sides of the flowcell 507.

Figure 21:
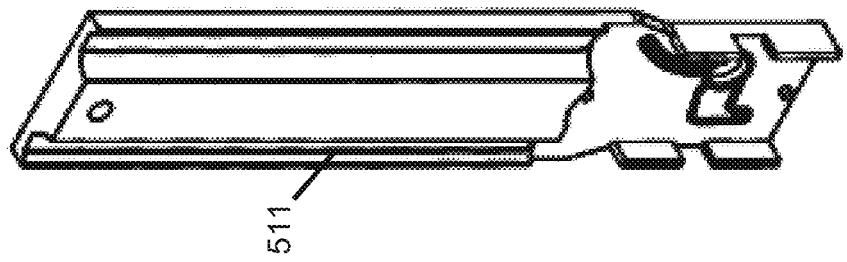
FIG. 21 illustrates a perspective view of a side panel for the flowcell assembly.
Figure 20:
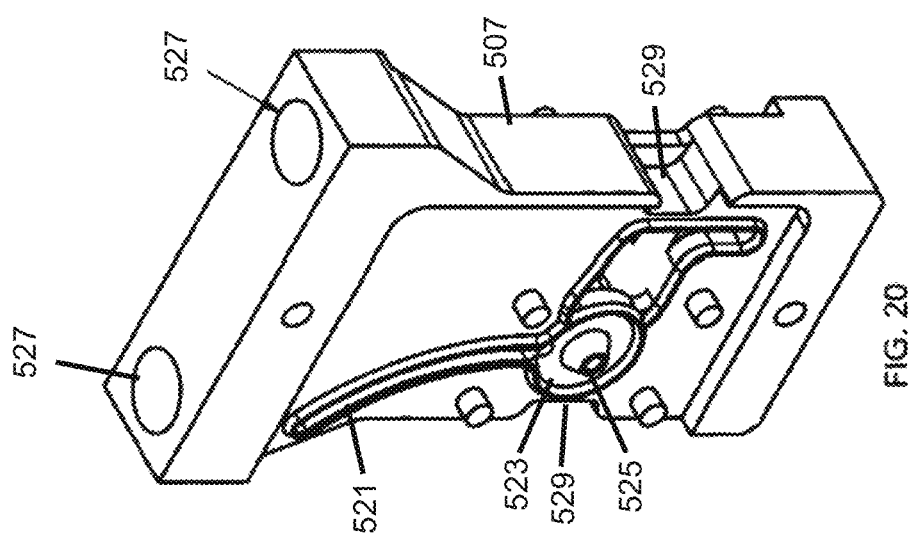
FIG. 20 illustrates a perspective view of a flowcell housing.

With reference to FIG. 20 a perspective view of an embodiment of a flowcell 507 is illustrated. The side surfaces of the flowcell 507 include channels 521 that lead to recessed annular volume 523 with center orifices 525 with raised cylindrical surfaces. The side surfaces of the flowcell 507 are coupled to planar elastic materials (reference number 509 in FIG. 19). The reagents can flow through the channels 521 and fill the recessed annular volume 523. When the plunger moves, the reagent fluid pressure will increase and cause the planar elastic materials (reference number 509 in FIG. 19) to move away from the raised cylindrical surface 525. The reagent will flow from the recessed annular volume 523 inward through the center raised cylindrical surface 525 and into the internal volume of the flowcell 507 where the water sample from the body of water is mixed with the reagent(s). FIG. 21 illustrates an embodiment of a side panel 511 of the reagent cartridge that can be placed against over the planar elastic materials (reference number 509 in FIG. 19).

With reference to FIG. 19, the first reagent cylinder 503 and the second reagent cylinder 505 can be syringes that are filled with a first reagent and a second reagent respectively. Plungers (not shown) can be placed within the first reagent cylinder 503 and the second reagent cylinder 505 to control the flow of the reagents from the cylinders 503, 505. The plungers can be coupled to threaded screws and the rotation of the threaded screws can cause the plungers to be moved through the cylinders 503, 505. The reagents can be incompressible liquids and the movement of the plungers can cause the reagents to be pumped from the cylinders 503, 505. The flowcell housing 507 can have check valves on the side surfaces that include raised annular surfaces which can be covered with planar elastic material structures 509. Pressurization of the reagent liquids can cause the planar elastic material structures 509 to move away from the raised annular on the flowcell housing 507 to open the check valves. When the reagent liquids are not pressurized, the planar elastic material structures 509 to move against the raised annular on the flowcell housing 507 to close the check valves to prevent the backflow of the reagent liquids. A light from a light source 513 can be transmitted through a flowcell

TABLE 1

| Test | Test Schedule | Volume v/v | Chemical and function |
|---|---|---|---|
| pH | 2× per day | 4-20% | Phenol Red reagent |
| Free Chlorine | 2× per day | 4-6% | Free Chlorine Phosphate buffer |
| | | 4-6% | Free Chlorine DPD reagent |
| Total Chlorine | 2× per day | 4-6% | Total Chlorine Phosphate buffer |
| | | 4-6% | Total Chlorine DPD reagent |
| Alkalinity 1 | 1× per 7 days | 4-6% | Phenol Red reagent |
| | | ~0.2% increments | 0.12N Sulfuric Acid Titrant |
| Alkalinity 2 | 1× per 7 days | ~0.4% | Sodium Thiosulfate chlorine neutralizer |
| | | 4-6% | bromocresol green-methyl red indicator |
| | | ~0.2% increments | 0.12N Sulfuric Acid Titrant |
| Cyanuric Acid | 1× per 7 days | 45-55% | Melamine reagent |
| Calcium | 1× per 7 days | ~4% | Calcium Buffer |
| Hardness | | ~1% | Calcium Indicator |
| | | ~0.2% increments | Standard EDTA 0.02N Titrant | in the flowcell housing 507 and the transmitted light can be detected to a light sensor 515. In an embodiment, the light source 513 and the light sensor 515 can be components that are not part of the reagent cartridge 501.

In an embodiment, the reagent cartridge 501 is a replaceable device that is releasably connected to the main water monitoring device. Fluid connections to the cartridge can be made via Luer Slip tapers. The reagents can flow from the cylinders through check valves into the flowcell. The plungers can be coupled to tapered splines that engages the motors to the threaded lead screws inside the cylinders 503, 505 of the cartridge 501.

The reagents can flow from the cylinders 503, 505 through check valves into the flowcell in the flowcell housing 507. With reference to FIG. 20, a perspective view of an embodiment of the flowcell housing 507 is illustrated. The flowcell housing 507 can have reagent inlet holes 527 which can be coupled to the reagent cylinders 503, 505. In an embodiment, the inlet holes 527 can form a liquid tight seal with tapered conical surfaces adjacent to the tip of the reagent cylinders 503, 505. The flowcell housing 507 can have reagent fluid channels 521 which allow the reagents to flow to check valves which include an inner raised circular surface 525 which is surrounded by a recessed annular volume 523 and an outer raised circular surface 529 which surrounds the recessed annular volume 523. As discussed above with reference to FIG. 19, the flowcell housing 507 can be covered with planar elastic materials. Pressurization of the reagent liquids can cause the planar elastic material to move away from the inner raised circular surface 525 on the flowcell housing 507 to open the check valves so that the reagent liquid can flow into the flowcell 529. When the reagent liquids are not pressurized, the planar elastic material can move against the inner raised circular surface 525 on the flowcell housing 507 to close the check valves to prevent the backflow of the reagent liquids out of the flowcell 529. With reference to FIG. 21, a perspective view of an embodiment of the side panel 511.

FIG. 22 illustrates a top view of an embodiment of a syringe pump system 502 and FIG. 23, illustrates a side cross section view of the syringe pump system 502. In the illustrated embodiment, the syringe pump system 501 includes three syringes 531, 533, 535 which can each contain a different test reagent. Each syringe 531, 533, 535 can be operated by advancing a lead screw 557 using a motor 571 to push a plunger 559 forward into the syringe 535 and displace a precise volume of a reagent fluid which is pumped into the flowcell 537. Actuation of the lead screw 557 is typically done using a precise electric rotary actuator motor 571 such as a servo or stepper motor that is rotationally coupled to the lead screw 557 being advanced. A microcontroller sends a signal to the motor 571 with a precise angular distance for the motor output shaft to turn. The motor 571 can be coupled to a center lead screw 557 and the torque forces from the motor 571 drive then center lead screw 557 and the rotational torque force is then passed through the gearing assembly into the tapered spline couplers. The gear rotations can turn tubes 551, 553, 555 which can have a square cross section that pass the torque to the lead screws 557 which spin within captive nuts (within the square tubes) and advances the plungers 559 axially forward into the syringe 531, 533, 535. The forward movement of the lead screws 557 push forward against the plungers 559 in the syringes 531, 533, 535 which dispense the reagent chemicals from the syringes. The movements of the plungers 559 are based on the lead screw 557 thread pattern. A lead screw 557 having 10 threads per inch will move 0.1 inch per rotation of the lead screw 557.

Various water sample testing processes using reagents have been described. When each test is complete, the flowcell 537 can be cleaned by pumping clean water stored in a clean water reservoir 539 which can be pumped into an inlet 581 of the flowcell 537. The prior water sample and reagents can be expelled through an outlet 583. The clean water can also be expelled through the outlet 583 so that the flowcell 537 is clean for the next water sample is tested. In other embodiments, it is possible to pump water directly from the test body of water through the flowcell 537 to remove the prior test water sample and reagents.

The present invention increases the syringe pump efficiency and reduces system cost by using mechanical gearing to drive multiple syringe pumps simultaneously. A precise ratio of fluids dispensed can be reliably achieved by selecting an appropriate gear ratio and lead screw pitch. In an embodiment, a gearing assembly that can drive three syringe pumps are coupled to a single stepper motor. A microcontroller sends a signal to the stepper motor to move a number of steps determined by the previously calculated steps/mm value. Using a set of gears with a ratio of 1:1, the three lead screws in the three syringe pumps are driven simultaneously by the stepper motor to dispense three chemicals (listed in table A) for three individual colorimetric tests. At the end of each syringe is a check-valve that prevents excess reagent from entering a mixing chamber made of chemically inert, optically transparent material where the reagents are mixed with the water sample using a magnetically captured steel stir ball. The steel ball can be moved within the mixing chamber by manipulating the magnetic field and the movement of the steel ball can cause the chemicals to thoroughly mix with the sample fluid which can be pool water.

Figure 24:
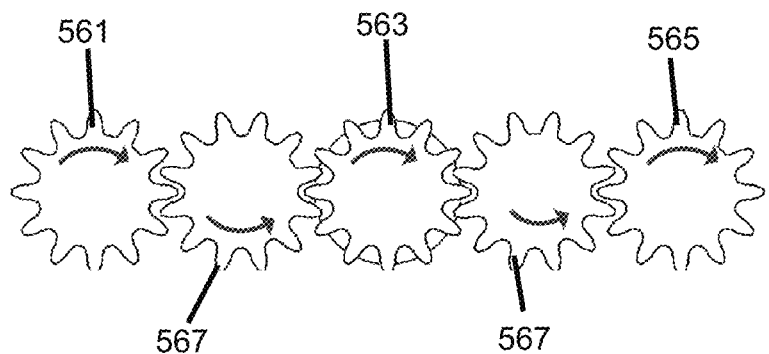
FIG. 24 illustrates a front view of an embodiment of the gears used to drive a plunger assembly.
Figure 25:
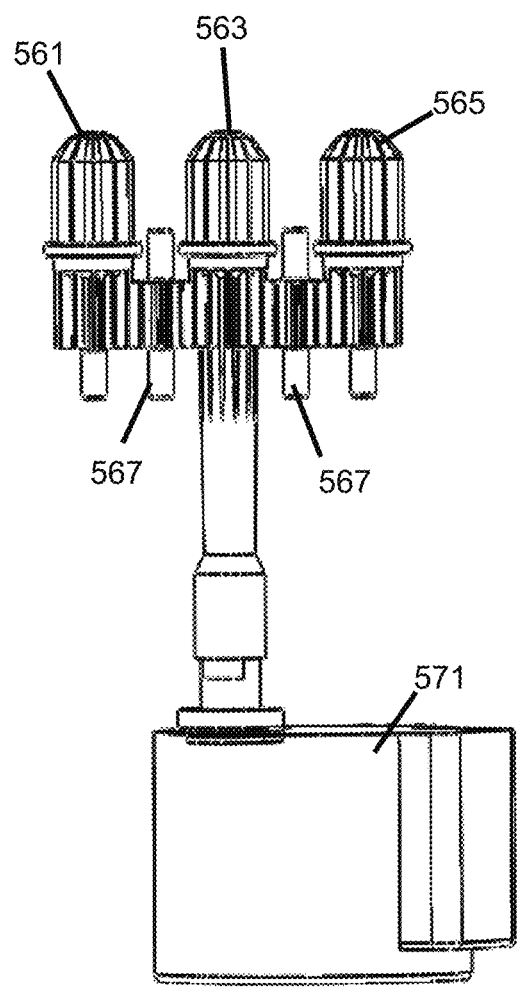
FIG. 25 illustrates a top view of an embodiment of the gears used to drive a plunger assembly.

In a first configuration, all three syringe pumps dispense the same amount, 8.6 of chemicals into a mixing chamber. This 8.6 uL volume can be mixed with a sample of water to create a chemical reaction in the fluid sample with a volume of 172 µL. FIG. 24 illustrates a front view of an embodiment of the gears 561, 563,565, 567 used to drive the plungers in the three syringes. FIG. 25 illustrates a top view of an embodiment of a motor 571 and gears 561, 563,565, 567 used to drive the three syringes. In this example, a first syringe can be driven by gear 561, a second syringe can be driven by gear 563 and a third syringe can be driven by gear 565. The stepper motor 571 can be coupled to gear 563 and there can be intermediate gears 567 between gear 263 and gears 561 and 565. In this example, the intermediate gears 567 and the gears 561, 563,565 all have the same number of teeth, 12 teeth in this example. Thus, a single clockwise rotation of gear 563 will result in a single clockwise rotation of gears 561 and 565 and a single counter clockwise rotation of the intermediate gears 567.

Once the reagents and sample have been thoroughly mixed, a light source such as a light emitting diode (LED) is illuminated and light from the LED is directed through the fluid test sample. A color light sensor on the opposite side of the mixing chamber from the LED can measure the amount of light that is transmitted through the fluid text sample at one or more predetermined wavelengths. The specific wavelengths being measured can dependent upon the analyte being tested. Different analytes will have different light wavelength absorption characteristics. Chemical concentrations for the fluid test samples can be determined by measuring the light wavelengths absorbed by the reagent/sample mixture.

As discussed, in an embodiment, the three syringe pumps are coupled to a single stepper motor. However, rather than configuring all three syringe pumps to emit the same volumes (8.6 uL), the syringe pump system can use a set of gears with different number of teeth and different gear ratios. For example, the stepper motor may rotate one syringe lead screw directly while the other syringe lead screws may have gearing ratios of 1:2 and 2:3. Thus, the three lead screws in the syringe pumps are driven simultaneously by the stepper motor to dispense three chemicals for three separate individual colorimetric tests with volumes of 8.6 uL for the A syringe, 4.3 uL for the B syringe, and 5.67 uL for the C syringe. Applying these gear ratios to the three syringe system can be performed in various different ways. For example, if the output is proportional to the movement of the piston, the gearing can be 6 teeth for gear A, 12 teeth for gear B and 9 teeth for gear C. The intermediate gears can have any number of teeth. One rotation of gear A will result in ½ rotation of gear B and ⅔ rotation of gear C. The different chemical dosage volumes are predetermined depending on the concentration of the reagent being used as well as the reagent-to-sample ratio required by the specific chemical test. The syringe ratios of 1:2 and 2:3 are only examples. By changing the gearing, the syringe pump system can be configured with any other syringe ratios.

It is also possible to change the syringe ratios by altering the geometric configurations of the syringes. For example, in an embodiment, where a greater reagent/sample ratio is needed, a standard 1 mL syringe can be replaced with a 5 mL syringe. This larger syringe can have a larger cross section and the movement of the piston can be altered to adjust for the larger syringe geometry. For example, the larger syringe can have a cross section that is five times greater and the same movement of the syringe piston can deliver five times the fluid volume. This change can allow the system to store more reagent within the cartridge. This can be used to make the number of tests contained in a cartridge the same for all chemistry tests regardless of reagent/sample ratio.

In another embodiment, the motor which drives the syringe pump lead screw can be mounted to an indexing actuator such as a servo, this would allow a single motor to selectively actuate individual syringe pumps using the same gear system described above. Gear arrangements can include configurations where all pumps are actuated independently while other configurations can have certain syringe pumps coupled together with idler gears while other chemicals that require actuation at different times during the testing process can be driven by a separate set of gears not linked to the other syringe pumps.

The syringe pump and light wavelength absorption sensing systems described above can be expanded to conduct as many tests as required by the user. Any combination of the testable parameters listed in Table 2 can be performed using the measurement system. This chemical measurement system can be packaged as a self-contained, battery powered unit housed in a waterproof enclosure that can be deployed directly into the body of water to be measured for instance a residential pool, commercial pool, agricultural water storage tank, or commercial fishery. The unit can use WIFI, Bluetooth, LoRa, GSM, or other applicable wireless technology to publish measurement data to a centralized repository (cloud).

TABLE 2

List of measurable parameters in water and chemicals used in the test

| Analyte/Contaminant | Reagent 1 | Reagent 2 |
|---|---|---|
| Calcium Hardness (Total) | Eriochrome Black T indicator | disodium ethylenediamine tetraacetate (Na EDTA) |
| Chloride (Cl- mg/L) | Ferric ammonium sulfate and HNO3 solution | Saturated Mercuric Thiocyanate |
| Chloride (Cl- mg/L) | Diphenylcarbazone mixed indicator | Mercuric Nitrate Titrant |
| Chloride (Cl- mg/L) | Potassium chromate indicator | silver nitrate titrant |
| Free chlorine (Cl2 mg/L) | Phosphate buffer | DPD |
| Free chlorine (Cl2 mg/L) | Syringaldazine (FACTS) | None |
| Free chlorine (Cl2 mg/L) | Phosphate buffer | DPD (FAS) |
| Total chlorine (Cl2 mg/L) | Phosphate buffer | DPD |
| Total chlorine (Cl2 mg/L) | Phosphate buffer | DPD (FAS) |
| Copper | Bathocuproine | |
| Copper | Neocuproine | |
| Silica | Molybdate | 1-amino-2-naphthol-4-sulfonic acid |
| Phosphate | Antimony potassium tartrate Ammonium molybdate tetrahydrate Sulfuric acid | D-Isoascorbic acid Sucrose |
| Ammonia (NH3) | salicylate-hypochlorite | 3 reagents |
| Nitrate (NO3) | Diazotizationicoupling | |
| Nitrite (NO2) | Zinc reduction | |

In an embodiment, the reagent cartridges can have planar elastic materials attached to opposite sides of the flowcell. FIG. 19 illustrates a more detailed view of a reagent cartridge assembly. The side surfaces of the flowcell include channels that lead to recessed annular volume with center orifices with a raised cylindrical surface. The side surfaces of the flowcell are coupled to planar elastic materials. The reagents can fill the recessed annular volume. When the plunger moves, the reagent will increase the incompressible reagent fluid pressure which will cause the planar elastic materials to move away from the raised cylindrical surface. The reagent will flow from the recessed annular volume inward through the center raised cylindrical surface and into the flowcell where the pool water is mixed with the reagent(s). FIG. 21 illustrates an embodiment of a side panel of the reagent cartridge.

To conduct a water test, a fresh sample is pumped into the flowcell via the pool inlet connection. Once the flowcell is filled with a fresh water sample the LED is lit in red, green, and blue colors to establish a baseline reading. The intensities of light in the red, green, and blue parts of the visible spectrum that passes through the flowcell are detected. The intensities of light for each color are measured by a color sensor located on the opposite side of the cartridge. The sensors can detect the wavelengths of light that are absorbed by the mixture. After the baseline reading has been taken, a motor turns the reagent lead screw to advance the plunger in a syringe by a predetermined distance. This forces a volume of reagent through the flowcell check-valve and into the flowcell. A servo-mounted magnetic lever actuates a steel ball inside of the flowcell to facilitate mixing of the sample and reagent. The reagent(s) are mixed with the water and the mixture is exposed to light and light sensors detect the light transmitted through the mixture. The LED is lit in red, green, and blue once more. The intensities of light getting through the flowcell are measured and the differences in intensity between the clear sample and the sample/reagent mixture, known as the absorption, are matched against a database of absorption values for known. The water pump is then run again to flush out the water/reagent mixture and leave the flowcell filled with clean water until the next test. Different reagents can be used for different chemical water content testing including: pH, free chlorine, free bromine, total alkalinity, cyanuric acid, calcium hardness, etc.

In different embodiments, the chemical testing performed by the inventive system can be described in a processing method.

1. Draw water sample for testing into the flowcell. In an embodiment, running a water inlet pump can perform the water drawings.
2. Take an initial light absorption reading of the sample. In an embodiment, the light can be illuminated and the light can be transmitted through the water sample in the flowcell. The light that is transmitted through the water sample in the flowcell is detected by a light sensor that detects the initial light absorption reading of the water sample. The light sensor does not detect reflected or light fluorescence from the water sample.
3. Dispense the analyte detecting reagent, such as bromocresol green/methyl red blended indicator, and any other reagent such as buffers, chlorine neutralizers, etc. In an embodiment, the dispensing of the analyte detecting reagent is performed by moving the plunger within the syringe as described above.
4. Mix the sample and reagent(s) in the flowcell. In an embodiment, the flowcell can have a mixing mechanism. This can be an internal mixing device such as an agitator or a mechanism that can move the flowcell to promote proper mixing of the water with the reagent(s).
5. Take a light absorption reading of the mixture of reagents by illuminating the light source and measuring the transmitted through the water sample and reagent mixture with a light sensor.
6. Dispense a set volume and concentration of the titrant into the flowcell. The titrant being any chemical that affects the composition of the sample such as acid or base in a pH titration or EDTA in a titration forming complexes with calcium or magnesium ions.
7. Mix the sample and titrant volume(s) in the flowcell
8. Take a light absorption reading
9. Compare the light absorption from #8 to absorption in step #5
10. Repeat steps #6 through #9 until the endpoint is reached. The endpoint is reached when the sample color changes, such as from green to red or from pink to blue. The endpoint is detected by an abrupt change in light absorption of the sample reagent mixture, usually >0.1, after a titrant volume is dispensed.
11. An additional cycle from #6 through #9 may be taken in order to determine if the final endpoint was reached. If the absorption change is not approximately zero, the cycle is repeated.
12. Once the light absorption change of the sample reagent mixture is approximately zero, the device may send the absorption values as well as how much titrant was dispensed into the flowcell.
13. The flowcell is then flushed with fresh water to prepare for the next test.

pH Testing

Figure 30:
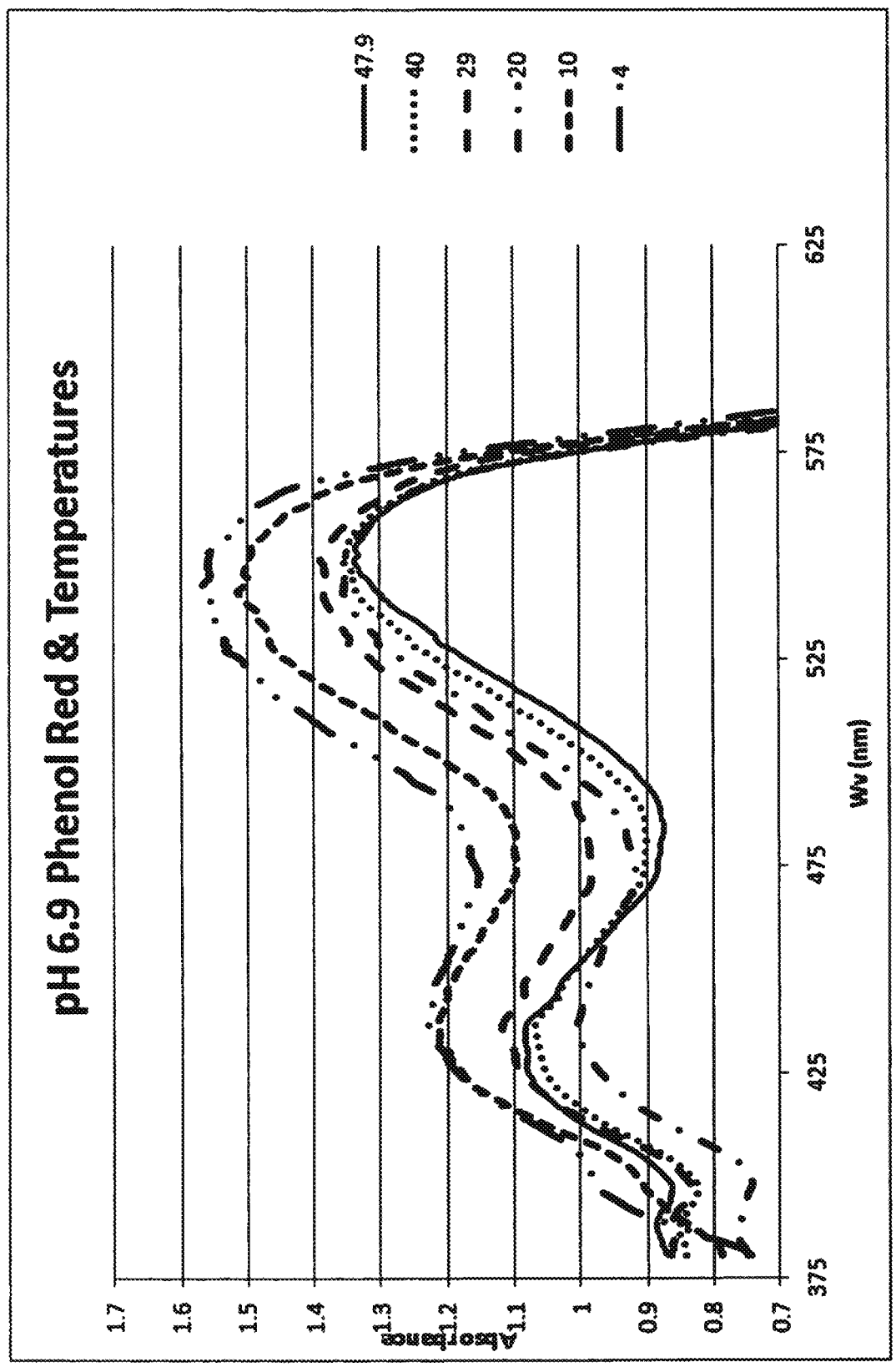
FIG. 30 illustrates a pH standard vs. a blue-green ratio calibration which shows the curve used by the device to determine the pH from the absorption measured.
Figure 31:
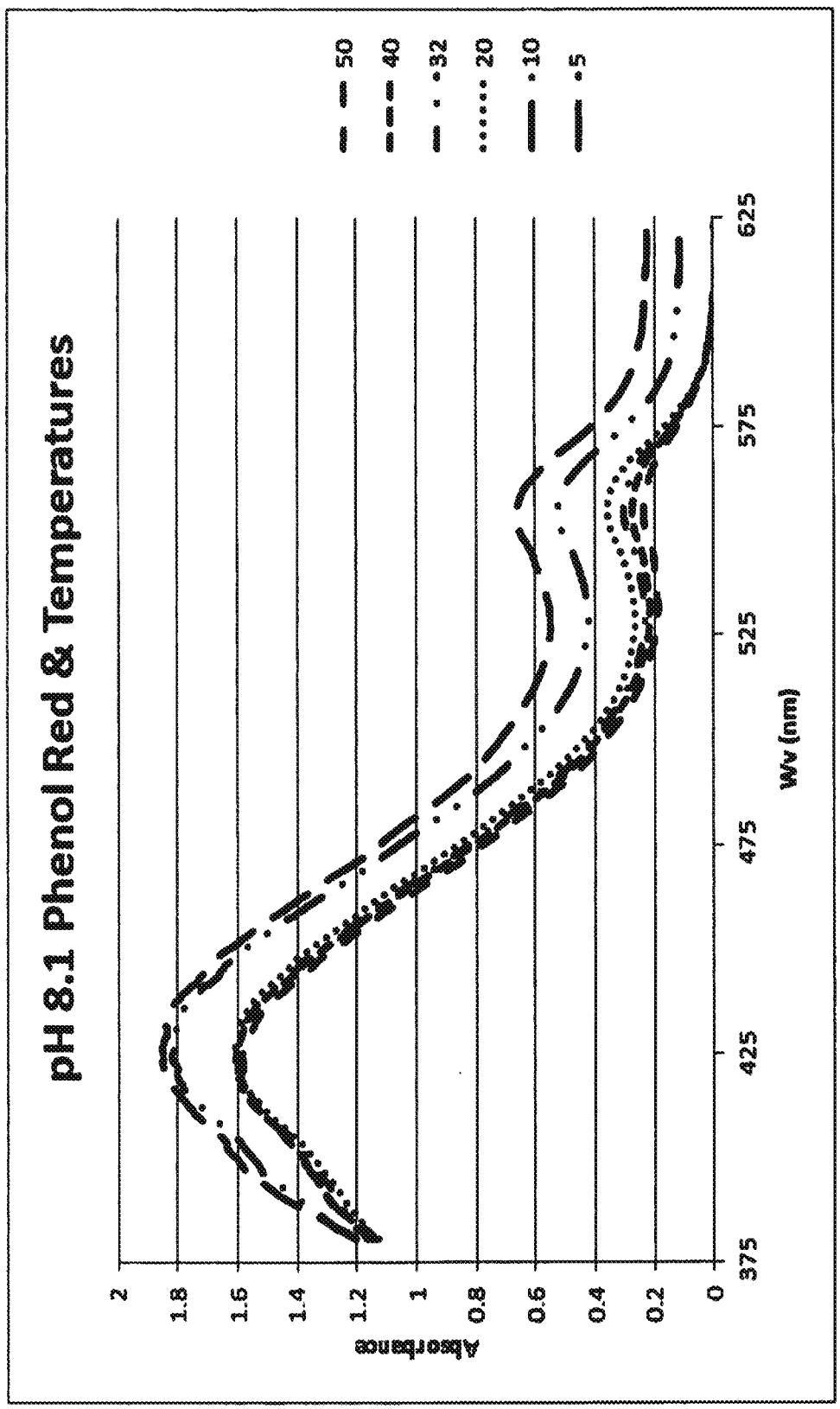
FIG. 31 illustrates the phenol red absorbance for pH 8.1 at various temperatures.
Figure 32:
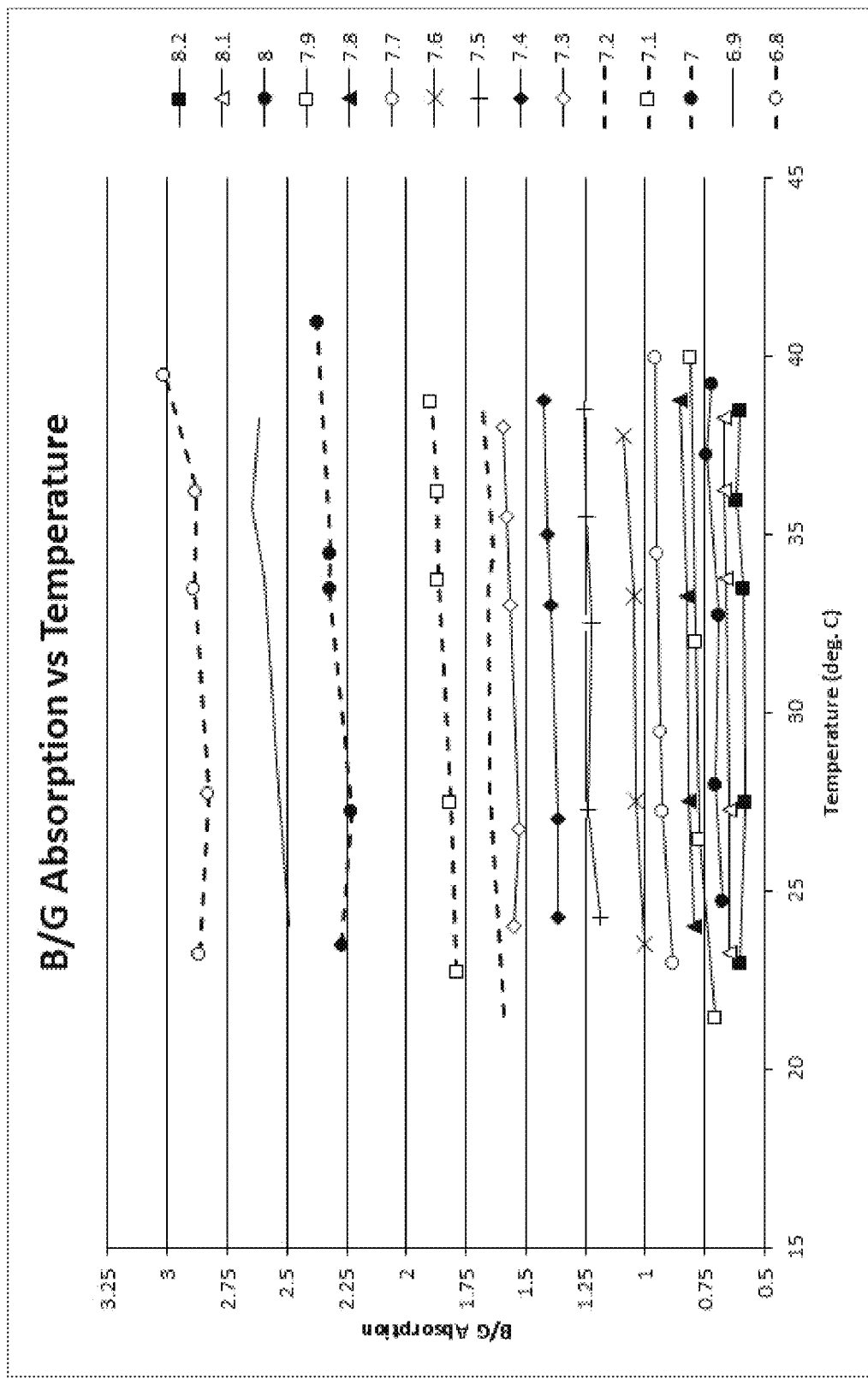
FIG. 32 illustrates the blue-green absorption ratio for the pH range from 6.8 to 8.2 and temperatures from 21.5 to 40 degrees Celsius.

The pH is determined using the pH indicator phenol red (phenolsulfonphthalein) with sodium thiosulfate added as a chlorine neutralizer. The absorption is measured at two points that are related to the pH of the solution. The absorption spectrum of phenol red is temperature dependent as shown in FIGS. 30 and 31 at pH 6.9 and 8.1 respectively. In FIG. 32 a graph of light absorption at wavelengths of light between 375 nm and 580 nm is illustrated. The phenol red absorbance for pH 6.9 is variable depending upon the sample temperatures in degrees Celsius. At cooler temperatures the absorption rate is higher and at higher temperatures the absorption rate is lower. In this example, at 560 nm wavelength, the 47.9 degree C. sample absorption can be about 1.3 while the 4 degree C. sample absorption can be about 1.5. In FIG. 31 the phenol red absorbance for pH 8.1 at various temperatures in degrees Celsius is illustrated. In this, at 440 nm wavelength, the 50 degree C. sample absorption can be about 1.2 while the 5 degree C. sample absorption can be about 1.6.

In order to reduce the interference of temperature, the ratio between blue and green absorption is determined at or near the peak wavelengths for the pH indicator. The phenol red peak wavelengths are 440 and 560 nm. FIG. 32 illustrates the blue-green absorption ratio for the pH range from 6.8 to 8.2 and temperatures from 21.5 to 40 degrees Celsius. In these examples, the blue-green absorption increases with temperature. In an embodiment, the inventive system can determine the temperatures of the test samples and apply correction factors to the light absorptions levels to adjust for the sample temperatures.

Figure 33:
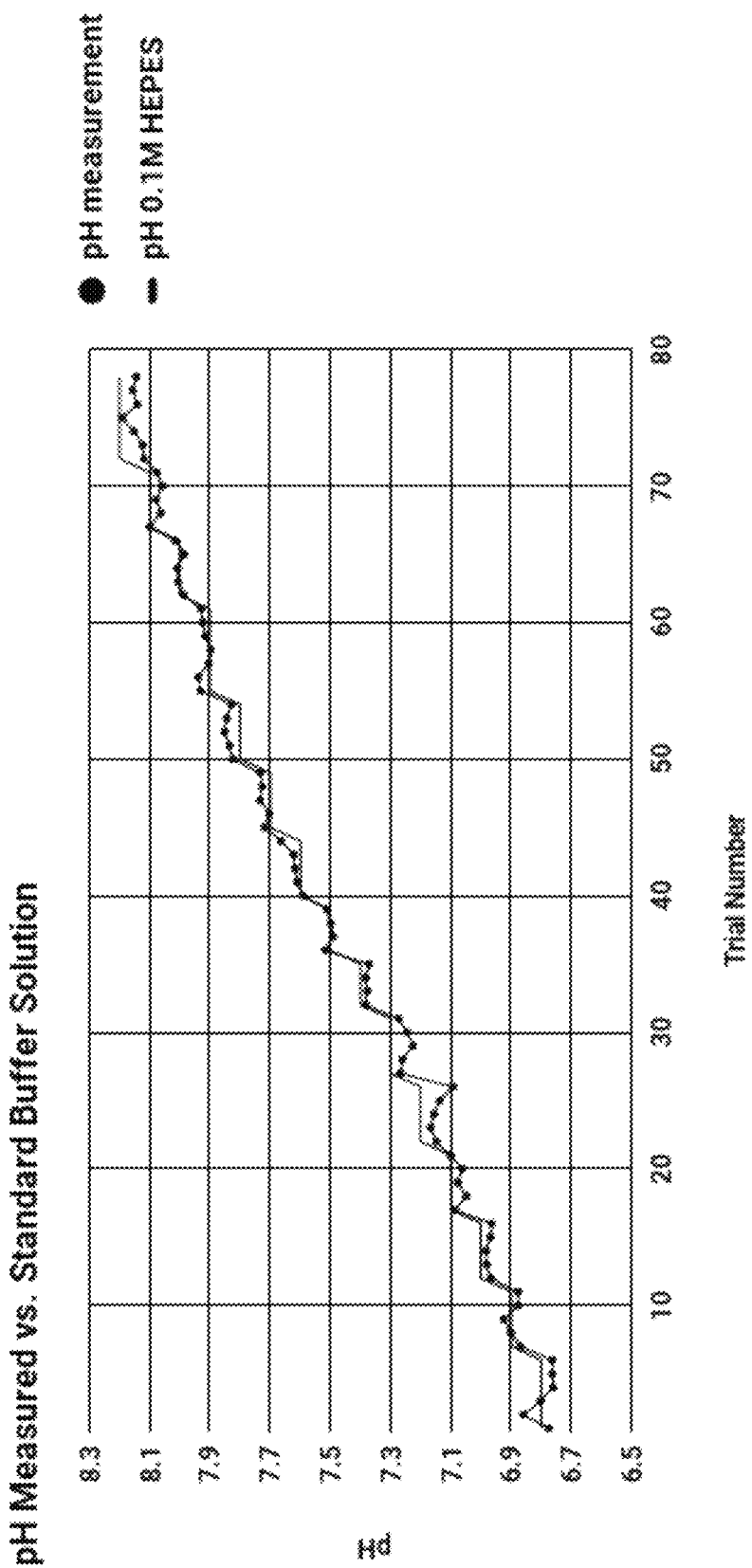
FIG. 33 illustrates a graph of pH measured vs. standard buffer solution.
Figure 34:
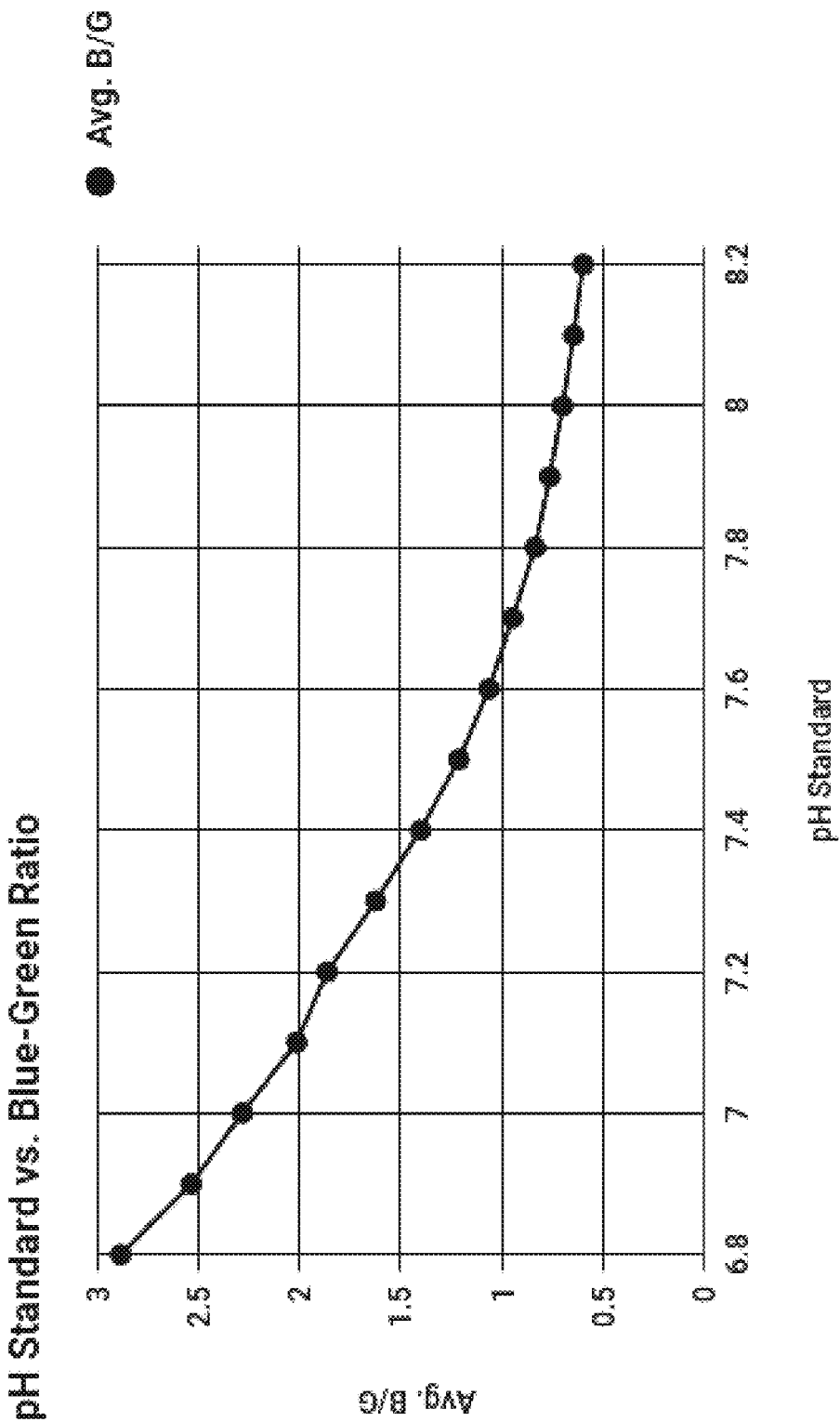
FIG. 34 illustrates a pH standard vs. a blue-green ratio calibration, which shows the curve used by the device to determine the pH from the absorption measured.

FIG. 33 illustrates a graph of pH measured vs. standard buffer solution. The blue-green absorption was measured against 0.1M pH standards prepared from 1M HEPES buffers supplied by Hampton Research. The pH of each buffer was determined by the method described herein. FIG. 34 illustrates a pH standard vs. a blue-green ratio calibration which shows the curve used by the device to determine the pH from the absorption measured. The results illustrate the pH measured using blue-green absorption vs. pH standard HEPES buffer, the method was able to determine the pH of the buffer to within approximately 0.1 pH unit.

In another embodiment, the testing procedures performed by the water monitoring unit can depend upon the type of testing being performed. For example, with reference to FIG. 5, for pH testing, the water monitoring unit can automatically add the designated reagent to the water 351 in the flowcell. In a preferred embodiment, the volume of water is repeatable with an accuracy of + or −1%. The pool water in the flowcell can then be tested. The water can be exposed to light from the LED and the transmitted light can be detected by the photodiode. This initial test can determine the light absorption of the pool water prior to adding test chemicals 352. The reagent can then be added to the flowcell and mixed with the water 354. As discussed, the reagent can be phenol red and the volume can be 5% v/v. In other embodiments, any other suitable reagent and volume can be used for testing. The flowcell can include a mixing mechanism such as an agitator which actively mixes the water and reagent. The mixed reagent and water can then be tested 355 for light wavelength absorption. In some embodiments, the total light absorption can be measured and in other embodiments, the light absorption for one or more light wavelength frequencies can be measured. The results of the test can be used to determine the pH level of the pool water. Once testing is complete, the flowcell can be flushed with fresh pool water to remove the reagent from the flowcell 356.

As discussed above, during testing the chemicals mixed with the water can be exposed to light. Some wavelengths of light will be absorbed by the water and the photodiode can be used to measure these absorbed wavelengths. The light absorption test data can be analyzed in different ways depending on the testing being performed. For example, the pH test can include mixing the reagent phenol red with the water and the absorbed wavelengths are measured with the photodiode. Phenol red exists as a red crystal that is stable in air. Its solubility is 0.77 grams per liter (g/l) in water and 2.9 g/l in ethanol. It is a weak acid with pKa=8.00 at 20° C. (68° F.). A solution of phenol red is used as a pH indicator and the water reagent mixture can exhibit a gradual color transition from yellow to red over the pH range 6.8 to 8.2. Above pH 8.2, phenol red turns a bright pink (fuchsia) color.

Figure 11:
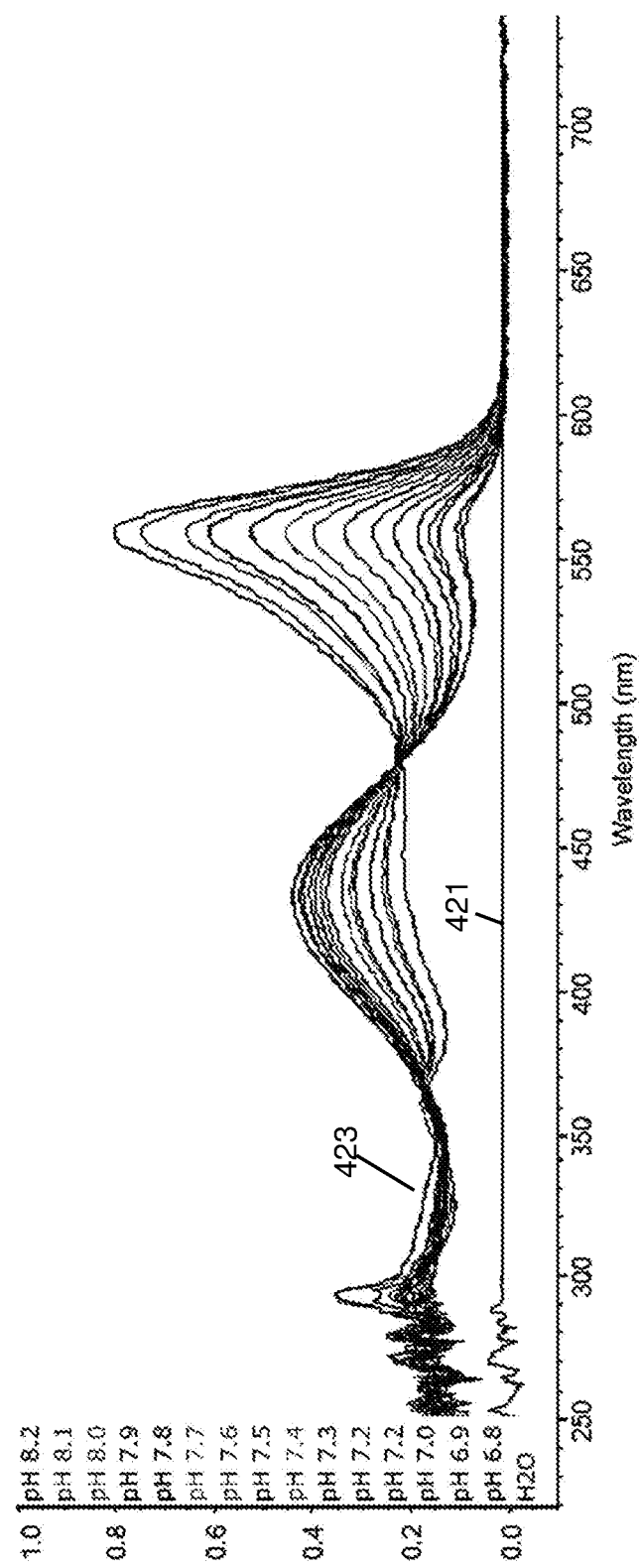
FIG. 11 illustrates a graph for light absorption for different wavelengths of light for phenol red.

With reference to FIG. 11 a graph illustrating the light absorption of the water is illustrated. The lower straight lower line between 330 nm and 700 nm wavelength light can represent the optical absorption of pure water. The curved lines can represent the different light absorptions for different pH levels of water across the 330 and 700 nm wavelength light spectrum. Measuring the absorption at two wavelengths can provide a method for measuring the pH level of the water. In an embodiment, the two wavelengths can be measured. A first wavelength can be between 430 nm and 450 nm and a second wavelength can be between 550 nm and 570 nm. In a narrower range, the first wavelength can be between 435 nm and 445 nm and the second wavelength can be between 555 nm and 565 nm. In a narrower wavelength measurement range, the first wavelength can be 440 nm and the second wavelength can be 560 nm. Based on the ratio's these measurements, the accuracy of the measured pH can be within 5%. At 440 nm the light absorption can be inversely proportional to the pH level of the water being tested. Water having a pH level of about 8.2 can have a 440 nm light absorption of about 0.2 and water having a pH level of about 6.8 can have a 440 nm light absorption of about 0.45. At a 560 nm wavelength the light absorption can be proportional to the pH level of the water being tested. Water having a pH level of 8.2 can have an absorption level of about 0.82 and water having a pH level of 6.8 can have an absorption level of about 0.08 of 560 nm wavelength light.

In an embodiment, the ideal pH level is 7.5 and an acceptable pH level is between 7.4-7.6. With reference to FIG. 11, in an embodiment, the pH level of 7.5 corresponds to an absorption of 0.38 at 440 nm and 0.35 at 560 nm. For pH levels lower than 7.5, the absorption at 440 nm will be higher than 0.38 and the absorption at 560 nm will be lower than 0.35. Conversely, for pH levels higher than 7.5, the absorption at 440 nm will be lower than 0.38 and the absorption at 560 nm will be greater than 0.35. In an embodiment, the pH level for the water can be determined by measuring the absorption ratio ($Absorption_{440\ nm}/Absorption_{560\ nm}$) of the 440 nm and 560 nm wavelengths. At a pH of 7.5, the absorption ratio should be 0.38/0.35=1.085. For pH levels below 7.5 the ratio will be less then 1.085 and for pH levels above 7.5 the ratio will be greater than 1.085. As discussed, the pH level of 7.4-7.6 can be acceptable. For a pH level of 7.4, the 440 nm absorption can be about 0.39 and the 560 nm absorption can be about 0.30. For a pH level of 7.6, the 440 nm absorption can be about 0.36 and the 560 nm absorption can be about 0.40. Thus, the 7.4 ratio can be about 0.39/0.30=1.3 and the 7.6 ratio can be about 0.36/0.40=0.9. In an embodiment, the pH level of the water can be determined based on the detected ratio of the absorption levels at multiple wavelengths of light. This process can allow the water monitoring system to be able to accurately measure pH to within 5% accuracy. Because this process uses ratios rather than specific absorption levels, the system can be less prone to calibration errors of the photodiode sensor. In other embodiments, the light absorption algorithms can be used to determine the pH level of the test water. Although the pH reagent has been described as Phenol Red, in other embodiments, various other reagents can be used to measure the pH level including: azolitmin, bromothymol blue, neutral red, cresol red, naphtholphthalein, and any other suitable reagent.

As discussed, the pool can have an optimum pH level of 7.5 and an acceptable range of 7.4 to 7.6. If the pH level is lower than 7.4, the water monitoring system can recommend adding chemicals such as soda ash to increase the pH level. The quantity of the chemicals added can depend upon the volume of the body of water (pool volume). The recommended chemical adjustment can be based on an algorithm or a look up table such as Table 3 below which can be stored in the memory of the system. Similar algorithms and/or tables can be used to instruct users to lower the pH level.

TABLE 3

| pH Level | 5,000 gallon pool | 10,000 gallon pool | 15,000 gallon pool | 20,000 gallon pool |
| --- | --- | --- | --- | --- |
| 7.4 | 1.50 oz. | 3.00 oz. | 4.5 oz. | 6.00 oz. |
| 7.3 | 3.00 oz. | 6.00 oz. | 9.00 oz. | 12.00 oz. |
| 7.2 | 3.50 oz. | 7.00 oz. | 10.5 oz. | 14.00 oz. |
| 7.1 | 4.00 oz. | 8.00 oz. | 12.00 oz. | 16.00 oz. |
| 7.0 | 4.66 oz. | 9.33 oz. | 13.33 oz. | 18.66 oz. |
| 6.9 | 5.33 oz. | 10.66 oz. | 14.66 oz. | 21.33 oz. |
| 6.8 | 6.00 oz. | 12.00 oz. | 16.00 oz. | 24.00 oz. |
| 6.7 | 6.66 oz. | 13.33 oz. | 13.33 oz. | 26.66 oz. |
| 6.6 | 7.33 oz. | 14.66 oz. | 22.00 oz. | 29.33 oz. |

Free Chlorine and Free Bromine Test

Figure 29:
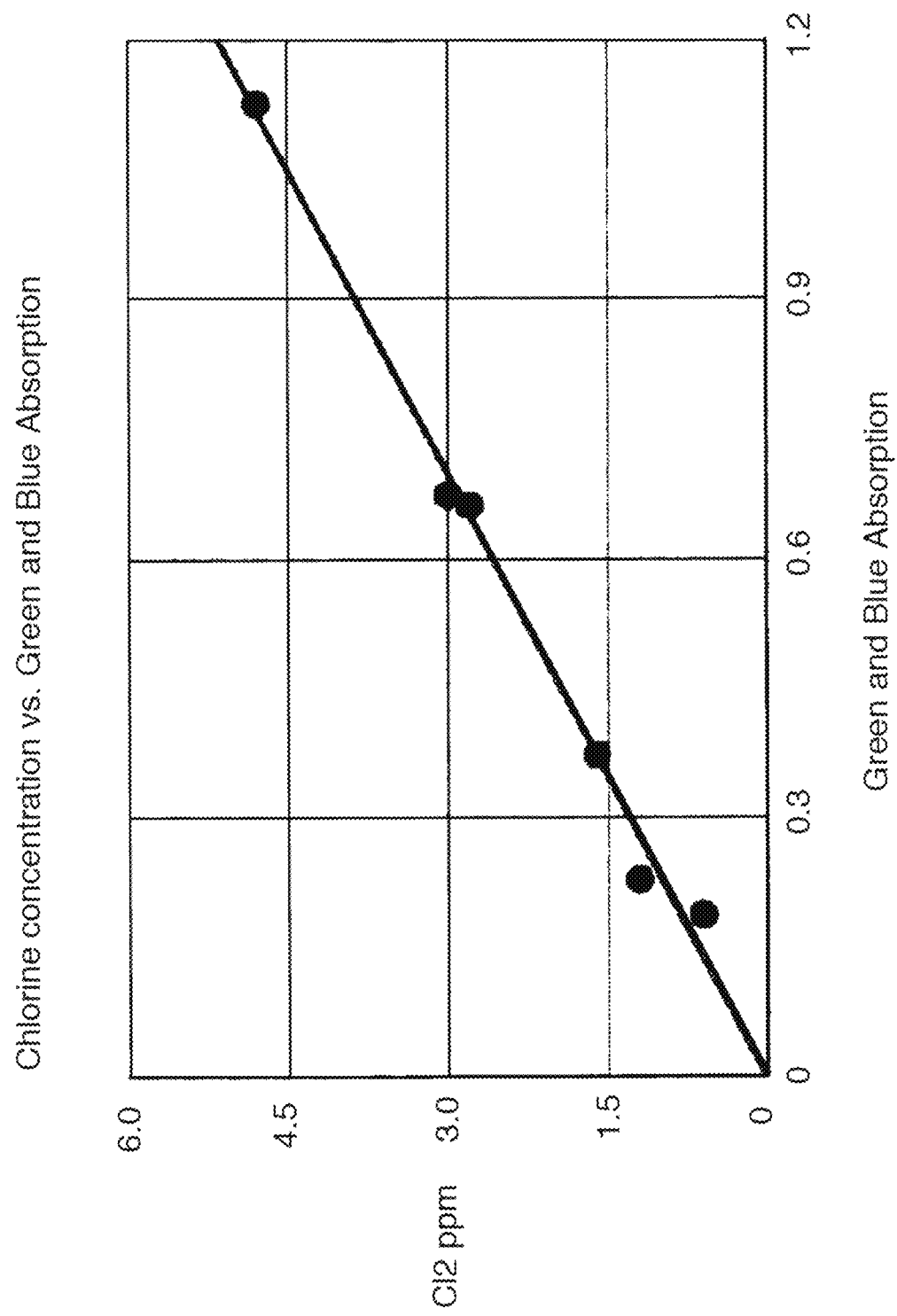
FIG. 29 shows a graph of $CL_2$ ppm in the y-axis v. green and blue light absorption on the x-axis.

The free chlorine and bromine are determined using the DPD (N, N Diethyl-1, 4 Phenylenediamine Sulfate) colorimetric method at near neutral pH. The blue and green absorption is measured in order to determine the chlorine or bromine concentration. FIG. 29 shows the linear region for the blue and green absorption response for $CL_2$ ppm in the y-axis v. green and blue light absorption on the x-axis. Above 5 ppm DPD exhibits a nonlinear response and the color of the solution begins to fade. This limits the detection range currently up to 5 ppm $Cl_2$. The bromine response is approximately two times the chlorine response and exhibits similar characteristics. The green absorption is measured near the saddle point of 530 nm, while the blue absorption is measured near the maxima of 512 nm. By exposing the test samples to light and determining the green and blue absorption of the test samples, the chlorine concentration can be determined for the test samples.

The test procedures for free chlorine are described with reference to FIG. 6. For free chlorine testing, the water may need both a buffer and reagent chemicals. With a test water sample of + or −1%, the free chlorine test can be accurate for + or −0.4 ppm free chlorine. In an embodiment, the monitoring unit can automatically add the designated buffer to the water 361 in the flowcell. The buffer can then be added to the flowcell and mixed with the water 363. In an embodiment, the buffer can be free chlorine phosphate buffer with a volume of 5% v/v. In other embodiments, any other suitable reagent and volume can be used for pH testing. The buffer and water mixture can be tested for base calibration 364 where the buffer and water are exposed to light from the LED and the photodiode detects the transmitted light and determines the absorbed light wavelengths. The reagent can be added and mixed with the buffer and water 365. In an embodiment, the reagent can be free chlorine DPD with a volume of 5% v/v or any other suitable reagent and volume. Testing 367 is then performed to determine the amount of light absorbed by the reacted reagent. In some embodiments, the total light absorption can be measured and in other embodiments, the light absorption for one or more light wavelength frequencies can be measured. Once testing is complete, the flowcell can be flushed with fresh pool water to remove the reagent from the flowcell 368.

Figure 7:
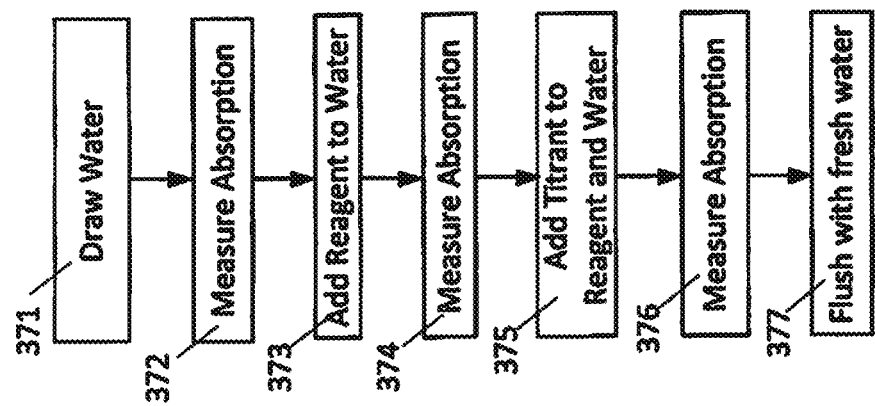
FIG. 7 illustrates a flow chart for an embodiment of alkalinity testing.

The test procedures for total chlorine can also be described with reference to FIG. 7. With a test water sample of + or −1%, the total chlorine test can be accurate within + or −0.4 ppm free chlorine. In an embodiment, the monitoring unit can automatically add the designated buffer to the water 361 in the flowcell. The buffer can then be added to the flowcell and mixed with the water 363. In an embodiment, the buffer can be total chlorine phosphate buffer with a volume of 5% v/v or any other suitable reagent and volume can be used for pH testing. The buffer and water mixture can be tested for base calibration 364 where the buffer and water are exposed to light from the LED and the photodiode detects the transmitted light and determines the absorbed light wavelengths. The reagent can be added and mixed with the buffer and water 365. In an embodiment, the reagent can be total chlorine DPD with a volume of 5% v/v or any other suitable reagent and volume. Testing 367 is then performed to determine the amount of light absorbed by the reacted reagent. In some embodiments, the total light absorption can be measured and in other embodiments, the light absorption for one or more light wavelength frequencies can be measured. Once testing is complete, the flowcell can be flushed with fresh pool water to remove the reagent from the flowcell 368.

Figure 12:
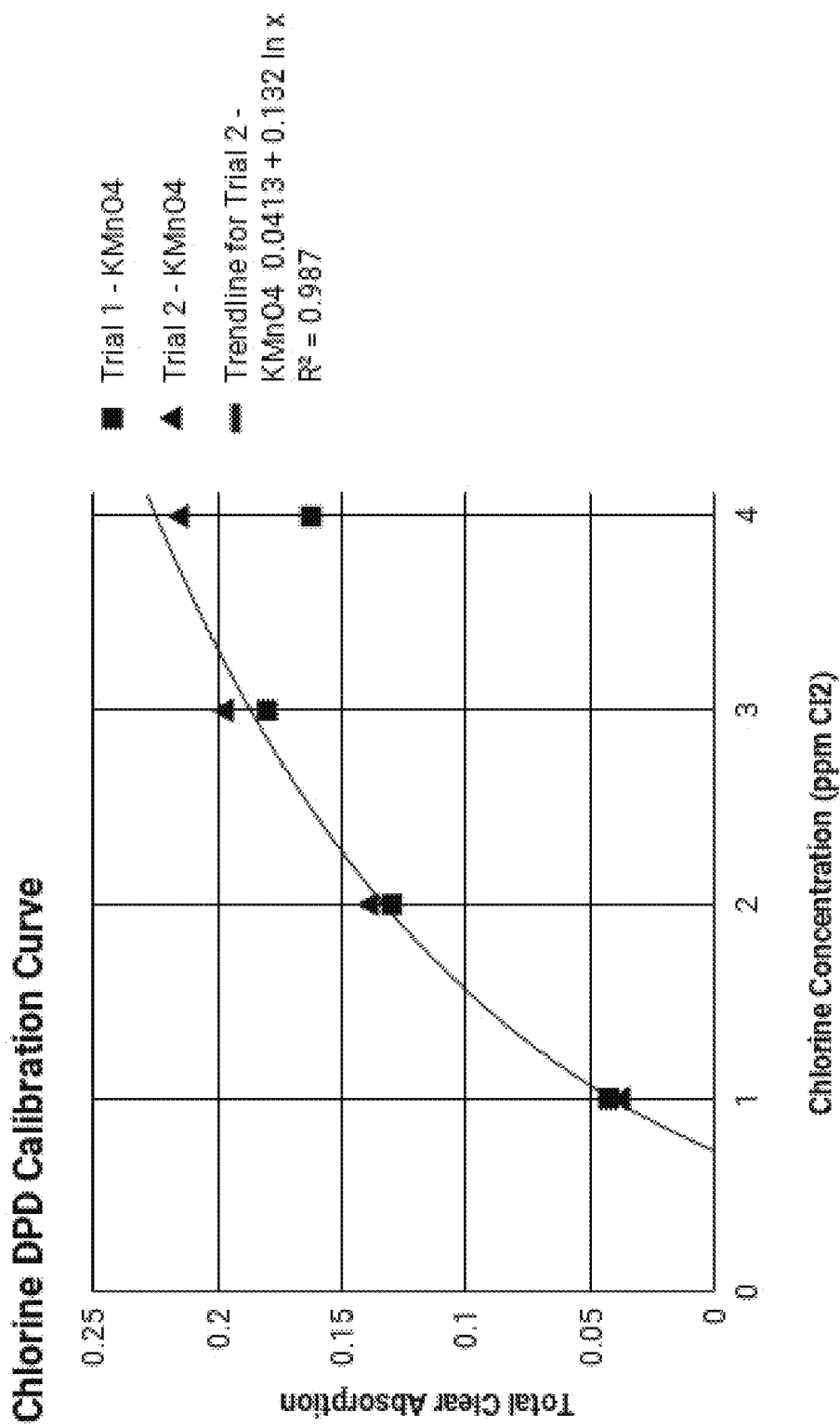
FIG. 12 illustrates a graph for light absorption for chlorine testing.

As discussed above, the chlorine light absorption testing of water that can be mixed with a buffer and reagent. The chlorine concentration in parts per million (ppm) can be determined by preparing the water for chlorine testing with a buffer as described above. This test will be used to calibrate the absorption values that are being read from the TAOS sensor. The actual testing can be performed by exposing the water with reagent to light and measuring the absorption. FIG. 12 illustrates an embodiment of a graph showing a relationship between total clear light absorption and the chlorine concentration of the water. If the chlorine optical test results have a light absorption of about 0.1, the chlorine concentration can be about 1.6 ppm $CL_2$ which can be within the target value of 1.0 to 3.0 ppm. In an embodiment, the graph illustrated in FIG. 12 can be represented by the equation Absorption=0.1325 ln ($Cl_2$ concentration)+ 0.0413. By knowing the absorption, this equation can be used to solve the $Cl_2$ level. The graph can have an R2 value of 0.98 for a curve fit of chlorine between the ranges of 1-4 ppm.

In an embodiment, it can be desirable to maintain a pool with a chlorine level of about 1.0-3.0 ppm. If the pool water has a lower than ideal chlorine level the system can suggest adding chlorine to the pool based on the desired increase in chlorine levels and the volume of the pool. Similar algorithms can be used to calculate the quantities of chemicals needed to reduce the chlorine level of the pool.

The chlorine test chemicals can have specific characteristics which can be important for accurate test results. More specifically, DPD chemistry can distinguish the active sanitizer, termed free available chlorine. When DPD in either liquid form is added to a water sample, a pink color forms with an intensity proportional to the chlorine concentration (either free or total, depending on the step of the procedure). The color of the treated sample is then compared to a set of color standards.

Subtracting the free chlorine reading from the total chlorine reading can yield the amount of combined chlorine in the water. Combined chlorine, an ineffective sanitizer, causes eye and mucous membrane irritation and the so-called "chlorine odor" associated with poorly maintained pools. Combined chlorine is eliminated by super-chlorinating to the breakpoint dosage. Calculations for breakpoint dosage can depend on knowing the amount of combined chlorine in the water, which is why DPD is superior to OT for testing chlorine-sanitized pools.

Without the chlorine phosphate buffer the DPD fades away. When the DPD is oxidized there are two competing products, one is colorless and the other, colored. The colorless can be the preferred product in the solution, thus the phosphate buffer assists in leaving the colored product 20×-30× in time. Also, the slightly acidic pH can be preferred to resolve the chloramine species quantitatively and to minimize interferences.

Total Alkalinity Test

Figure 26:
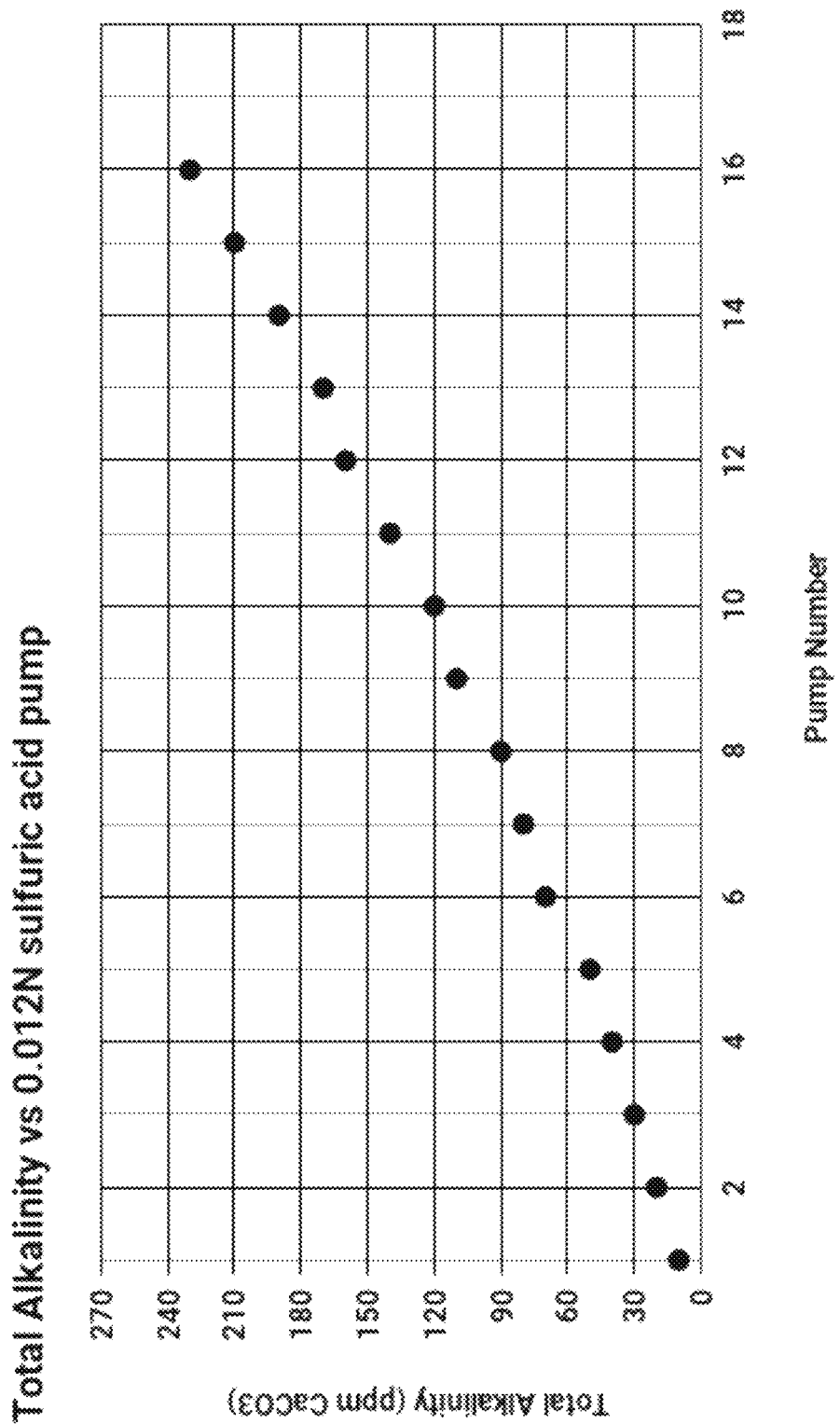
FIG. 26 illustrates a graph showing total alkalinity vs. 0.012N sulfuric acid pump.
Figure 27:
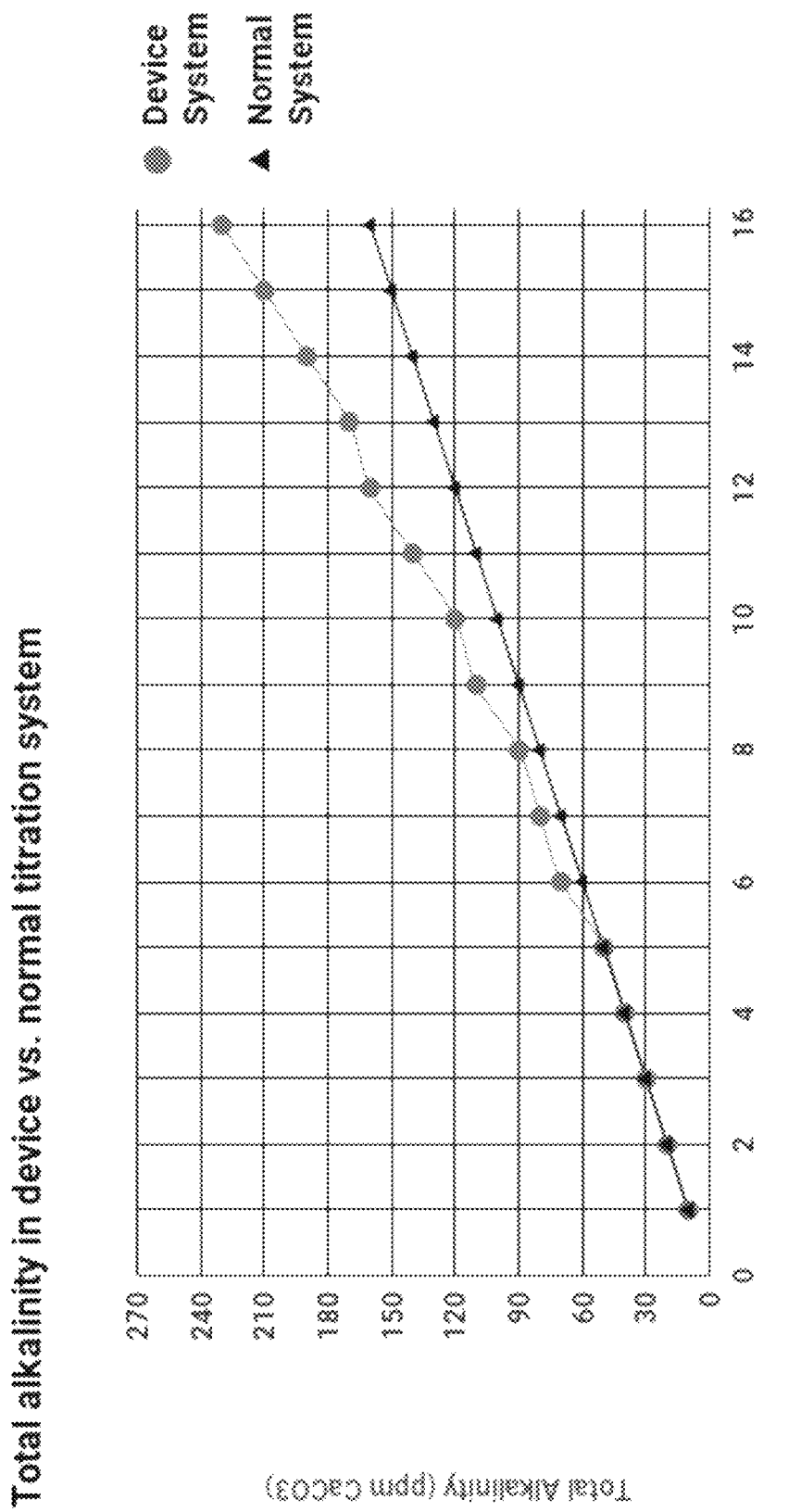
FIG. 27 illustrates a graph showing total alkalinity in a device vs. 0.012N sulfuric acid pump.

The total alkalinity is determined by titrating, similar to a gran titration, to an endpoint pH of 4.5 using a bromocresol green/methyl red blended indicator. The total volume inside the flowcell remains the same, which causes loss from the system. This loss causes the endpoint of the titration to shift depending on the volume of titrant added. FIG. 26 shows the concentration determined from the endpoint in a unit, while FIG. 27 shows how these measurements depart from what is expected in a normal titration. More specifically, FIG. 27 illustrates total alkalinity in a testing device in blue (upper line circular data points) vs Total alkalinity normal system in red (lower line triangular data points).

Figure 28:
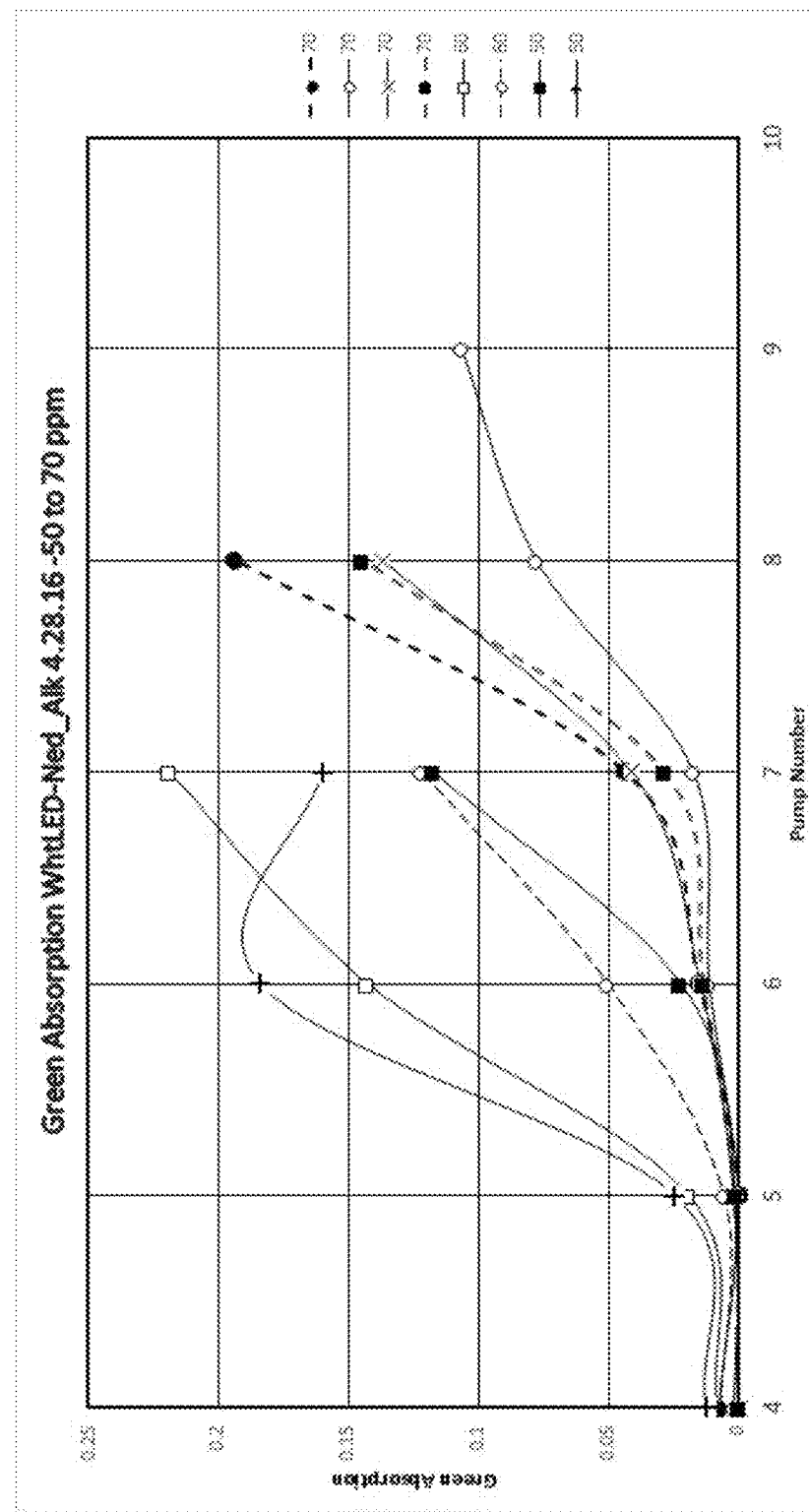
FIG. 28 illustrates a graph of green light absorption with a white LED light source on the y-axis and drops of reagent on the x-axis.

FIG. 28 illustrates a graph of green light absorption with a white LED light source on the y-axis and drops of reagent on the x-axis. The lines on the graph show the changes in light absorption for test samples having various concentrations of $CaCO_3$ including 50, 60, and 70 ppm $CaCO_3$. Each line point represents the change in absorption (~525 nm) between titrant pumps. The two lines on the left that have a transition represent device measurements of 50 ppm $CaCO_3$ with inflection points at about 5-6 pumps of reagent. The middle two lines represent measurements of 60 ppm $CaCO_3$ with inflection points at about 6-7 pumps of reagent. The four right lines represent measurements of 70 ppm $CaCO_3$ with inflection points at about 7-8+ pumps of reagent. The marker values are the manual readings taken with a K-2006 Taylor Technologies test kit measuring total alkalinity. The device is capable of measuring the total alkalinity within 10 ppm $CaCO_3$ of the consumer test kit. By determining the inflection points of the test samples, the quantity of $CaCO_3$ concentrations can be determined.

In another embodiment of alkalinity testing can also be described with reference to FIG. 11 using a two point test method which can include pH level and light absorption data. With reference to FIG. 7, a test water and test chemical sample of + or −1%, the alkalinity test can be accurate within + or −20 ppm $CaCO_3$. The system can fill the flowcell with pool water 371. The system can measure the light absorption of the pool water as a sample blank 372. The system can then mix a reagent with the water 373. In an embodiment, the reagent can be phenol red mixed with a 4-6% v/v volume. In other embodiments, any other suitable reagent and volume can be used. The reagent and water can be light absorption tested 374 which is a first data point which can be the pH level. A titrant can then be added to the water and reagent 375. In an embodiment, the titrant can be 0.012N sulfuric acid added in 0.2% increments. Light absorption testing can be performed 276. The addition of titrant step 375 and measuring steps 376 can be repeated until the end point is determined. In some embodiments, the total light absorption can be measured and in other embodiments, the light absorption for one or more light wavelength frequencies can be measured. Once testing is complete, the flowcell can be flushed with fresh pool water to remove the reagent and the water sample from the flowcell 377. The process can then be repeated for the same or a different water characteristic testing.

FIG. 26 illustrates a graph showing total alkalinity vs. 0.012N sulfuric acid pump. In this example, the pump number can be proportional to equal incremental volumes of 0.012N sulfuric acid added to the test sample. The total alkalinity can be increased with each pump volume added to the test sample. FIG. 27 illustrates a graph showing total alkalinity in a device vs. normal titration system. In this example, the pump number can be proportional to the total alkalinity (ppm $CaCo_3$) of the test sample. The total alkalinity can be increased with each pump volume added to the test sample. There can be a distinction between a normal titration system shown as the lower straight line compared to the device alkalinity shown in the upper line. Adjustments to the total alkalinity can be determined based on this graphical data.

Figure 8:
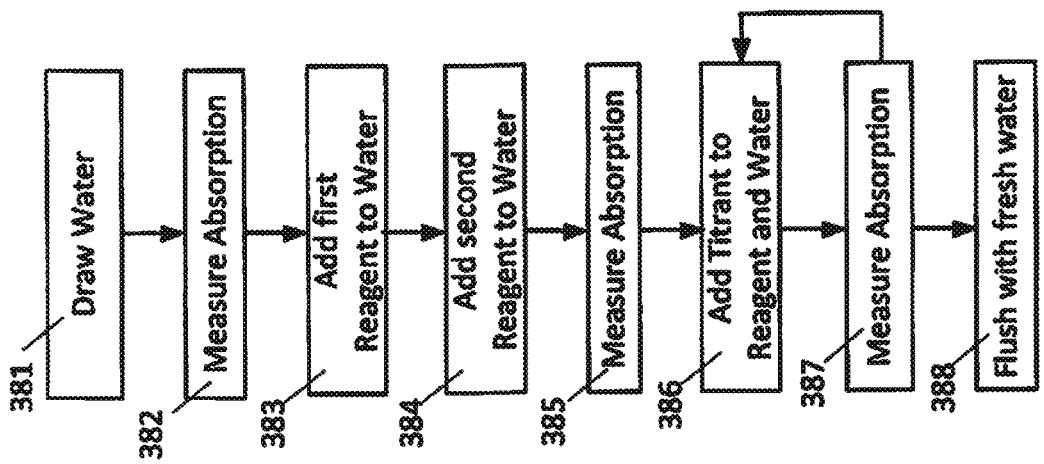
FIG. 8 illustrates a flow chart for an embodiment of alkalinity testing.

In other embodiments, the alkalinity of the pool water can be tested using a full titration method with reference to FIG. 8 using a full titration method. Fresh pool water is drawn into the flowcell 381 and the system can measure the light absorption of the pool water as a sample blank 382. The system can then mix a plurality of reagents with the water. A first reagent can be added to the water 383. In an embodiment, the first reagent can be sodium thiosulfate which is a chlorine neutralizer mixed with a 0.4% v/v volume. A second reagent can then be added to the water 384. In an embodiment, the second reagent can be bromocresol green-methyl red indicator which can be mixed with a 4-6% v/v volume. In other embodiments, any other suitable first and/or second reagents and volumes can be used. The water with first and second reagents can be measured for light absorption 385. A titrant can then be added to the water and reagents 386. In an embodiment, the titrant can be a 0.12N sulfuric acid titrant which can be added with 0.2% v/v volume increments 386. The water with titrant can be measured for light absorption 387. The titrant adding step 386 and the optical measuring step 387 can be repeated until an endpoint is reached. In some embodiments, the total light absorption can be measured and in other embodiments, the light absorption for one or more light wavelength frequencies can be measured. Once testing is completed, the flowcell can be flushed with fresh pool water 388.

Figure 13:
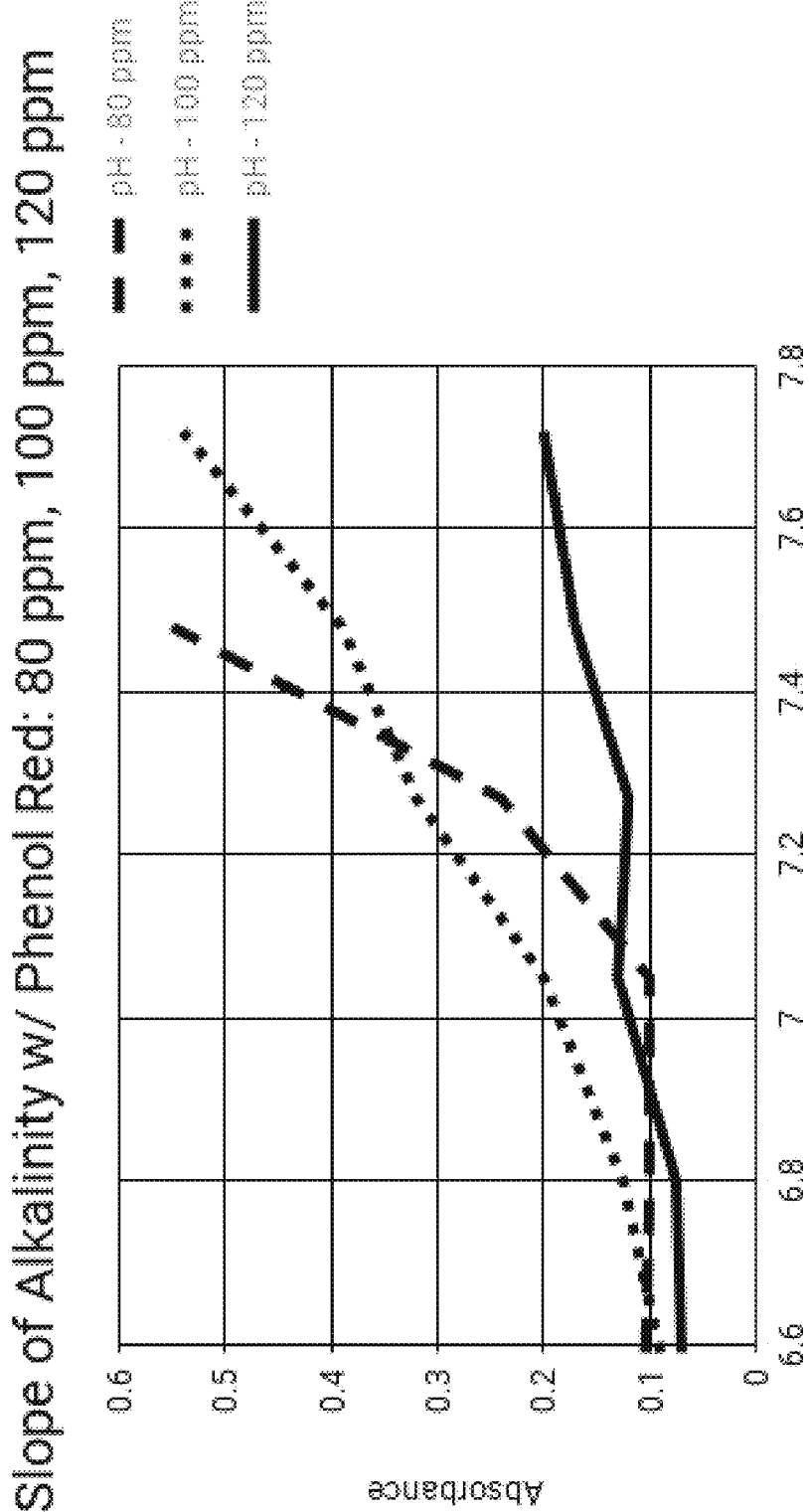
FIG. 13 illustrates a graph of light absorption for alkalinity testing.

Alkalinity can be measured using phenol red as well as a sulfuric acid buffer, which is diluted from the typical Taylor test kit. The graph illustrated in FIG. 13 shows example of the slope changes in light absorbance v. pH change for three different alkalinities of 80, 100, and 120 ppm.

The alkalinity test chemicals can have specific characteristics which can be important for accurate test results. Total alkalinity is a measure of the total amount of dissolved particles in the water whose pH is higher than 7.0. Total Alkalinity (TA) should usually be kept at 80-120 ppm. The sulfuric acid is used as a titrant to estimate the alkalinity based on stock-standard curves. In an embodiment, FIG. 13 illustrates three curves that can be used to estimate the alkalinity given a known amount of citric acid addition given phenol.

Figure 14:
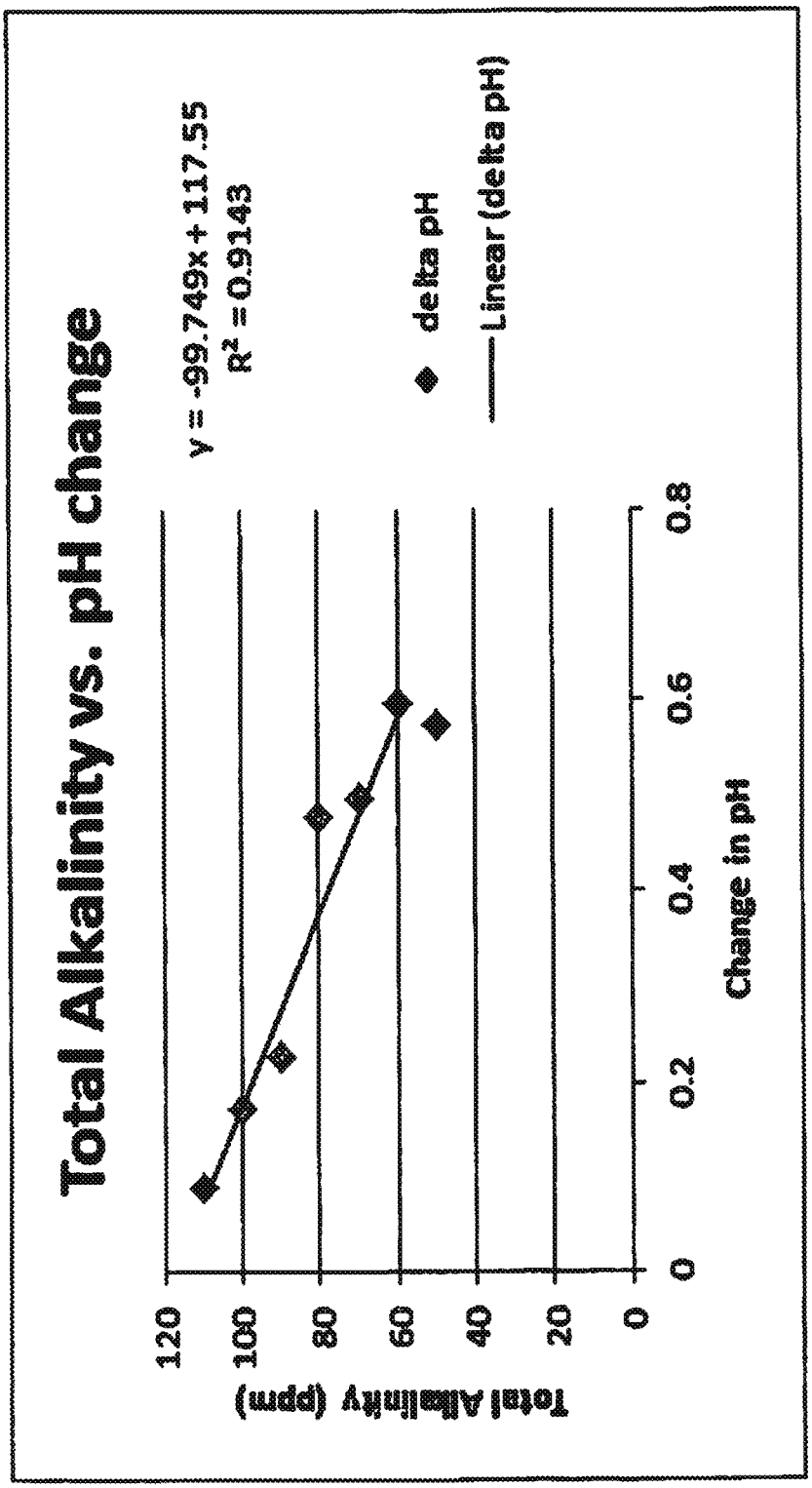
FIG. 14 illustrates a graph of alkalinity for a change in pH.

FIG. 14 illustrates a graph illustrating the total alkalinity in (ppm) as the change in pH. In an embodiment, the relationship between total alkalinity (y) and the change in pH (x) can be represented by the equation, $y=-99.749(x)+117.55$.

Cyanuric Acid Testing

Figure 9:
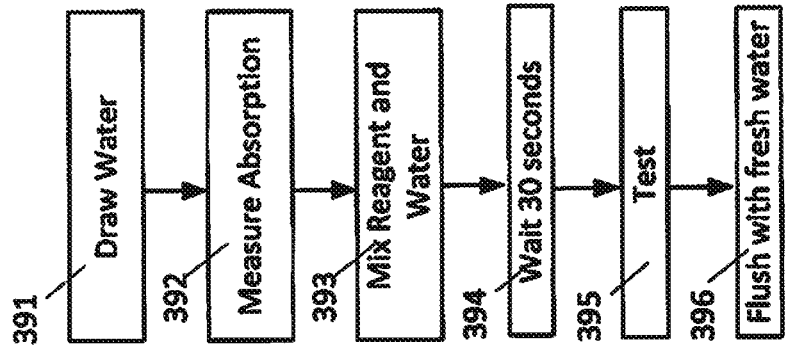
FIG. 9 illustrates a flow chart for an embodiment of cyanuric acid testing.

An embodiment of cyanuric acid testing is described with reference to FIG. 9. With a test water and test chemical sample of + or −5% volume accuracy, the cyanuric acid test can be accurate within + or −11 ppm CYA. For cyanuric acid testing, water is drawn into the flowcell 391. The pool water is exposed to light and measured for light absorption 392. A reagent is added and mixed with the water in the flowcell 393. In an embodiment, the reagent can be a melamine solution which is added at 50% v/v. In other embodiments, any other suitable reagent and volume can be used. The reagent and water can mix for 30 seconds 394. The reagent and water can be light tested and the results can be analyzed for absorption 395. In some embodiments, the total light absorption can be measured and in other embodiments, the light absorption for one or more light wavelength frequencies can be measured. Once testing is completed, the flowcell can be flushed with fresh pool water 396.

Figure 15:
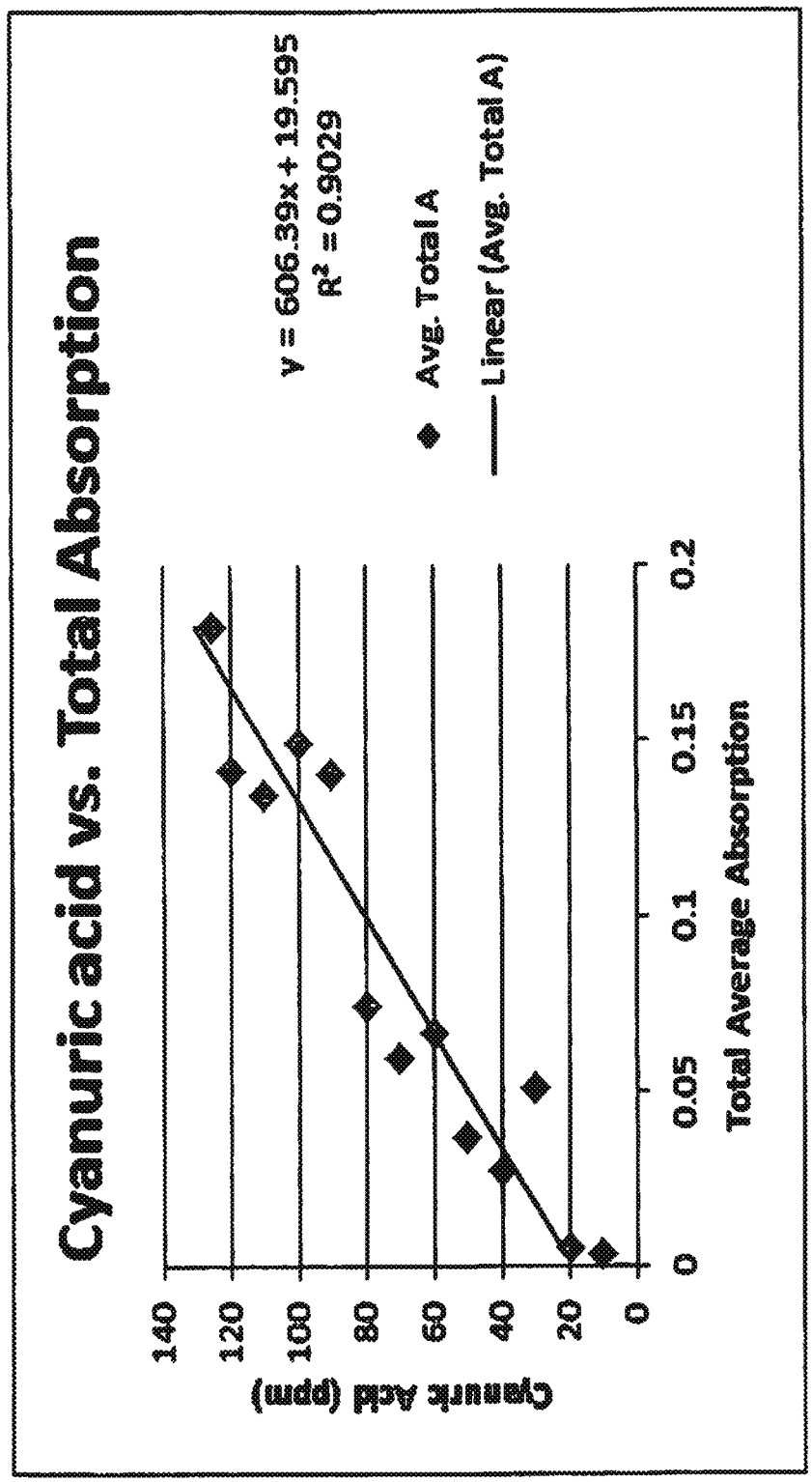
FIG. 15 illustrates a graph of light absorption for cyanuric acid testing.

FIG. 15 illustrates an embodiment of a graph that shows a graphical relationship between the total light absorption and the cyanuric acid levels. The total light absorption may be the total visible light which may not be restricted to specific wavelengths or ranges of wavelengths of light. If the light absorption of the pool water is about 0.05 then the cyanuric acid level can be about 50 ppm. In an embodiment, this relationship can be represented by the algorithm cyanuric acid (ppm)=606.39 (total average light absorption)+19.595. In other embodiments, any other accurate graphs and/or algorithms can be used to convert the light absorption to cyanuric acid level. The ideal cyanuric acid level can depend upon various environmental factors including chlorine loss rate, temperature, sun exposures, etc. When an ideal cyanuric acid level is determined, the system can recommend the addition of chemicals to the pool to correct the cyanuric acid level based on the volume of the pool.

The cyanuric acid test chemicals can have specific characteristics which can be important for accurate test results. The cyanuric acid test is a precipitation measurement, which uses melamine and other buffers to precipitate out the melamine into melaminecyanurate. The graph in FIG. 15 shows at different cyanuric acid ppm concentrations at different total average absorption levels. Testing for cyanuric acid concentration is commonly done with a turbidimetric test, which uses a reagent, melamine, to precipitate the cyanuric acid. The relative turbidity of the reacted sample quantifies the CYA concentration. This test works because melamine combines with the cyanuric acid in the water to form a fine, insoluble, white precipitate (melamine cyanurate) that causes the water to cloud in proportion to the amount of cyanuric acid in it.

Calcium Hardness Testing

Figure 10:
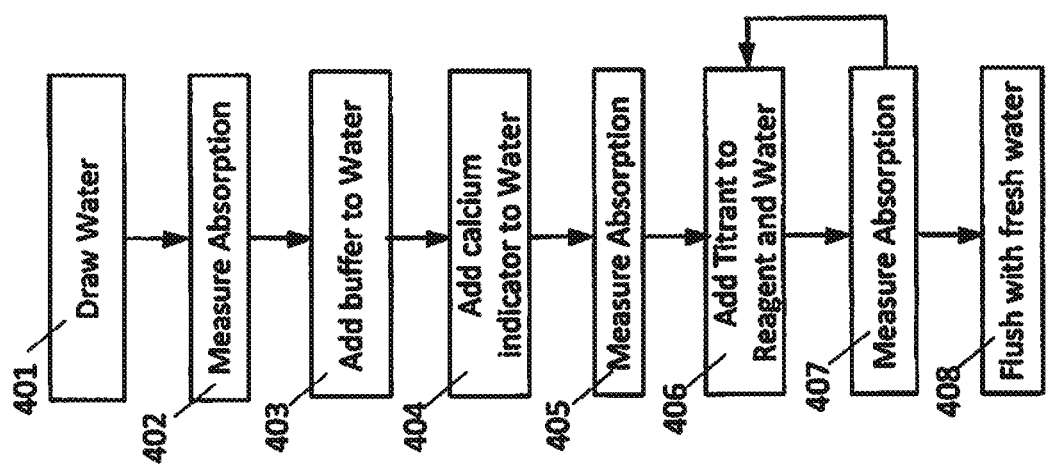
FIG. 10 illustrates a flow chart for an embodiment of calcium hardness testing.

For calcium hardness testing a different procedure may be necessary. With reference to FIG. 10, an embodiment of a calcium hardness test is described. Water is drawn into the flowcell 401. The pool water is exposed to light and measured for light absorption 402. A buffer is added and mixed with the water 403. In an embodiment, the buffer can be a calcium buffer such as NaOH buffer that has a 4% v/v volume. A calcium indicator can then be added to the water 404. In an embodiment, the calcium indicator can be added at 1% v/v volume. The water can then be tested to measure light absorption 405. A titrant can then be added to the water 406. In an embodiment, the titrant can be EDTA 0.02 N titrant which is added at 0.2% v/v increments. The water with buffer, calcium indicator and titrant can then be tested for light absorption 407. The titrant adding step 406 and the test step 407 can be repeated until the endpoint is reached and the calcium hardness can be determined from the test results. Once the testing is completed, the flowcell can be flushed with fresh pool water 408.

Figure 16:
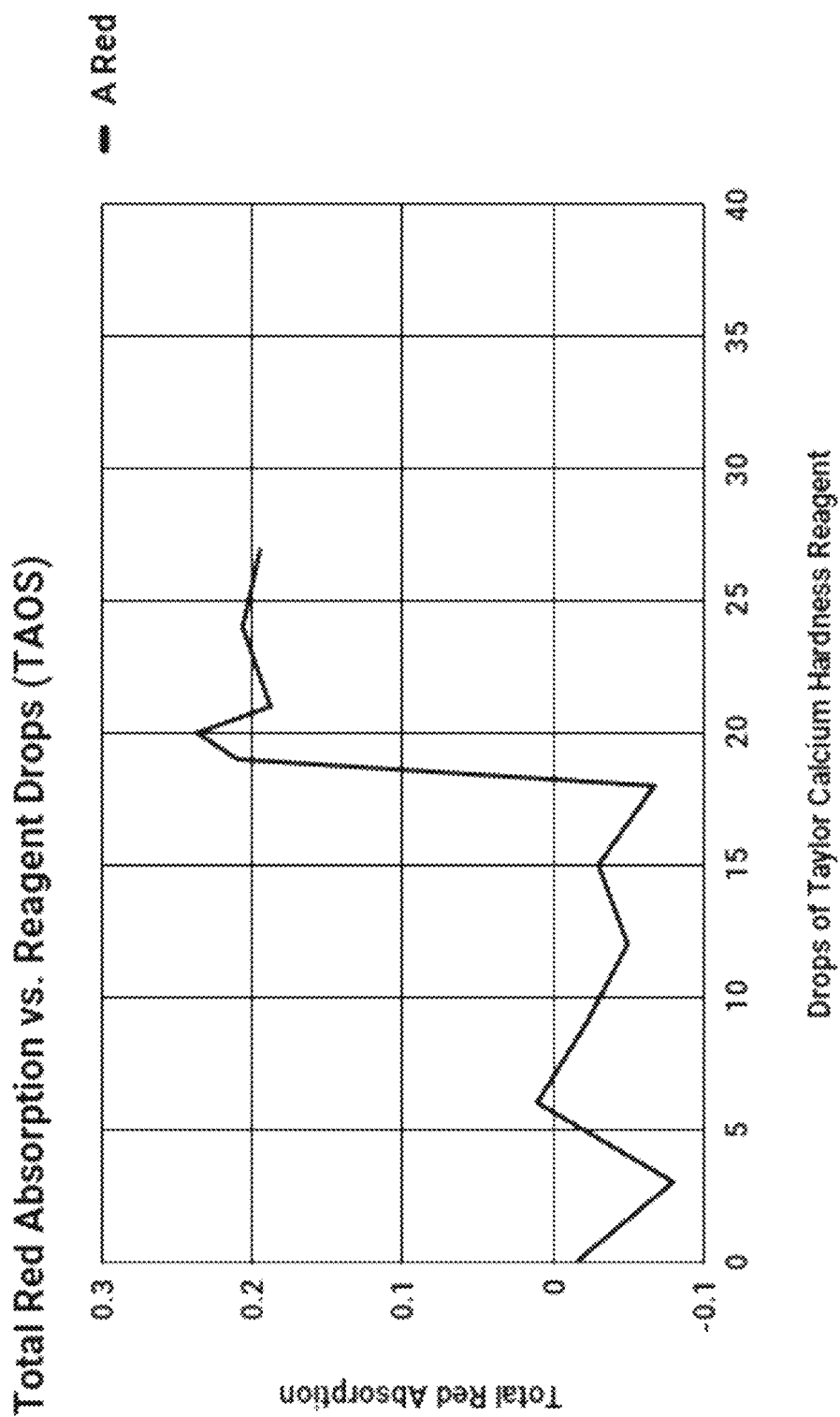
FIG. 16 illustrates a graph of light absorption for calcium hardness testing.

With reference to FIG. 16, a graph of total red absorption v. drops of calcium hardness reagent is illustrated. Calcium hardness can be measured via an inflection point, which results in a large change in the total red absorption. In this example, the inflection point occurs at 19 drops of a Taylor calcium hardness reagent. As additional drops of a Taylor calcium hardness reagent, the total red light absorption value does not substantially change. The volume of reagent added to the water sample needed to reach the inflection point of the total red light absorption indicates the calcium hardness of the water. The ideal calcium hardness can be about 200-400 ppm for pools and 150-250 for spas. This inflection point can be measured by the using the described light testing where light is transmitted through the test samples and the red light absorption can be detected by the light sensor. In this example, the sample can be tested after each drop (or drop volume) of the calcium hardness reagent is added to the sample. The total red absorption can be substantially 0 until 18 drops have been added. When the $19^{th}$ drop of the calcium hardness reagent is added, the total red absorption goes to 0.2 and stays at this level when additional calcium hardness reagent drops are added.

Once the measured calcium hardness is determined, the system can recommend adding chemicals if adjustments are necessary. For example, to increase the calcium hardness the system can recommend adding calcium chloride ($CaCl_2$)). The quantity of calcium chloride recommended by the system can be proportional to the change in calcium chloride level desired and the volume of the body of water, pool or spa.

The calcium hardness test chemicals can have specific characteristics which can be important for accurate test results. EDTA 0.02 N titrant—Disodium dihydrogen ethylenediamine-tetraacetate ($Na_2EDTA$) forms a slightly ionized, colorless, stable complex with alkaline earth ions. The indicator Eriochrome Black T is bright blue in the absence of alkaline earths, but with them forms a deep-red complex that has a higher ionization constant than that of the $Na_2EDTA$ complex. Hence, with Eriochrome Black T as an indicator, the alkaline earth can be titrated with $Na_2EDTA$.

NaOH buffer—ASDAll alkaline earths titrate approximately stoichiometrically. The titration should proceed immediately upon addition of the indicator because the color of the solution fades after standing. The optimum pH of the titration is 10.4 or above. The NaOH buffer achieves this pH for the titration.

Calcium indicator—The indicator Eriochrome Black T is bright blue in the absence of alkaline earths, but with alkaline earths this indicator forms a deep-red complex that has a higher ionization constant than that of the $Na_2EDTA$ complex. Hence, with Eriochrome Black T as an indicator, the alkaline earth can be titrated with $Na_2EDTA$.

Titration is a common method of quantitative chemical analysis that is used to determine the unknown concentration of an identified analyte. A reagent, called the titrant is prepared as a standard solution. A known concentration and volume of titrant reacts with a solution of titrand to determine concentration. The volume of titrant reacted is called titration volume.

Small volumes of the titrant are then added to the analyte and indicator until the indicator changes color in reaction to the titrant saturation threshold, reflecting arrival at the endpoint of the titration. Depending on the endpoint desired, single drops or less than a single drop of the titrant can make the difference between a permanent and temporary change in the indicator. When the endpoint of the reaction is reached, the volume of reactant consumed is measured and used to calculate the concentration of the analyte by the equation:

$$C_a = \frac{C_t V_t M}{V_a}$$

where $C_a$ is the concentration of the analyte, typically in molarity; $C_t$ is the concentration of the titrant, typically in molarity; $V_t$ is the volume of the titrant used, typically in liters; M is the mole ratio of the analyte and reactant from the balanced chemical equation; and $V_a$ is the volume of the analyte used, typically in liters.

A titration curve is a curve in the plane whose x-coordinate is the volume of titrant added since the beginning of the titration, and whose y-coordinate is the concentration of the analyte at the corresponding stage of the titration (in an acid-base titration, the y-coordinate is usually the pH of the solution).

In an acid-base titration, the titration curve reflects the strength of the corresponding acid and base. For a strong acid and a strong base, the curve will be relatively smooth and very steep near the equivalence point. Because of this, a small change in titrant volume near the equivalence point results in a large pH change and many indicators would be appropriate.

If one reagent is a weak acid or base and the other is a strong acid or base, the titration curve is irregular and the pH shifts less with small additions of titrant near the equivalence point. For example, the titration curve for the titration between oxalic acid (a weak acid) and sodium hydroxide (a strong base) is pictured. The equivalence point occurs between pH 8-10, indicating the solution is basic at the equivalence point and an indicator such as phenolphthalein would be appropriate. Titration curves corresponding to weak bases and strong acids are similarly behaved, with the solution being acidic at the equivalence point and indicators such as methyl orange and bromothymol blue being most appropriate.

System Operations

Figure 17:
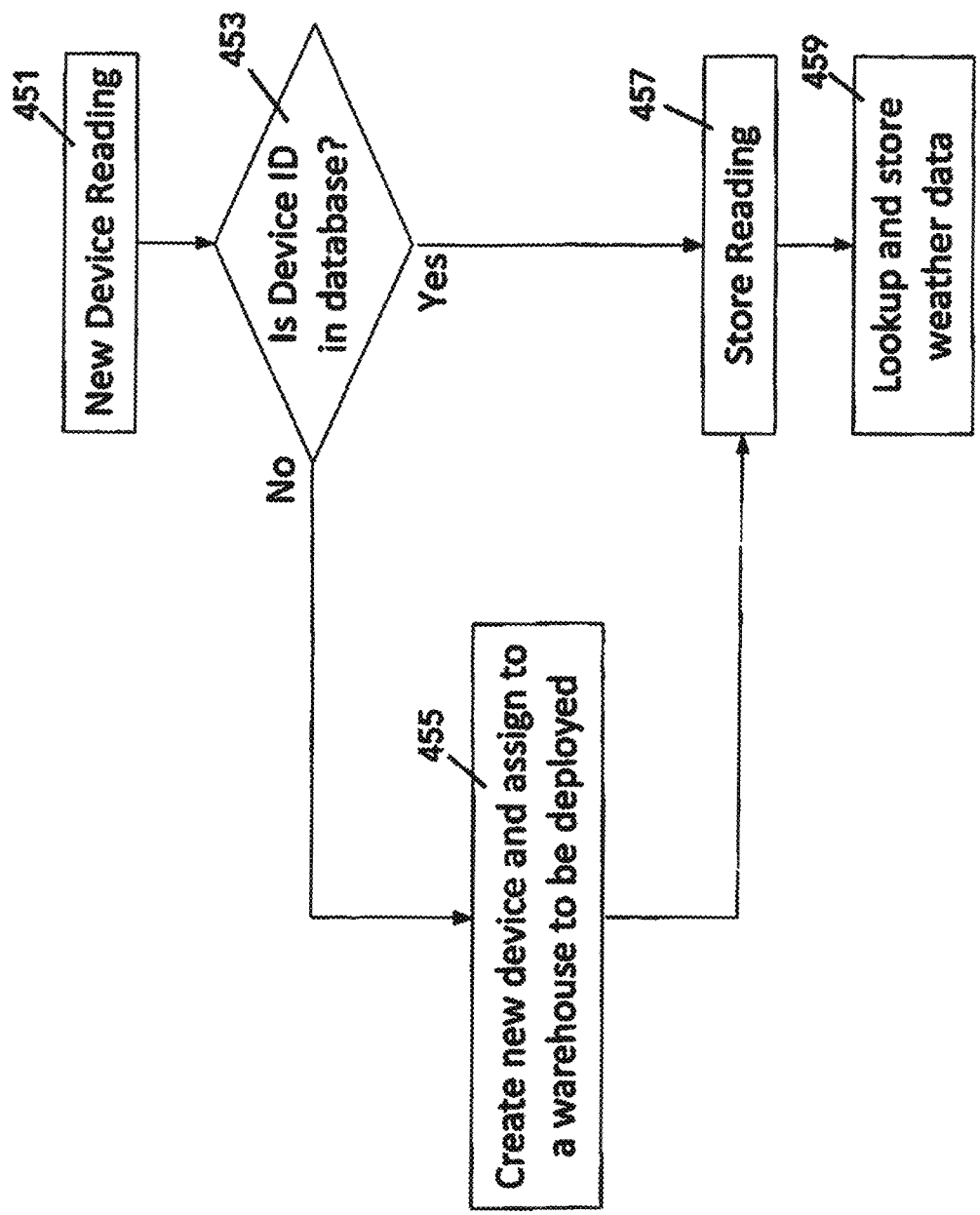
FIGS. 17 and 18 illustrate flow charts for setting up water monitoring systems.

In an embodiment, the system can require an initial set up process after the water monitoring device is purchased. With reference to FIG. 17, an embodiment of the system set up process is illustrated. The water monitoring device can be coupled to a home network and the user can download a water monitoring application program to a computing device such as a smartphone that can run a setup process. The application can read identification information for the new water monitoring device 451 and the identification information can be transmitted through a network to a water monitoring server to determine if the device is in a database. The system will then use the device identification information and determine if the device ID is in the system database. If the device is new, it will not be in the database. The server will inform the computing device that the device is not in the database and the server will create a new record for the new device and associated information such as location, pool information, chemical information, local warehouse for chemicals, etc. 455. The device, device ID and associated information can then be stored in the server and/or local computing device database 457. Based on the location of the pool, the system can lookup and store current and future predicted weather data 459.

The current and upcoming weather for the location of the body of water can be used to predict future chemical use. For example, hotter temperatures and sun exposure will result in a faster loss of chlorine rate. In an embodiment, the inventive system can factor in the thermal and solar exposure of the pool based on the weather and season of the year. The system can increase the predicted consumption of chlorine based on elevated temperatures and increased sun exposure or conversely reduce the predicted consumption of chlorine based on lower temperatures and decreased sun exposure.

Figure 18:
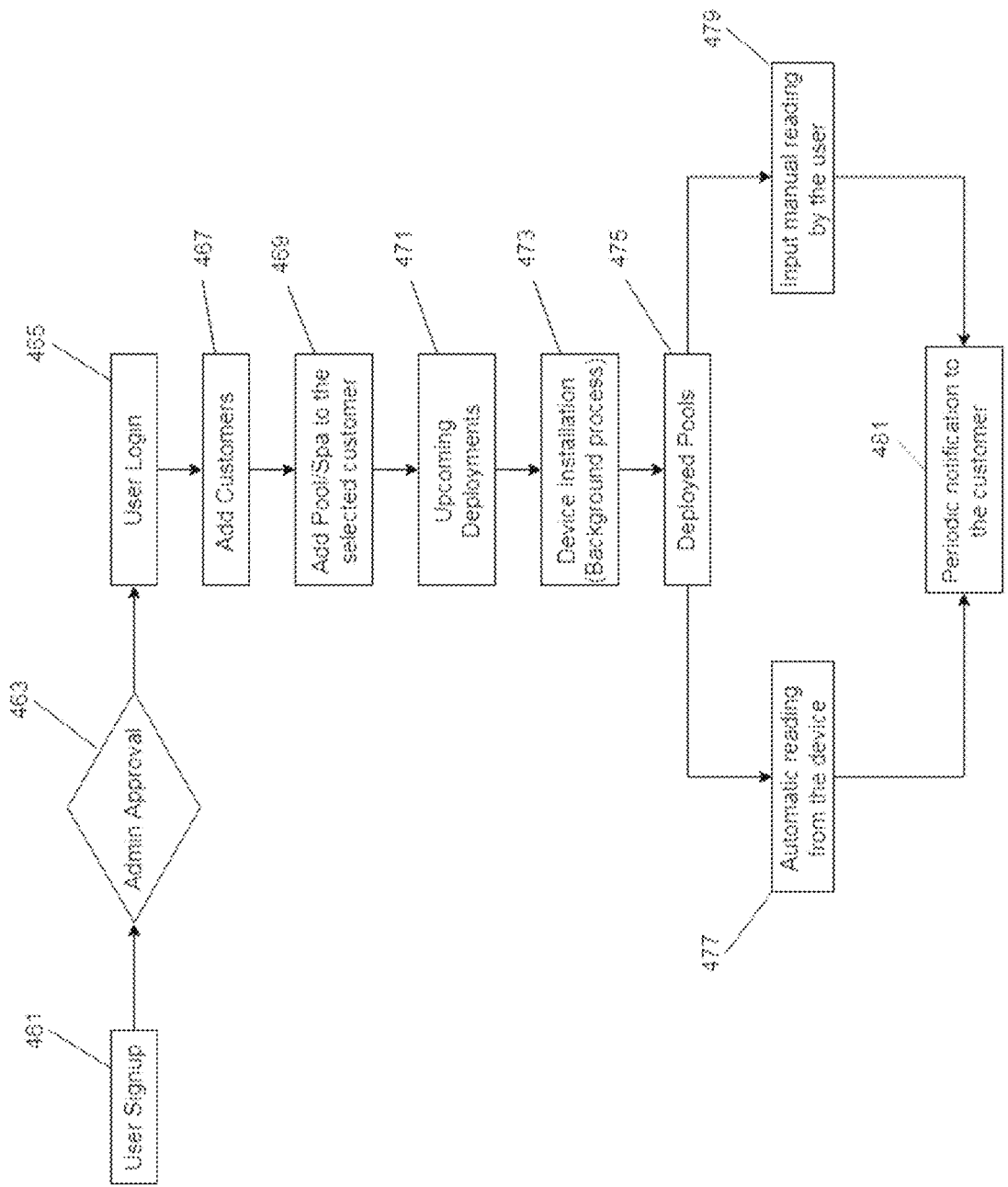

With reference to FIG. 18, another embodiment of a flowchart for setting up a water monitoring system is illustrated. An application program can be used by a new user to input signup information 461 into a computing device. The signup request can be transmitted to a server and a system administrator can accept or reject the new user 463. If the user is accepted, the system can provide secure (such as password protected) user login information. The user can then login to the server 465. The server can add the new customer to the user database 467. The user can input pool or spa information through a user interface and this information can be added to the database and can be associated with the customer 469. The user can configure the system to function in the desired manner such as selecting automated and/or manual pool measurements, chemical notifications and/or deliveries, automated or manual software updates, etc. Based on the user and pool information, the system can determine upcoming deployments 471 of pool chemicals. The system can then run through a water monitoring device installation process 473. In an embodiment, this device installation process can run in the background automatically through the computing device and the water monitoring device. The installation can include updates to software and/or firmware. Once setup, the device can be deployed to the pool 475. The system can be configured to perform automatic readings from the water monitoring device 477 or perform pool readings based on manual inputs to the computing device 479. The monitoring information from the pool can be transmitted to the computing device and/or server. Based on the water monitoring information, the server and/or computing device can provide periodic notifications to the customer user regarding the status of the pool.

In different embodiments, the user's computing device includes a receiver that receives and stores a set of values in the water monitoring database for a body of water. The described testing for a water sample can store the total volume of the body of water and determine the chemicals needed to optimize the chemical levels for the body of water. The system can then scale the quantity of the chemical that can be added to the total volume of the body of water. A larger body of water will require larger quantities of chemicals to adjust the chemical characteristics than a smaller body of water. The data fields that this controller currently receives and processes including information for: battery, water and air temperature, light, pH level, chlorine level, alkalinity, cyanuric acid level and calcium hardness.

In an embodiment, a Python script has been developed to simulate the device updates. This script can send static data to the water monitoring application program running on the computing device through an API call. For example, in an embodiment, a weather API can be called every time a reading is obtained from a water monitoring device. This call can be originated in the receiver and can change and be limited to a rate of not more than one call per hour. In an embodiment, the weather API can fetch one or more weather details such as: temperature, relative humidity, ultraviolet (UV) and wind speed based on the zip code of the pool's/spa's location. This information can be used to update the user pool database and can be applied to other pool databases in the area.

Based on the pool monitoring information, that is transmitted to the user's computer, various messages can be transmitted to a computing device associated with the pool maintenance person. More specifically, the system processor can include the following messages and processing: 1. Everything is good with the user's pool (or spa). 2. The user needs to reboot device as there are some issues with connectivity, 3. The user needs to put some chemicals in their pool and 4. The user needs to refill chemicals in storage.

If everything is good the user computing device, which can include a mobile computing device such as a smart phone. The user computing device can display a user interface which indicates that all is good and no action is required. The user interface may display information regarding the actual pool chemical measurements and temperature.

If the system needs to be rebooted, the user computing device user interface can display a reboot control button which the user can press to actuate the reboot procedure. The system can restart the software application and hopefully reestablish connectivity between the system components. If the system is successful, the system will display "everything is good" on the user interface. If connectivity problems persist, the user interface may ask the user to check the power supply and/or network functionality to determine if the network is down.

If pool chemicals are needed, the system can provide instructions to the user computing device regarding which chemicals should be added to the pool and the quantity of the chemicals that need to be added to the body of water. In an embodiment, the inventive system can communicate with a pool maintenance service which can be instructed to put the required chemicals in the pool. The water monitoring device can retest the water and if the pool chemicals and measurements are at the desired levels, the system can display "everything is good" on the user interface.

In an embodiment, the system can monitor the chemicals in storage as well as the chemicals consumed by the pool as instructed by the system. When a supply of chemicals is running low, the system can inform the pool maintenance person. In an embodiment, the user interface can include a button that can be pressed by the user to order the needed chemicals. The system can provide the cost for the chemicals and delivery/tax costs. If the user agrees to the sale price, the system can electronically order the necessary chemicals which can be picked up or delivered to the pool.

Replaceable Reagent Cartridge

Figure 35:
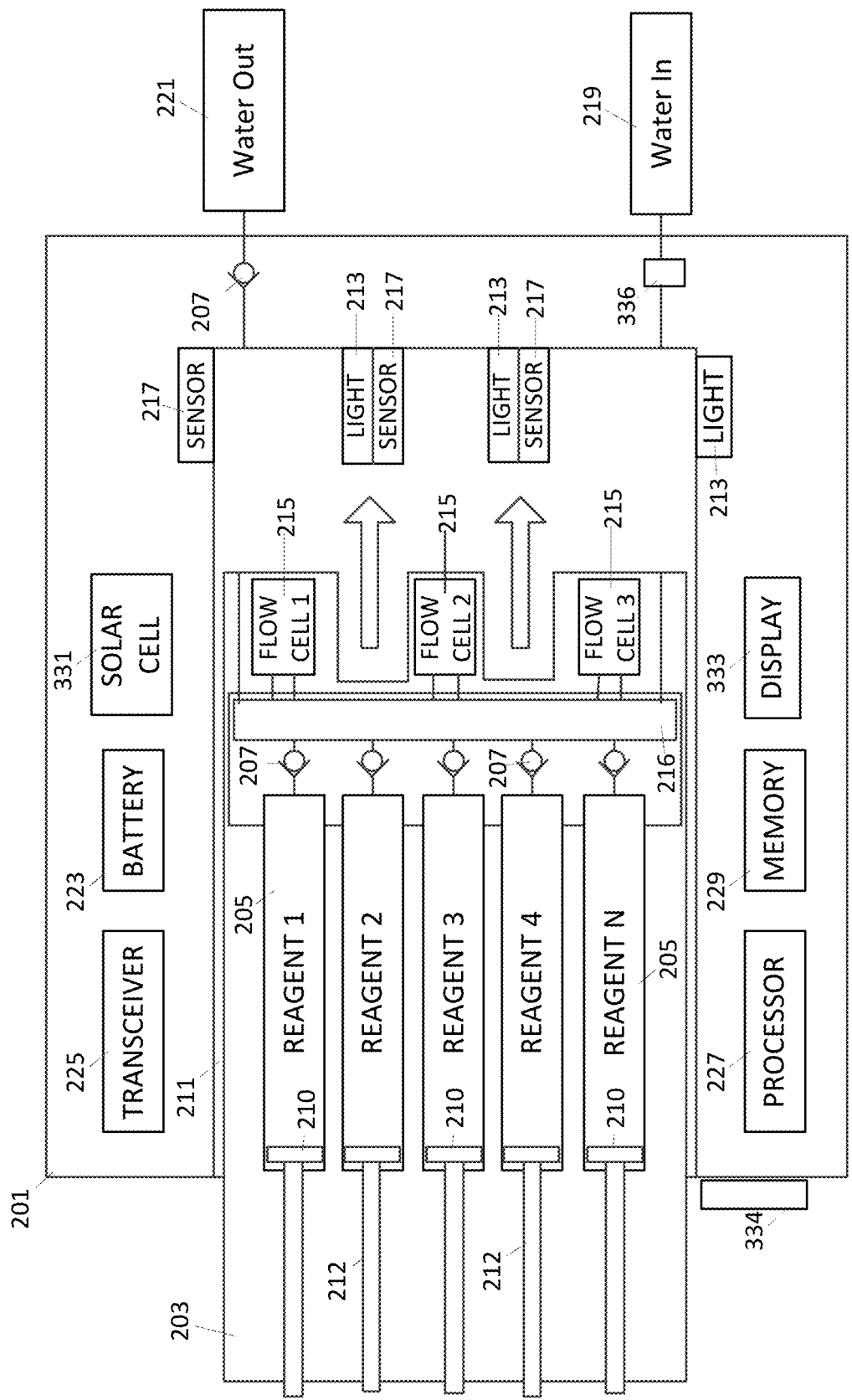
FIG. 35 illustrates an embodiment of a replaceable reagent cartridge being placed in the water monitoring unit.

As discussed above, the water monitoring unit can include a replaceable reagent cartridge design. With reference to FIG. 35, an embodiment of a water monitoring unit with a replaceable reagent cartridge fluidic chip cartridge 203 is illustrated that is inserted into a slot in the water monitoring unit 201 is illustrated. The replaceable reagent cartridge fluidic chip cartridge 203 can include: plunger rods 212, plungers 210, reagents in reagent storage 205 volumes, check valves 207, a fluid manifold 216, and flowcells 215. In the illustrated embodiment, the light sources 213 and the light sensors 217 are not components of the replaceable reagent cartridge fluidic chip cartridge 203. The reagent storage 205 can be syringes or other elongated tubular structures. In the illustrated embodiment, the reagent storage 205 includes five tubular structures with each of the reagent storage 205 units storing a different reagent fluid. The replaceable reagent cartridge fluidic chip cartridge 203 can have two recessed slots between the adjacent flowcells 215. The cross section of the replaceable reagent cartridge fluidic chip cartridge 203 can be rectangular in shape and the cross section of the slot cartridge receptacle 211 in the water monitoring unit 201 can be a rectangular shape that is larger than the cross section of the replaceable reagent cartridge fluidic chip cartridge 203.

Figure 36:
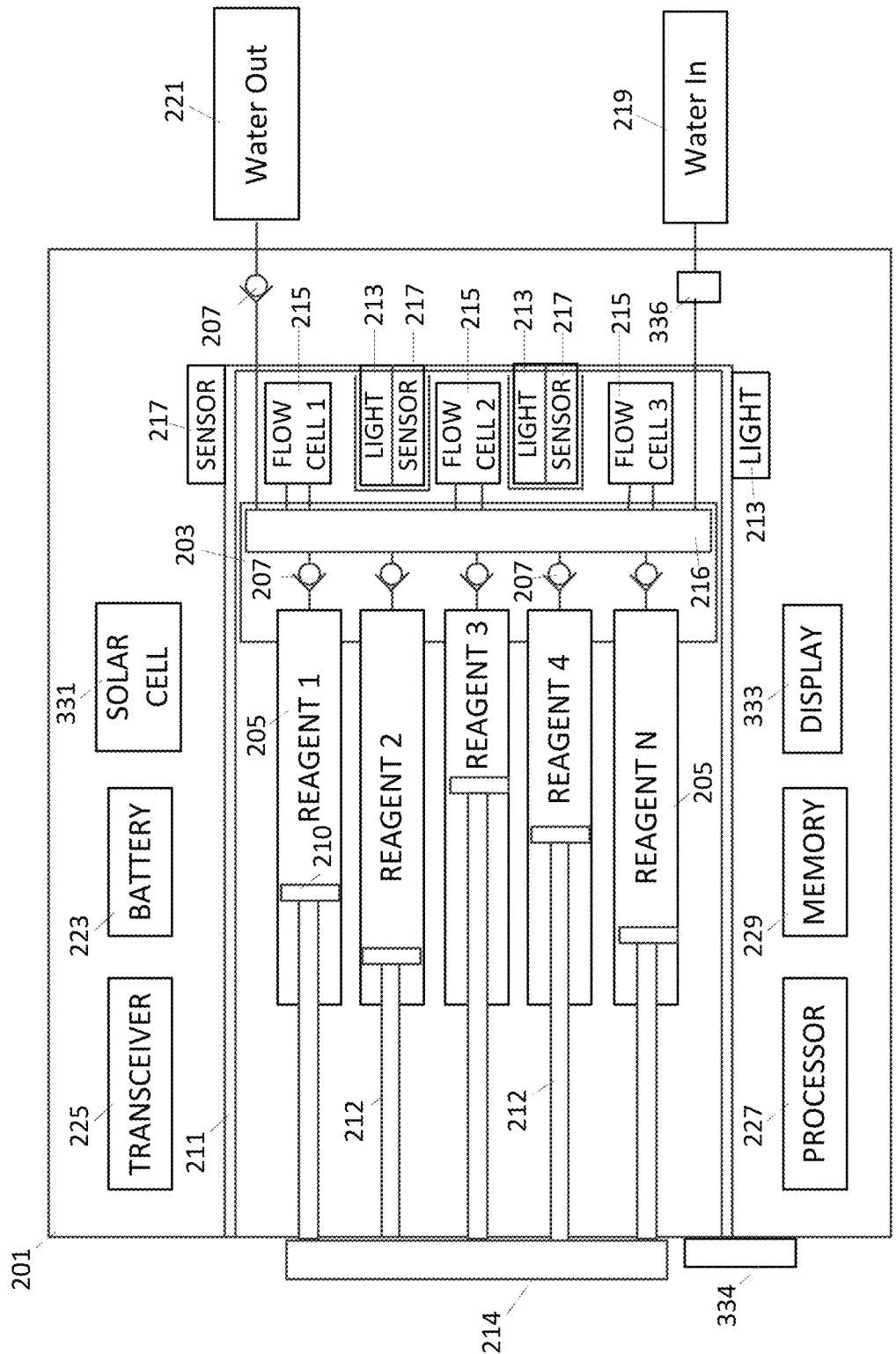
FIGS. 36 and 37 each illustrate an embodiment of a replaceable reagent cartridge fully inserted in the water monitoring unit.

With reference to FIG. 36, when the replaceable reagent cartridge fluidic chip cartridge 203 is fully inserted into the water monitoring unit 201, each of the flowcells 215 can be placed between a light source 213 and a light sensor 217. A locking mechanism 334 can hold and compress the replaceable reagent cartridge fluidic chip cartridge 203 against an inner surface at the bottom of the slot of the water monitoring unit 201. The plungers 205 and plunger rods 212 can be coupled to a plunger driver mechanism 214 to control the movements of the plungers 205 and the flow of the reagents. The replaceable reagent cartridge fluidic chip cartridge 203 and the water monitoring unit 201 can have water flow paths that are aligned and sealed when the replaceable reagent cartridge fluidic chip cartridge 203 is fully inserted into the water monitoring unit 201. In an embodiment, the water flow paths can have elastic seals that can seal the inlet and outlet water flow paths when the replaceable reagent cartridge fluidic chip cartridge 203 is compressed inner surface at the bottom of the slot in the water monitoring unit 201.

In the illustrated embodiment, the light sources 213 and the light sensors 217 are not components of the replaceable reagent cartridge fluidic chip cartridge 203. When fully inserted, a light source 213 and/or a light sensor 217 can be placed in each of the recessed slots of the replaceable reagent cartridge fluidic chip cartridge 203. The light source 213 configured to direct light through one of the flowcells 215 and the light sensors 217 configured to detect light transmitted through one of the flowcells 215.

Before water testing is performed, a pump 336 can cause water to flow into and out of the flowcells 215. In an embodiment, the volume of water transmitted through the flowcells 215 can be proportional to the volume of the flowcells 215. For example, if the volume of the flowcells 215, the water volume for cleaning the flowcell 215 can be ten times this volume. Thus, a 1.0 milliliter flowcell 215 can use 10.0 milliliters of water for cleaning. Prior to and/or after each test, the system can actuate the pump 336 and the required volume of water will flow through the flowcell 215 for cleaning. In other embodiments, the system can be configured to use any other volume of water for cleaning such as 5 to 20 times the volume of the flowcell 215. At the end of the cleaning process, the flowcells 215 are filled with fresh water from the water source.

The movements of the plungers 210 are controlled by the plunger driver mechanism 214 which can move the plunger rods 212 to drive the plungers 210 into the reagent storage 205 tubes. in different embodiments, the replaceable reagent cartridge 203 can have any number of reagent storage 205 units that are filled with any type of reagent for water or any other type of liquid testing can be performed. The plunger driver mechanism 214 can include gears that drive multiple plungers 210 which can pump multiple reagents into the flowcells 215. In other embodiments, the plunger driver mechanism 214 can individually and independently control the plungers 210. Alternatively, the system can provide a plunger driver mechanism 214 that includes a geared system that drives multiple plungers 210 and an individual driver that controls a single plunger 210.

In order to mix the reagents with water, the plunger driver mechanism 214 can be actuated and the reagent fluids can flow through check valves 207 and the fluid manifold 216 into the flowcells 215. The check valves 207 can prevent the reagent from flowing backwards into the reagent storage. The reagents from the reagent storage 205 and water from the water inlet 219 are mixed in the flowcells 215. After the water and reagents are thoroughly mixed, the chemical testing can be performed by illuminating the light sources and detecting the transmitted light with the light sensors. Because the device can include multiple flowcells 215, multiple different water tests can be performed simultaneously.

Once the testing is completed, the water and reagent mixture can be pumped out of the flowcells 215 of the water monitoring unit 201 through the pool water outlet 221. In an embodiment, the reagent removal can be performed by pumping fresh water into the flowcells 215 which forces the old water and reagent mixture out of the flowcells 215. The water monitoring system can then pump water into the flowcells 215 to clean or flush any residual reagent chemicals from the flowcells 215 before additional water testing is performed. In an embodiment, the pumps 209 can be peristaltic, diaphragm, syringe, blister pack or any other suitable chemical pump mechanism. The flow of reagents into the flowcells 215 can be controlled to deliver the fluid volume of 25 microliters (μL) per test with an error rate of less than 5%.

Figure 37:
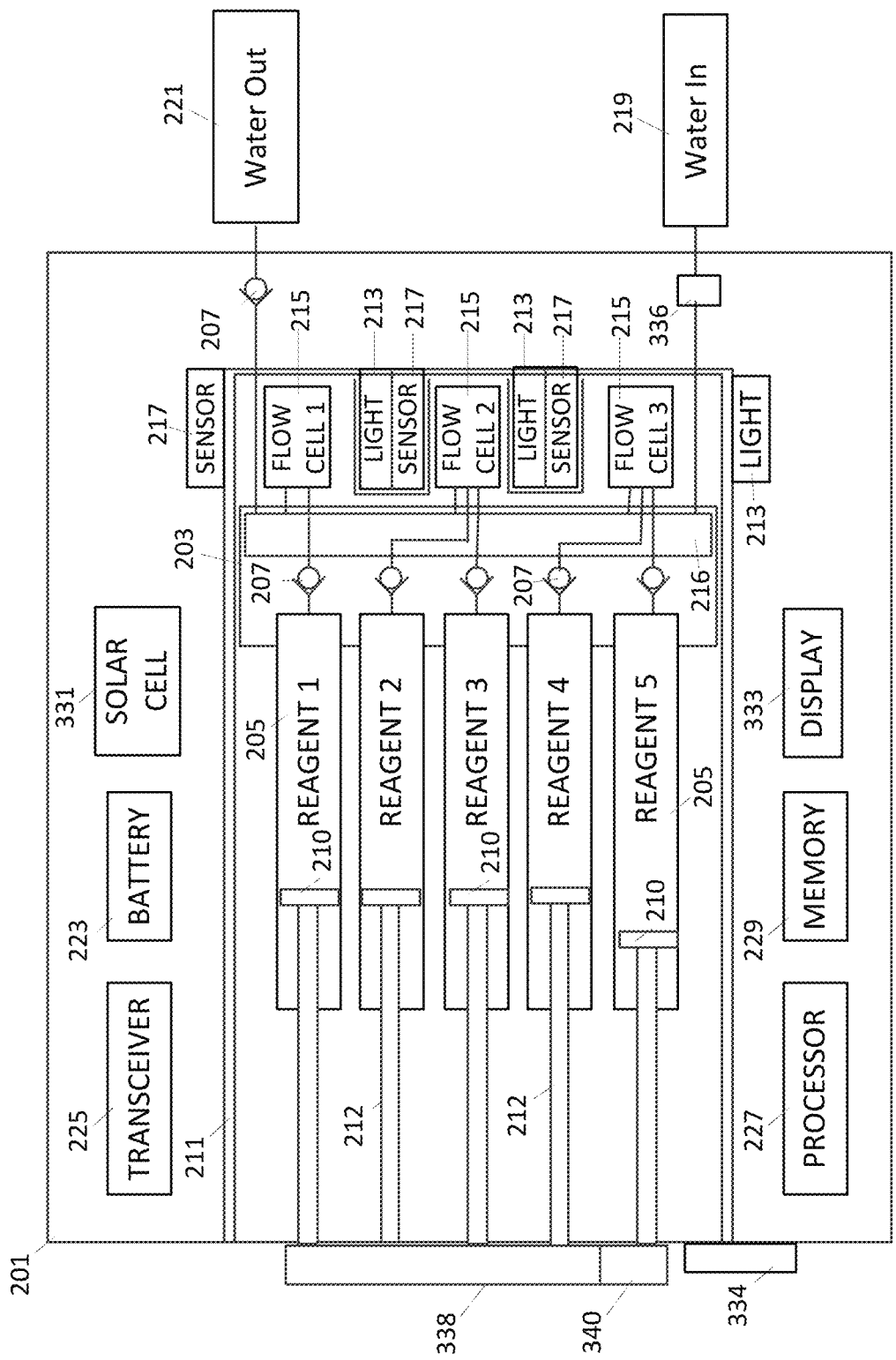

In an embodiment with reference to FIG. 37, the five reagent storage 205 cylinders of the replaceable reagent cartridge 203 can be filled with: 1. phenol red 2. free chlorine phosphate buffer 3. free chlorine DPD 4, sulfuric acid titrant 5. sodium thiosulfate chlorine neutralizer bromocresol green methyl red indicator. The phenol red (Reagent 1) can be mixed with water in the first flowcell 215 and pH testing can be performed. The free chlorine phosphate buffer and the free chlorine DPD reagent (Reagents 2 and 3) can be mixed with water in the second flowcell 215 and free chlorine testing is performed. The sulfuric acid (Reagent 4) is mixed with water in the third flowcell 215 and sodium thiosulfate is titrated for alkalinity testing. The plungers 210 in reagent storage 205 containers reagents 1-4 can be coupled to a drive system 338 which can have gears coupled to a stepper motor that can be controlled to rotate a specific number or fraction of rotations. The drive system 338 can be configured to simultaneously drive these plungers 210 to pump reagents into the flowcells 215. The pH and the chlorine testing can be performed by transmitting light from the light sources 213 through first and second flowcells 215 and detecting the intensities of the wavelengths of light transmitted through these flowcells 215. The pH and the chlorine values for the water can be determined by the system based on the detected transmitted light as described above.

The alkalinity of the water can be determined by testing performed in the third flowcell 215. As discussed, the water in the third flowcell 215 can be mixed with sulfuric acid (Reagent 4). However, in order to determine the alkalinity, a titration process can be performed. An independent drive mechanism 340 can be coupled only to the plunger 210 in the sodium thiosulfate reagent storage 205 container. The independent drive mechanism 340 can include a stepper motor that can be controlled to rotate a specific number or fraction of rotations. The independent drive mechanism 340 can be actuated and a small predetermined volume of the sodium thiosulfate reagent can be delivered to the third flowcell 215. Light from the light sources 213 can be transmitted through third flowcell 215 and the intensities of the wavelengths of light transmitted is detected by the light sensor 217. This process can be repeated until a chemical reaction occurs that results in an optical indication which is an optical change in the transmitted light. By knowing the volume of the sodium thiosulfate reagent that results in the optical indication, the alkalinity of the water can be determined.

The replaceable reagent cartridge 203 can have a sufficient volume of reagents to perform about 100 water tests. When the reagent levels are running low and the system issues a warning that the reagent cartridge 203 needs to be replaced. In an embodiment, the system can calculate the remaining number of tests and information to a mobile computing device which can be displayed on a user interface of an application program running on the mobile computing device.

Figure 38:
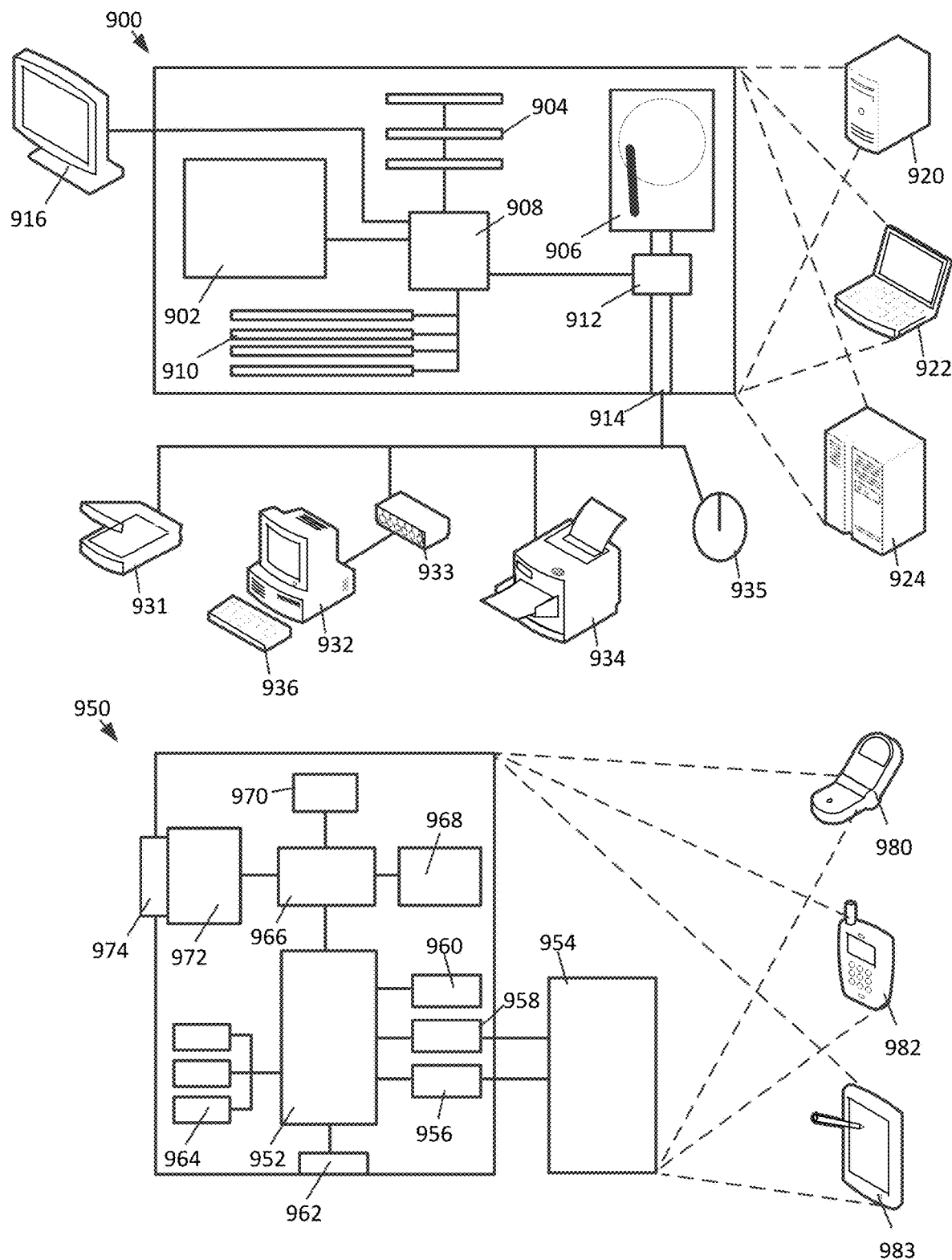
FIG. 38 illustrates a block diagram of the computer system.

FIG. 38 shows an example of a generic computer device 900 and a generic mobile computer device 950, which may be used to implement the processes described herein, including the mobile-side and server-side processes for installing a computer program from a mobile device to a computer. Computing device 900 is intended to represent various forms of digital computers, such as laptops, desktops, workstations, personal digital assistants, servers, blade servers, mainframes, and other appropriate computers. Computing device 950 is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

Computing device 900 includes a processor 902, memory 904, a storage device 906, a high-speed interface 908 connecting to memory 904 and high-speed expansion ports 910, and a low speed interface 912 connecting to low speed bus 914 and storage device 906. Each of the components processor 902, memory 904, storage device 906, high-speed interface 908, high-speed expansion ports 910, and low speed interface 912 are interconnected using various busses, and may be mounted on a common motherboard or in other manners as appropriate. The processor 902 can process instructions for execution within the computing device 900, including instructions stored in the memory 904 or on the storage device 906 to display graphical information for a GUI on an external input/output device, such as display 916 coupled to high speed interface 908. In other implementations, multiple processors and/or multiple busses may be used, as appropriate, along with multiple memories and types of memory. Also, multiple computing devices 900 may be connected, with each device providing portions of the necessary operations (e.g., as a server bank, a group of blade servers, or a multi-processor system).

The memory 904 stores information within the computing device 900. In one implementation, the memory 904 is a volatile memory unit or units. In another implementation, the memory 904 is a non-volatile memory unit or units. The memory 904 may also be another form of computer-readable medium, such as a magnetic or optical disk.

The storage device 906 is capable of providing mass storage for the computing device 900. In one implementation, the storage device 906 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier may be a non-transitory computer- or machine-readable storage medium, such as the memory 904, the storage device 906, or memory on processor 902.

The high speed controller 908 manages bandwidth-intensive operations for the computing device 900, while the low speed controller 912 manages lower bandwidth-intensive operations. Such allocation of functions is exemplary only. In one implementation, the high-speed controller 908 is coupled to memory 904, display 916 (e.g., through a graphics processor or accelerator), and to high-speed expansion ports 910, which may accept various expansion cards (not shown). In the implementation, low-speed controller 912 is coupled to storage device 906 and low-speed expansion port 914. The low-speed expansion port 914, which may include various communication ports (e.g., USB, Bluetooth, Ethernet, wireless Ethernet), may be coupled to one or more input/output devices, such as a keyboard 936 in communication with a computer 932, a pointing device 935, a scanner 931, or a networking device 933 such as a switch or router, e.g., through a network adapter.

The computing device 900 may be implemented in a number of different forms, as shown in the figure. For example, it may be implemented as a standard server 920, or multiple times in a group of such servers. It may also be implemented as part of a rack server system 924. In addition, it may be implemented in a personal computer such as a laptop computer 922. Alternatively, components from computing device 900 may be combined with other components in a mobile device (not shown), such as device 950. Each of such devices may contain one or more of computing device 900, 950, and an entire system may be made up of multiple computing devices 900, 950 communicating with each other.

Computing device 950 includes a processor 952, memory 964, an input/output device such as a display 954, a communication interface 966, and a transceiver 968, among other components. The device 950 may also be provided with a storage device, such as a Microdrive, solid state memory or other device, to provide additional storage. Each of the components computing device 950, processor 952, memory 964, display 954, communication interface 966, and transceiver 968 are interconnected using various busses, and several of the components may be mounted on a common motherboard or in other manners as appropriate.

The processor 952 can execute instructions within the computing device 950, including instructions stored in the memory 964. The processor may be implemented as a chipset of chips that include separate and multiple analog and digital processors. The processor may provide, for example, for coordination of the other components of the device 950, such as control of user interfaces, applications run by device 950, and wireless communication by device 950.

Processor 952 may communicate with a user through control interface 958 and display interface 956 coupled to a display 954. The display 954 may be, for example, a TFT LCD (Thin-Film-Transistor Liquid Crystal Display) or an OLED (Organic Light Emitting Diode) display, or other appropriate display technology. The display interface 956 may comprise appropriate circuitry for driving the display 954 to present graphical and other information to a user. The control interface 958 may receive commands from a user and convert them for submission to the processor 952. In addition, an external interface 962 may be provided in communication with processor 952, so as to enable near area communication of device 950 with other devices. External interface 962 may provide, for example, for wired communication in some implementations, or for wireless communication in other implementations, and multiple interfaces may also be used.

The memory 964 stores information within the computing device 950. The memory 964 can be implemented as one or more of a computer-readable medium or media, a volatile memory unit or units, or a non-volatile memory unit or units. Expansion memory 974 may also be provided and connected to device 950 through expansion interface 972, which may include, for example, a SIMM (Single In Line Memory Module) card interface. Such expansion memory 974 may provide extra storage space for device 950, or may also store applications or other information for device 950. Specifically, expansion memory 974 may include instructions to carry out or supplement the processes described above, and may include secure information also. Thus, for example, expansion memory 974 may be provide as a security module for device 950, and may be programmed with instructions that permit secure use of device 950. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 964, expansion memory 974, memory on processor 952, or a propagated signal that may be received, for example, over transceiver 968 or external interface 962.

Device 950 may communicate wirelessly through communication interface 966, which may include digital signal processing circuitry where necessary. Communication interface 966 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 968. In addition, short-range communication may occur, such as using a Bluetooth, Wi-Fi, or other such transceiver (not shown). In addition, GPS (Global Positioning System) receiver module 970 may provide additional navigation- and location-related wireless data to device 950, which may be used as appropriate by applications running on device 950.

Device 950 may also communicate audibly using audio codec 960, which may receive spoken information from a user and convert it to usable digital information. Audio codec 960 may likewise generate audible sound for a user, such as through a speaker, e.g., in a handset of device 950. Such sound may include sound from voice telephone calls, may include recorded sound (e.g., voice messages, music files, etc.) and may also include sound generated by applications operating on device 950.

The computing device 950 may be implemented in a number of different forms, as shown in the figure. For example, it may be implemented as a cellular telephone 980. It may also be implemented as part of a smartphone 982, personal digital assistant, a tablet computer 983 or other similar mobile computing device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

The present disclosure, in various embodiments, includes components, methods, processes, systems and/or apparatus substantially as depicted and described herein, including various embodiments, sub-combinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

What is claimed is:

1. A water monitoring system comprising:
a water monitoring device comprising:
   a cartridge fluidic chip having: a first reagent, a light source, a flowcell for mixing the first reagent and water, a light sensor for detecting light from the light source that is transmitted through the water and the first reagent placed in the flowcell;
   a processor coupled to the light sensor for analyzing light data from the light sensor and determining a chemical level of the water;
   a transmitter coupled to the processor for transmitting the chemical level of the water;
   a battery for storing electrical energy and powering the processor, light source, light sensor and transmitter; and
   a housing surrounding the processor, the cartridge fluidic chip, transmitter and battery;
wherein the light sensor detects the transmitted light through the first reagent and the water in the flowcell at a first wavelength and a second wavelength that has a longer length than the first wavelength and the chemical level of the water is determined by the processor based upon a ratio of the transmitted light at the first wavelength divided by the transmitted light at the second wavelength.

* * * * *